US009321791B2

(12) United States Patent
Himmelsbach et al.

(10) Patent No.: US 9,321,791 B2
(45) Date of Patent: Apr. 26, 2016

(54) 8-[3-AMINO-PIPERIDIN-1-YL]-XANTHINES, THE PREPARATION THEREOF AND THEIR USE AS PHARMACEUTICAL COMPOSITIONS

(71) Applicant: Boehringer Ingelheim International GmbH, Ingelheim am Rhein (DE)

(72) Inventors: Frank Himmelsbach, Mittelbiberach (DE); Elke Langkopf, Biberach an der Riss (DE); Matthias Eckhardt, Biberach an der Riss (DE); Michael Mark, Biberach an der Riss (DE); Roland Maier, Biberach an der Riss (DE); Ralf Lotz, Schemmerhofen (DE); Mohammad Tadayyon, Welwyn Garden City (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/748,792

(22) Filed: Jun. 24, 2015

(65) Prior Publication Data
US 2015/0291627 A1 Oct. 15, 2015

Related U.S. Application Data

(63) Continuation of application No. 14/154,885, filed on Jan. 14, 2014, which is a continuation of application No. 13/448,495, filed on Apr. 17, 2012, now Pat. No. 8,664,232, which is a continuation of application No. 12/143,128, filed on Jun. 20, 2008, now Pat. No. 8,178,541, which is a continuation of application No. 10/639,036, filed on Aug. 12, 2003, now Pat. No. 7,407,955.

(60) Provisional application No. 60/461,752, filed on Apr. 10, 2003, provisional application No. 60/409,312, filed on Sep. 9, 2002.

(30) Foreign Application Priority Data

Aug. 21, 2002 (DE) .................................. 102 38 243
Mar. 20, 2003 (DE) .................................. 103 12 353

(51) Int. Cl.
C07D 473/08 (2006.01)
C07D 519/00 (2006.01)
C07D 473/04 (2006.01)
C07D 473/06 (2006.01)

(52) U.S. Cl.
CPC ............ *C07D 519/00* (2013.01); *C07D 473/04* (2013.01); *C07D 473/06* (2013.01); *C07D 473/08* (2013.01)

(58) Field of Classification Search
CPC .................................................. C07D 473/08
See application file for complete search history.

(56) References Cited

U.S. PATENT DOCUMENTS

| | | | |
|---|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,382,091 A | 5/1983 | Benjamin et al. |
| 4,599,338 A | 7/1986 | Regnier et al. |
| 4,639,436 A | 1/1987 | Junge et al. |

(Continued)

FOREIGN PATENT DOCUMENTS

| | | |
|---|---|---|
| AU | 2003280680 A1 | 6/2004 |
| AU | 2009224546 A1 | 9/2009 |
| CA | 1123437 A1 | 5/1982 |
| CA | 2136288 A1 | 5/1995 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |

(Continued)

OTHER PUBLICATIONS

Weber, Ann. J. Med. Chem. 2004, 47, 4135-4141.*

(Continued)

*Primary Examiner* — Golam M M Shameem
*Assistant Examiner* — Laura Daniel
(74) *Attorney, Agent, or Firm* — Michael P. Morris; David L. Kershner

(57) ABSTRACT

The present invention relates to substituted xanthines of general formula (I)

wherein $R^1$ to $R^3$ are as defined herein, the tautomers, the stereoisomers, the mixtures, the prodrugs thereof and the salts thereof which have valuable pharmacological properties, particularly an inhibiting effect on the activity of the enzyme dipeptidylpeptidase-IV (DPP-IV).

4 Claims, No Drawings

(56) References Cited

U.S. PATENT DOCUMENTS

| | | |
|---|---|---|
| 4,687,777 A | 8/1987 | Meguro et al. |
| 4,743,450 A | 5/1988 | Harris et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,517 A | 9/1991 | Findeisen et al. |
| 5,084,460 A | 1/1992 | Munson, Jr. et al. |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,448,323 B1 | 9/2002 | Jordan et al. |
| 6,548,481 B1 | 4/2003 | Demuth et al. |
| 6,579,868 B1 | 6/2003 | Asano et al. |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,995,183 B2 | 2/2006 | Hamann et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,235,538 B2 | 6/2007 | Kanstrup et al. |
| 7,247,478 B2 | 7/2007 | Eberhardt et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,673,927 B2 | 3/2014 | Dugi et al. |
| 8,679,520 B2 | 3/2014 | Horres et al. |
| 8,785,455 B2 | 7/2014 | Hotter et al. |
| 8,865,729 B2 | 10/2014 | Sieger et al. |
| 8,962,636 B2 | 2/2015 | Pfrengle et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0078269 A1 | 4/2003 | Pearson et al. |
| 2003/0100563 A1 | 5/2003 | Edmondson et al. |
| 2003/0104053 A1 | 6/2003 | Gusler et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0037883 A1 | 2/2004 | Zhou et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |

(56) References Cited

U.S. PATENT DOCUMENTS

| | | |
|---|---|---|
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0034922 A1 | 2/2006 | Cheng et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0027168 A1 | 2/2007 | Pfrengle et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0254944 A1 | 11/2007 | Hughes |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0033177 A1 | 2/2010 | Ochi et al. |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2011/0009391 A1 | 1/2011 | Braun et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0324463 A1 | 12/2013 | Klein et al. |
| 2014/0371243 A1 | 12/2014 | Klein et al. |
| 2015/0196565 A1 | 7/2015 | Klein et al. |

FOREIGN PATENT DOCUMENTS

| | | |
|---|---|---|
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2651019 A1 | 11/2007 |
| CA | 2651089 A1 | 11/2007 |
| CN | 101234105 A | 8/2008 |
| DE | 2205815 A1 | 8/1973 |
| DE | 2758025 A1 | 7/1979 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |

(56) References Cited

FOREIGN PATENT DOCUMENTS

| | | |
|---|---|---|
| EP | 0524482 A1 | 1/1993 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004250336 A | 9/2004 |
| JP | 2006045156 A | 2/2006 |
| JP | 2010053576 A | 3/2010 |
| JP | 2010070576 A | 4/2010 |
| JP | 2010524580 A | 7/2010 |
| KR | 20070111099 A | 11/2007 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9611917 A1 | 4/1996 |
| WO | 9636638 A1 | 11/1996 |
| WO | 9718814 A1 | 5/1997 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9818770 A1 | 5/1998 |
| WO | 9822464 A1 | 5/1998 |
| WO | 9828007 A1 | 7/1998 |
| WO | 9840069 A2 | 9/1998 |
| WO | 9846082 A1 | 10/1998 |
| WO | 9856406 A1 | 12/1998 |
| WO | 9929695 A1 | 6/1999 |
| WO | 9938501 A2 | 8/1999 |
| WO | 9950248 A1 | 10/1999 |
| WO | 9956561 A1 | 11/1999 |
| WO | 9967279 A1 | 12/1999 |
| WO | 0073307 A2 | 12/2000 |
| WO | 0107441 A1 | 2/2001 |
| WO | 0140180 A2 | 6/2001 |
| WO | 0147514 A1 | 7/2001 |
| WO | 0151919 | 7/2001 |
| WO | 0152825 | 7/2001 |
| WO | 0152852 A1 | 7/2001 |
| WO | 0166548 A1 | 9/2001 |
| WO | 0168603 | 9/2001 |
| WO | 0168646 A1 | 9/2001 |
| WO | 0172290 A2 | 10/2001 |
| WO | 0177110 A1 | 10/2001 |
| WO | 0196301 A1 | 12/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02068420 A1 | 9/2002 |
| WO | 03000241 A2 | 1/2003 |
| WO | 03000250 | 1/2003 |
| WO | 03002531 A2 | 1/2003 |
| WO | 03002553 A2 | 1/2003 |
| WO | 03004496 A1 | 1/2003 |
| WO | 03024965 A2 | 3/2003 |
| WO | 03033686 A2 | 4/2003 |
| WO | 03034944 A1 | 5/2003 |
| WO | 03035177 A2 | 5/2003 |
| WO | 03037327 A1 | 5/2003 |
| WO | 03053929 A1 | 7/2003 |
| WO | 03055881 A1 | 7/2003 |
| WO | 03057200 A2 | 7/2003 |
| WO | 03059327 | 7/2003 |
| WO | 03064454 A1 | 8/2003 |
| WO | 03074500 A2 | 9/2003 |
| WO | 03088900 A2 | 10/2003 |
| WO | 03094909 A2 | 11/2003 |
| WO | 03099279 A1 | 12/2003 |
| WO | 03099836 A1 | 12/2003 |
| WO | 03104229 A1 | 12/2003 |
| WO | 03106428 A1 | 12/2003 |
| WO | 2004002924 A1 | 1/2004 |
| WO | 2004011416 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005007658 A2 | 1/2005 |
| WO | 2005012288 A1 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005082906 A1 | 9/2005 |

(56) References Cited

FOREIGN PATENT DOCUMENTS

| | | |
|---|---|---|
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 2007033350 A1 | 3/2007 |
| WO | 2007035355 A2 | 3/2007 |
| WO | 2007035665 A1 | 3/2007 |
| WO | 2007041053 A2 | 4/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092124 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010140111 A1 | 12/2010 |
| WO | 2010147768 A1 | 12/2010 |
| WO | 2011011541 A1 | 1/2011 |
| WO | 2011039337 A1 | 4/2011 |
| WO | 2011039367 A2 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2011163206 A2 | 12/2011 |
| WO | 2012031124 A2 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |
| WO | 2013098372 A1 | 7/2013 |
| WO | 2013103629 A1 | 7/2013 |
| WO | 2013171167 A1 | 11/2013 |
| WO | 2013174768 A1 | 11/2013 |

OTHER PUBLICATIONS

WebMD. Autoimmune Diseases: What are Autoimmune Disorders. 1-3 (2015) < http://www.webmd.com/a-to-z-guides/autoimmune-diseases?print=true>.*
Abstract for AU 2003280680, Jun. 18, 2004.
Abstract for AU 2009224546, Sep. 17, 2009.
Abstract in English for German DE10109021, 2002.
Abstract in English for German DE2205815, 1972.
Abstract in English for German EP0023032, 1981.
Abstract in English for JP 2002/348279, Dec. 4, 2002.
Abstract in English for JP 2003/286287, Oct. 10, 2003.
Abstract in English, for KR20070111099, Nov. 11, 2007.
Adebowale, K.O. et al., "Modification and properties of African yam bean (*Sphenostylis stenocarpa* Hochst. Ex A. Rich.) Harms starch I: Heat moisture treatments and annealing." Food Hydrocolloids, 2009, vol. 23, No. 7, pp. 1947-1957.
Ahren, Bo "Novel combination treatment of type 2 diabetes DPP-4 inhibition + metformin." Vascular Health and Risk Management, 2008, vol. 4, No. 2, pp. 383-394.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, Bo; "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Alter, M. et al. "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.

(56) References Cited

OTHER PUBLICATIONS

American Diabetes Association, "Standards of Medical Care in Diabetes—2008." Diabetes Care, Jan. 2008, vol. 31, Supplement 1, pp. S12-S54.
Anstee, Quentin M. et al. "Mouse models in non-alcholic fatty liver disease and steatohepatitis research" (2006) International Journal of Expermental Pathology, vol. 87, pp. 1-16.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determination of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Aulinger, B.A. et al., "Ex-4 and the DPP-IV Inhibitor Vildagliptin have Additive Effects to Suppress Food Intake in Rodents". Abstract No. 1545-P, 2008.
Baetta, R. et al., "Pharmacology of Dipeptidyl Peptidase-4 Inhibitors." Drugs, 2011, vol. 71, No. 11, pp. 1441-1467.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balbach, S. et al., "Pharmaceutical evaluation of early development candidates the 100 mg-approach." International Journal of Pharmaceutics, 2004, vol. 275, pp. 1-12.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Bastin, R.J. et al., "Salt Selection and Optimization Procedures for Pharmaceutical New Chemical Entities". Organic Process Research and Development, 2000, vol. 4, p. 427-435.
Beljean-Leymarie et al., Hydrazines et hydrazones hétérocycliques. IV. Synthéses de dérives de l'hydrazine dans la série des imidazo[4,5-d]pyridazinones-4, Can. J. Chem., vol. 61, No. 11, 1983, pp. 2563-2566.
Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.
Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.

Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitution/sn_2/sn 2. vlu/Page/vsc/en/ch/12/oc/substitution/sn_2/abgangsgrupen/abgangsgruppe.vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-,S-(2-[[[1-(2-ethylbutyl)cyclohexyl}carbonyl}amino}pheyl}ester". Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 N O3. American Chemical Society, Feb. 28, 2006.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Hunziker, D. et al, "Inhibitors of DPP IV-recent advances and structural views", Current Topics in Medicinal Chemistry, 2005, vol. 5 issue 16, pp. 1623-1637.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
International Search Report—European Search Report for PCT/EP2003/09127 mailed Mar. 1, 2011.
Inukai, T., "Treatment of Diabetes in Patients for Whom Metformin Treatment is Not Appropriate." Modern Physician, 2008, vol. 28, No. 2, pp. 163-165.
Isomaa, B. et al., "Cardiovascular Morbidity and Mortality Associated With the Metabolic Syndrome." Diabetes Care, 2001, vol. 24, No. 4, pp. 683-689.
Iwamoto, Yasuhiko, "Insulin Glargine." Nippon Rinsho, 2002, vol. 60, Suppl. 9, pp. 503-515.
Januvia; Patient Information; 2010.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.

(56) References Cited

OTHER PUBLICATIONS

John Hopkins Children's Center, "Liver Disorders and Diseases." Retrieved online May 26, 2014 <http://www.hopkinschildrens.org/non-alcoholic-fatty-liver-disease.aspx>.

Jones, R.M. et al., "GPR119 agonists for the treatment of type 2 diabetes". Expert Opinion on Therapeutic Patents 2009 Informa Healthcare for GBR LNKSD—DOI: 0.1517/13543770903153878, vol. 19, No. 10, Oct. 2009, p. 1339-1359.

Kanada, S. et al., "Safety, tolerability, pharmacokenetics and pharmacodynamics of multiple doses of BI 1356 (proposed tradename Ondero), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kelly. T., "Fibroblast activation protein-cx and dipeptidyl peptidase IV (CD26)P: Cell-surface proteases that activate cell signaling and are potential targets for cancern therapy". Drug Resistence Update 8, 2005, vol. 8. No. 1-2, pp. 51-58.

Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.

Kharkevich, D. A., "Educational Literature" Pharmacology (1987) Third Edition, Meditsina Press, Moscow pp. 47-48.

Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.

Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.

Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Kim, Kwang-Rok et al., "KR-62436, 6-{2-{2-(5-cyano4,5-dihydropyrazol-1-yl)-2-oxoethylamino}ethylamino}nicotinonitrile, is a novel dipeptidyl peptidase-IV (DDP-IV inhibitor with anti-hyperglycemic activity" European Journal of Pharmacology 518, 2005, p. 63-70.

Kitaly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.

Klein, T. et al., "Linagliptin alleviates hepatic steatosis and inflammation in a mouse model of non-alcoholic steatohepatitis." Medical Molecular Morphology, 2014, vol. 47, pp. 137-149.

Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.

Komori, Kiyoshi., "Treatment of Diabetes in Patients for Whom Metforming Treatment is Not Appropriate" Modern Physician (2008) vol. 28, No. 2 pp. 163-165.

Konstantinou, D. M. et al., "Pathophysiology-based novel pharmacotherapy for heart failure with preserved ejection fraction." Pharmacology & Therapeutics, 2013, vol. 140, No. 2, pp. 156-166.

Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.

Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.

Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.

Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

Lee Jones, K. et al., "Effect of Metformin in Pediatric Patients With Type 2 Diabetes." Diabetes Care, 2002, vol. 25, No. 1, pp. 89-94.

Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.

Levien,T.L. et al, "New drugs in development for the treatment of diabetes", Diabetes Spectrum, American Diabetes Association, US, vol. 22, No. 2, Jan. 1, 2009, pp. 92-106.

Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.

Linagliptin Monograph, Published by VACO PBM-SHG US Veteran's Administration, 2011, pp. 1-17.

Lovshin, J.A. et al., "Incretin-based therapies for type 2 diabetes mellitus." Nature Reviews Endocrinology, 2009, vol. 5, pp. 262-269.

Lyssenko, V. et al., "Mechanisms by which common variants in the TCF7L2 gene increase risk of type 2 diabetes." The Journal of Clinical Investigation, 2007, vol. 117, No. 8, pp. 2155-2163.

March, J. "Advanced Organic Chemistry: Reactions, Mechanisms, and Structure". Fourth Edition, 1992, pp. 652-653.

Matsumiya, Teruhiko, et al., "Therapeutic Drugs for Clinicians" Diagnosis and Treatment (2008) vol. 96, No. 2 pp. 389-390.

Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.

Mcnay, David E.G. et al., "High fat diet causes rebound weight gain." Molecular Metabolism, 2013, vol. 2, pp. 103-108.

Medline Plus, "Obesity" 2013, Retrieved from internet on Aug. 22, 2013, http://www.nlm.nih.gov/medlineplus/obesity.html.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck Manual of Diagnosis and Therapy: "Obesity." 1999, 17th Edition, Chapter 5, pp. 58-62.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.

Naik, R. et al., "Latent Autoimmune Diabetes in Adults." The Journal of Clinical Endocrinology and Metabolism, 2009, vol. 94, No. 12, pp. 4635-4644.

Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.

National Program for Care Guidelines, "Type 2 Diabetes mellitus." 2002, First Edition, pp. 1-50.

Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.

Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.

Fukushima et al., Drug for Treating Type II Diabetes (6), "Action-mechanism of DPP-IV inhibitor and the availability thereof" Mebio, 2009, vol. 26, No. 8, p. 50-58.

(56) References Cited

OTHER PUBLICATIONS

Gallwitz, B. "Sitagliptin with Metformin: Profile of a Combination for the Treatment of Type 2 Diabetes". Drugs of Today, Oct. 2007, 43(10), p. 681-689.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Gallwitz, B. et al., "Saxagliptin, a dipeptidyl peptidase IV inhibitor for the treatment of type 2 diabetes". IDrugs, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish: p. 828, English: pp. 711-712, Preformulation, Chapter 38.
Gennaro, Alfonso R., Remington Farmacia, 19th Edition, Spanish, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Giron, D.; Thermal Analysis and Calorimetric Methods in the Characterisation of Polymorphs and Solvates; Thermochimica Acta (1995) vol. 248 pp. 1-59.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al, "Insulin Therapy:current alternatives", Arch. Med.Res. 36: p. 258-272 (2005).
Graefe-Mody et al., "The novel DPP-4 inhibitor BI 1356 (proposed tradename ONDERO) and Metformin can be Safely Co-administered Without Dose Adjustment." Poster No. 553-P ADA Jun. 6-10, 2008, San Francisco http://professional.diabetes.org/content/posters/2008/p553-p.pdf.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Greischel, et al., Drug Metabolism and Deposition, "The Dipeptidyl Peptidase-4 Inhibitor Linagliptin Exhibits Time-and Dpse-Dependent Localization in Kidney, Liver, and Intestine after Intravenous Dosing: Results from High Resolution Autoradiography in Rats", 2010, vol. 38, No. 9, p. 1443-1448.
Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct.
2012. <http://www.abstractsonline.com/Plan/ViewAbstract.aspx?sKey=0b0017b9-9e90-4695-b9af-b6870e96a921&cKey=421edb9c-b940-40f0-b282-8e61245561d5&mKey=2dbfcaf7-1539-42d5-8dda-0a94abb089e8>.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Gupta, V. et al., "Choosing a Gliptin." Indian Journal of Endocrinology and Metabolism, 2011, vol. 15, No. 4, pp. 298-308.
Gwaltney, S. "Medicinal Chemistry Approaches to the Inhibition of Dipeptidyl Peptidase IV", Current Topics in Medicinal Chemistry, 2008, 8, p. 1545-1552.
Hainer, Vojtech MD, PHD "Comparative Efficiency and Safety of Pharmacological Approaches to the Management of Obesity." Diabetes Care, 2011, vol. 34, Suppl. 2, pp. S349-S354.
Halimi, S. et al., "Combination treatment in the management of type 2 diabetes: focus on vildagliptin and metformin as a single tablet." Vascular Health and Risk Management, 2008, vol. 4, No. 3, pp. 481-492.
Haluzik, M. et al., "Renal Effects of DPP-4 Inhibitors: A Focus on Microalbuminuria." International Journal of Endocrinology, 2013, vol. 35, No. 6, pp. 1-7.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51.
Hayashi, Michio., "Recipe for Oral Hypoglycemic Agents to Pathological Condition" Pharmacy (2006) vol. 57, No. 9 pp. 2735-2739.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
He, Y.L. et al., "The influence of hepatic imparment on the pharmacokinetics f the dipeptidyl peptidase IV (DPP-4) inhibitor vildagliptin" European Journal of Clinical Pharmacology, vol. 63, No. 7, May 8, 2007, p. 677-686.
Headland, K. et al., "The Effect of Combination Linagliptin and Voglibose on Glucose Control and Body Weight." 73rd Annual Meeting Science Session, ADA, Chicago, Jun. 21, 2013.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.

(56) References Cited

OTHER PUBLICATIONS

Hilfiker, R. et al., "Relevance of Solid-state Properties for Pharmaceutical Products." Polymorphism in the Pharmaceutical Industry, 2006, Chapter 1, pp. 1-19.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemial reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.
Horsford, E. N. "On the source of free hydrochloric acid in the gastric juice." Proceedings of the Royal Society of London, Published in 1868-1869, vol. 17, pp. 391-395.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huettner Silks et al: "BI 1356, a novel and selective xanthine based DPP-IV inhibitor, demonstrates good safety and tolerability with a wide therapeutic window" Diabetes< American Diabetes Association, US, vol. 56, no. Suppl 1, Jun. 1, 2007, p. A156.
Hull, R. et al., "Nephrotic syndrome in adults." British Medical Journal, 2008, vol. 336, pp. 1185-1190.
Nielsen, L, "Incretin Mimetics and DPP-IV Inhibitors for the Treatment of Type 2 Diabetes." DDT, 2005, vol. 10, No. 10, pp. 703-710.
Nihon Ijinpo, Japan Medicinal Journal, 2001, No. 4032, p. 137.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 mailed May 2, 2008.
Patani George A. et al.: "Bioisoterism : A Rational Approach in Drug Design", Chemical Reviews, 1996, vol. 96, No. 8, pp. 3147-3176.
Pearson, E. R. et al., "Variation in TCF7L2 Influences Therapeutic Response to Sulfonylureas." Diabetes, 2007, vol. 56, pp. 2178-2182.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Plummer, C.J.G. et al., "The Effect of Melting Point Distributions on DSC Melting Peaks." Polymer Bulletin, 1996, vol. 36, pp. 355-360.
Pospisilik, et al; Dipeptidyl Peptidase IV Inhibitor Treatment Stimulates ?-Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pratley, R. et al., "Inhibition of DPP-4: a new therapeutic approach for the treatment of type 2 diabetes." Current Medical Research and Opinion, 2007, vol. 23, No. 4, pp. 919-931.
Prescribing Information, Package insert for Leprinton tablets 100mg, Manufacturer: Tatsumi Kagaku Co., Ltd., Mar. 2003, pp. 1-3.
Priimenko, B. A., et al; Synthesis and Pharmacological Activity of Derivates of 6,8-Dimethyl Imidazo(1,2-f) Xanthine—(Russ.); Khimiko-Farmatsevticheskii zhurnal (1984) vol. 18, No. 12 pp. 1456-1461.
Radermecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?" JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Schillinger, M. et al., "Restenosis after percutaneous angioplasty: the role of vascular inflammation." Vascular Health and Risk Management, 2005, vol. 1, No. 1, pp. 73-78.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Shanks, N. et al., Are animal models predictive for humans?, PEHM, Philosophy, Ethics, and Humanaities in Medicine, 4(2), 2009, 1-20.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012. <http://www.abstractsonline.com/Plan/ViewAbstract.aspx?sKey=0b0017b9-9e90-4695-b9af-b6870e96a921&cKey=8eff47ae-db49-4c36-a142-848ac068c405&mKey=2dbfcaf7-1539-42d5-8dda-0a94abb089e8>.
Sheperd, Todd M. et al., "Efective management of obesity." The Journal of Family Practice, 2003, vol. 52, No. 1, pp. 34-42.
Shintani, Maki, et al., "Insulin Resistance and Genes" Circulatory Sciences (1997) vol. 17, No. 12 pp. 1186-1188.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
Shu, L. et al., "Transcription Factor 7-Like 2 Regulates B-Cell Survival and Function in Human Pancreatic Islets." Diabetes, 2008, vol. 57, pp. 645-653.
Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.

(56) References Cited

OTHER PUBLICATIONS

Singhal, D. et al., "Drug polymorphism and dosage form design: a practical perspective." Advanced Drug Delivery Reviews, 2004, vol. 56, pp. 335-347.
Sortino, M.A. et al., "Linagliptin: a thorough characterization beyond its clinical efficacy." Frontiers in Endocrinology, 2013, vol. 4, Article 16, pp. 1-9.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Stahl, P.H., "Handbook of Pharmaceutical Salts" C.G. Wermuth, Wiley-VCH, 2002, pp. 1-374.
Standl, E. et al., "Diabetes and the Heart." Diabetes Guidelines (DDG), 2002, pp. 1-25.
Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.
Suzuki, Y. et al., "Carbon—Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Tadayyon, M. et al., "Insulin sensitisation in the treatment of Type 2 diabetes." Expert Opinion Investigative Drugs, 2003, vol. 12, No. 3, pp. 307-324.
Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.
Takeda Press Release: "Voglibose (BASEN) for the prevention of type 2 diabetes mellitus: A Randomized, Double-blind Trial in Japanese Subjects with Impaired Glucose Tolerance." 2008, Retrieved online Jul. 6, 2015. https://www.takeda.com/news/2008/20080526_3621.html.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Tanaka, S.. et al; "Suppression of Arthritis by the Inhibitors of Dipeptidyl Peptidase IV," In. J. Immunopharmac., vol. 19, No. 1, pp. 15-24, 1997.
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession No. RN 668270-12-01, 2004, "1H-Purine-2,6-dione, 8- [(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Cheon, et al., Biochemical Pharmacology, "Inhibition of dipeptidyl IV by novel inhibitors with pyrazolidine scaffold", 2005, vol. 70, p. 22-29.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Clinical Trial NCT00622284 (published online at clinicaltrials.gov on Feb. 22, 2008).
Clinical Trials, No. NCT00309608, "Efficacy and Safety of BI 1356 BS in Combination with Metformin in Patients With type2 Diabetes" 2009, pp. 1-3.
Clinical Trials, No. NCT00622284, "Efficacy and Safety of BI 1356 in combination with metformin in patients with type 2 diabetes" 2012, pp. 1-5.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCTO0601250/2008_01_25 [retrieved on Feb. 27, 2009].
Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.
Clinical Trials: NCT00798161. "Safety and efficacy of BI 1356 Plus Metformin in Type 2 Diabetes, Factorial Design". Clinical Trials.gov archive. A Service of the U.S> National Institutes of Health. Nov. 24, 2008, p. 1-3. http://clinicaltrials.gov/archive/NCT00798161/2008_11_24.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al., "Mice lacking dipeptidyl peptidase IV are protected against obesity and insulin resistance". PNAS, May 27, 2003, vol. 100, No. 11, p. 6825-6830.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Cotton, M.L. et al., "L-649,923—The selection of an appropriate salt form and preparation of a stable oral formulation." International Journal of Pharmaceutics, 1994, vol. 109, Issue 3, pp. 237-249.
Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.
Crowe, E. et al., "Early identification and management of chronic kidney disease: summary of NICE guidance." British Medical Journal, 2008, vol. 337, pp. 812-815.
Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X, Nov. 1980, p. 1497-1500.
Dave, Rutesh H. "Overview of pharmaceutical excipients used in tablets and capsules." Drug Topics, Oct. 24, 2008.

(56) References Cited

OTHER PUBLICATIONS

Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

Deacon, C.F., et al. Inhibitors of dipeptidyl peptidase IV: a novel approach for the prevention and treatment of Type 2 diabetes? Expert Opinion on Investigational Drugs, Sep. 2004, vol. 13, No. 9, p. 1091-1102.

Definition of "prevent", e-dictionary, Aug. 15, 2013, http://dictionary.reference.com/browse/prevent.

DeMeester, I. et al.; "CD26, let it cut or cut it down", Review: Immunology Today; Aug. 1999, vol. 20, No. 8 pp. 367-375.

Demuth, H-U. et al., "Type 2 diabetes—Therapy with dipeptidyl peptidase IV inhibitors". Biochimica et Biophysica Acta, vol. 1751(1), 2005, p. 33-44.

Diabetes Frontier, 2007, vol. 18, No. 2, p. 145-148.

Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.

Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www.diabetesincontrol.com/articles/53-diabetes-news/5145.

Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

Drucker, Daniel J., "Dipeptidyl Peptidase-4 Inhibition and the Treatment of Type 2 Diabetes." Diabetes Care, 2007, vol. 30, No. 6, pp. 1335-1343.

Drucker, et al.., The incretin system:glucagon-like peptide-1 receptor agonists and dipeptidyl peptidase-4 inhibitors in type 2 diabetes. Lancet, 2006, 368: 1696-705.

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Dunitz, J. et al., "Disappearing Polymorphs." Acc. Chem. Res. 1995, vol. 28, No. 4, pp. 193-200.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.

Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

Eucreas Scientific Discussion, 2007, p. 1-27, www.emea.europa.eu/humandocs/PD/Fs/EPAR/eucreas/H-807-en6.pdf, Anonymous.

Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.

Ferry, Robert Jr., "Diabetes Causes." eMedicine Health, MedicineNet.com, 2013, Retrieved from internet on Aug. 22, 2013,<http://www.onhealth.com/diabetes_health/page3.htm#diabetes_causes>.

Florez, J. et al. "TCF7L2 Polymorphisms and Progression to Diabetes in the Diabetes Prevention Program." The New England Journal of Medicine, 2006, vol. 355, No. 3, pp. 241-250.

Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.

Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.

Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.

Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.

Third Party Observation for application No. EP20070728655, May 13, 2013.

Thomas, L, et al: "BI 1356, a novel and selective xanthine beased DPP-IV inhibitor, exhibits a superior profile when compared to sitagliptin and vildagliptin." Diabetologoa, vol. 50, no. Suppl. 1, Sep. 2007, p. S363.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors." Journal of Pharmacology and Experimental Therapeutics, 2008, vol. 325, No. 1, pp. 175-182.

Thornber, C.W., "Isosterism and Molecular Modification in Drug Design." Chemical Society Reviews, 1979, pp. 563-580.

Tounyoubyou, "Symposium-19: Future Perspectives on Incretion Therapy in Diabetes." 2008, vol. 51, Suppl. 1, p. S-71, S19-2.

Tradjenta, Highlights of Prescribing Information (revised Sep. 2012).

Tribulova, N. et al. "Chronic Disturbances in NO Production Results in Histochemical and Subcellular Alterations of the Rat Heart." Physiol. Res., 2000, vol. 49, No. 1, pp. 77-88.

Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.

Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013. <http://www.abstractsonline.com/Plan/ViewAbstract.aspx?sKey=e68ac573- fe45-4c2f-9485-6270854fc10b&cKey=3c387569-04de-4f8c-b025-b358df91ca64&mKey=%7b89918D6D-3018-4EA9-9D4F-711F98A7AE5D%7d>.

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

(56) References Cited

OTHER PUBLICATIONS

United Healthcare, "Diabetes." Retrieved from internet on Aug. 22, 2013, http://www.uhc.com/source4women/health_topics/diabetesirelatedinformation/dOf0417b073bf11OVgnVCM1000002f1Ob1Oa__.htm.

Vichayanrat, A. et al., "Efficacy and safety of voglibose in comparison with acarbose in type 2 diabetic patients." Diabetes Research and Clinical Practice, 2002, vol. 55, pp. 99-103.

Vickers, 71st Scientific Session of the American Diabetes Association, "The DPP-4 inhibitor linagliptin is weight neutral in the DIO rat but inhibits the weight gain of DIO animals withdrawn from exenatide", vol. 60, Jul. 2011.

Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

Wertheimer, et al., "Drug Delivery Systems improve pharmaceutical profile and faciliate medication adherence", Adv. Therapy 22: p. 559-577 (2005).

White, John R. Jr., "Dipeptidyl Peptidase-IV Inhibitors: Phamacological Profile and Clinical Use". Clinical Diabetes, Apr. 2008, vol. 26, No. 2, pp. 53-57.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.

Wolff, M.E.: "Burger's Medicinal Chemistry and Drug Discovery" Fifth Edition, vol. 1: Principles and Practice, pp. 975-977, 1994, John Wiley & Sons, Inc.

World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.

X-Ray Diffraction. The United States Pharmacopeia, 2002, USP 25 NF20, p. 2088-2089.

Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.

Yasuda, et al. "E3024 3-but-2-ynyl-5-methyl-2-piperazin-1-yl-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.

Yoshikawa, Seiji et al.: Chemical Abstract of Japanese Patent No. WO 2003/104229 Preparation of purinone derivatives as dipeptidylpeptidase IV (DPP-IV) inhibitors, 2003.

Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.

Zejc, Alfred, et al; "Badania Nad Piperazynowymi Pochodnymi Dwumetyloksantyn" Acta Polon Pharm, XXXV (1976) No. 4 pp. 417-421.

Zhimei, Xiao et al., "Study progression of oral drugs for treatment of type II diabetes." Drug Evaluation, 2004, vol. 1, No. 2, pp. 138-143.

Zhong, Qing et al; "Glucose-dependent insulinotropic peptide stimulates proliferation and TGF-? release from MG-63 cells," Peptides 24 (2003) 611-616.

Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.

Zimdahl, H. et al., "Influence of TCF7L2 gene variants on the therapeutic response to the dipeptidylpeptidase-4 inhibitor linagliptin." Diabetologia, 2014, vol. 57, pp. 1869-1875.

Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.

* cited by examiner

8-[3-AMINO-PIPERIDIN-1-YL]-XANTHINES, THE PREPARATION THEREOF AND THEIR USE AS PHARMACEUTICAL COMPOSITIONS

APPLICATION DATA

This application is a continuation of U.S. application Ser. No. 14/154,885, filed Jan. 14, 2014, which is a continuation of U.S. Ser. No. 13/448,495, filed Apr. 17,2012, which is a continuation of U.S. application Ser. No. 12/143,128, filed Jun. 20, 2008, which is a continuation of U.S. application Ser. No. 10/639,036, filed, Aug. 12, 2003. This application claims the benefit of US provisional application Ser. Nos. 60/409,312, filed Sep. 9, 2002 and 60/461,752, filed Apr. 10, 2003, and German application Nos. DE 102 38 243.3, filed Aug. 21, 2002 and DE 103 12 353.9, filed Mar. 20, 2003.

FIELD OF INVENTION

The present invention relates to compounds having valuable pharmacological properties, particularly an inhibiting effect on the activity of the enzyme dipeptidylpeptidase-IV (DPP-IV).

DETAILED DESCRIPTION OF THE INVENTION

The present invention relates to new substituted xanthines of general formula

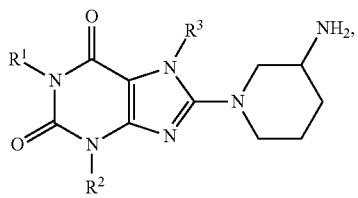

(I)

the tautomers, the stereoisomers, the mixtures, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

In the above formula I
$R^1$ denotes a methyl group,
a methyl group which is substituted by a dimethylaminocarbonyl, pyrrolidin-1-ylcarbonyl, piperidin-1-ylcarbonyl, tert.-butylcarbonyl or a cyclohexylcarbonyl-group,
a methyl group which is substituted by a naphthyl, methylnaphthyl, methoxynaphthyl, nitronaphthyl or dimethylaminonaphthyl group,
a methyl group which is substituted by a 2-phenylethenyl or a biphenylyl group,
a methyl group which is substituted by a phenyloxadiazolyl, 5-methyl-3-phenyl-isoxazolyl, phenylpyridinyl, indolyl, benzothiophenyl, quinolinyl, isoquinolinyl, methyliso-quinolinyl, (methoxycarbonylmethylamino)-isoquinolinyl, cinnolinyl, quinazolinyl, methylquinazolinyl, 1,2-dihydro-1-methyl-2-oxo-quinolinyl, 1,2-dihydro-2-methyl-1-oxo-isoquinolinyl, 3,4-dihydro-4-oxo-phthalazinyl, 3,4-dihydro-3-methyl-4-oxo-phthalazinyl, 3,4-dihydro-4-oxo-quinazolinyl, 3,4-dihydro-3-methyl-4-oxo-quinazolinyl or a 2-oxo-2H-chromenyl group,
a 2-methoxyethyl, 2-phenyloxyethyl or 2-cyanoethyl group,
a phenylcarbonylmethyl or a 1-(phenylcarbonyl)-ethyl group,
a phenylcarbonylmethyl group wherein the phenyl moiety is substituted by an amino, cyanomethylamino, methylcarbonylamino, ethylcarbonylamino, isopropylcarbonylamino, methoxycarbonylamino, (ethyloxycarbonylamino)-carbonylamino or a 2-oxo-imidazolidin-1-yl group,
a phenylcarbonylmethyl group wherein the phenyl moiety is substituted by a carboxy, methoxycarbonyl, ethyloxycarbonyl, aminocarbonyl, methylaminocarbonyl, dimethylaminocarbonyl or morpholin-4-ylcarbonyl group,
a phenylcarbonylmethyl group wherein the phenyl moiety is substituted by a methylsulphanyl, methylsulphinyl or methylsulphonyl group,
a phenylcarbonylmethyl group wherein the phenyl moiety is substituted by a carboxymethoxy, ethyloxycarbonylmethoxy, isopropyloxycarbonylmethoxy, aminocarbonylmethoxy, methylaminocarbonylmethoxy, ethylaminocarbonylmethoxy, isopropylaminocarbonylmethoxy, dimethylaminocarbonylmethoxy, pyrrolidin-1-ylcarbonylmethoxy or morpholin-4-ylcarbonylmethoxy group,
a phenylcarbonylmethyl group wherein the phenyl moiety is substituted by a 1-(methoxycarbonyl)-ethyloxy or a 1-(aminocarbonyl)-ethyloxy group,
a phenylcarbonylmethyl group wherein the phenyl moiety is substituted by a methylsulphinylmethoxy group,
a phenylcarbonylmethyl group wherein the phenyl moiety is substituted by two methoxy groups, or
a phenylcarbonylmethyl group wherein in the phenyl moiety two adjacent hydrogen atoms are replaced by a —O—CH$_2$—O—, —O—CH$_2$—CH$_2$—O or a —N(CH$_3$)—CO—O group,
$R^2$ denotes a hydrogen atom,
a methyl, isopropyl, 2-propen-1-yl, 2-propyn-1-yl, or phenyl group or
a cyanomethyl or methoxycarbonylmethyl group and
$R^3$ denotes a 2-cyanobenzyl or 2,6-dicyanobenzyl group,
a 2-methyl-2-propen-1-yl, 2-chloro-2-propen-1-yl or 3-bromo-2-propen-1-yl group
a 2-buten-1-yl, 3-methyl-2-buten-1-yl or 2,3-dimethyl-2-buten-1-yl group,
a 2-butyn-1-yl group,
a 1-cyclopenten-1-ylmethyl group or
a 2-furanylmethyl group.

The carboxy groups mentioned in the definition of the above mentioned groups may be replaced by a group which can be converted into a carboxy group in vivo or by a group which is negatively charged under physiological conditions,
and furthermore the amino and imino groups mentioned in the definition of the above mentioned groups may be substituted by a group which can be cleaved in vivo. Such groups are described for example in WO 98/46576 and by N. M. Nielsen et al. in International Journal of Pharmaceutics 39, 75-85 (1987).

Compounds which contain a group that can be cleaved in vivo are prodrugs of the corresponding compounds wherein this group that can be cleaved in vivo has been cleaved.

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkyloxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

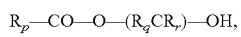

wherein
$R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group,
$R_q$ denotes a hydrogen atom, a $C_{1-3}$-alkyl, $C_{5-7}$-cycloalkyl or phenyl group and
$R_r$ denotes a hydrogen atom or a $C_{1-3}$-alkyl group,
by a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkoxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkoxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_p$—CO—O—($R_qCR_r$)—O—CO, $C_{1-6}$-alkyl-CO—NH—($R_sCR_t$)—O—CO— or $C_{1-6}$-alkyl-CO—O—($R_sCR_t$)—($R_sCR_t$)—O—CO— group, wherein $R_p$ to $R_r$ are as hereinbefore defined, $R_s$ and $R_t$, which may be identical or different, denote hydrogen atoms or $C_{1-3}$-alkyl groups.

A first object of the invention relates to compounds of general formula (I) wherein
$R^1$ denotes a methyl group which is substituted by a dimethylaminocarbonyl, pyrrolidin-1-ylcarbonyl, piperidin-1-ylcarbonyl, tert.-butylcarbonyl or a cyclohexylcarbonyl group,
a methyl group which is substituted by a naphthyl, methylnaphthyl, methoxynaphthyl, nitronaphthyl or (dimethylamino)-naphthyl group,
a methyl group which is substituted by a 2-phenylethenyl or a biphenylyl group,
a methyl group which is substituted by a phenyl-oxadiazolyl, 5-methyl-3-phenyl-isoxazolyl, phenyl-pyridinyl, indolyl, benzothiophenyl, quinolinyl, isoquinolinyl, methylisoquinolinyl, (methoxycarbonylmethylamino)-isoquinolinyl, cinnolinyl, quinazolinyl, methylquinazolinyl, 1,2-dihydro-1-methyl-2-oxo-quinolinyl, 1,2-dihydro-2-methyl-1-oxo-isoquinolinyl, 3,4-dihydro-4-oxo-phthalazinyl, 3,4-dihydro-3-methyl-4-oxo-phthalazinyl, 3,4-dihydro-4-oxo-quinazolinyl, 3,4-dihydro-3-methyl-4-oxo-quinazolinyl or a 2-oxo-2H-chromenyl group,
a 2-methoxyethyl, 2-phenyloxyethyl or 2-cyanoethyl group,
a phenylcarbonylmethyl or a 1-(phenylcarbonyl)-ethyl group,
a phenylcarbonylmethyl group wherein the phenyl moiety is substituted by an amino, cyanomethylamino, methylcarbonylamino, ethylcarbonylamino, isopropylcarbonylamino, methoxycarbonylamino, (ethyloxycarbonylamino)-carbonylamino or a 2-oxo-imidazolidin-1-yl group,
a phenylcarbonylmethyl group wherein the phenyl moiety is substituted by a carboxy, methoxycarbonyl, ethyloxycarbonyl, aminocarbonyl, methylaminocarbonyl, dimethylaminocarbonyl or morpholin-4-ylcarbonyl group,
a phenylcarbonylmethyl group wherein the phenyl moiety is substituted by a methylsulphanyl, methylsulphinyl or methylsulphonyl group,
a phenylcarbonylmethyl group wherein the phenyl moiety is substituted by a carboxymethoxy, ethyloxycarbonylmethoxy, isopropyloxycarbonylmethoxy, aminocarbonylmethoxy, methylaminocarbonylmethoxy, ethylaminocarbonylmethoxy, isopropylaminocarbonylmethoxy, dimethylaminocarbonylmethoxy, pyrrolidin-1-ylcarbonylmethoxy or morpholin-4-ylcarbonylmethoxy group,
a phenylcarbonylmethyl group wherein the phenyl moiety is substituted by a 1-(methoxycarbonyl)-ethyloxy or a 1-(aminocarbonyl)-ethyloxy group,
a phenylcarbonylmethyl group wherein the phenyl moiety is substituted by a methylsulphinylmethoxy group,
a phenylcarbonylmethyl group wherein the phenyl moiety is substituted by two methoxy groups or
a phenylcarbonylmethyl group wherein in the phenyl moiety two adjacent hydrogen atoms are replaced by a —O—CH$_2$—O, —O—CH$_2$—CH$_2$—O or a —N(CH$_3$)—CO—O group,
$R^2$ denotes a methyl, isopropyl or phenyl group and
$R^3$ denotes a 2-methyl-2-propen-1-yl, 2-chloro-2-propen-1-yl or 3-bromo-2-propen-1-yl group a 2-buten-1-yl or 2,3-dimethyl-2-buten-1-yl group,
a 2-butyn-1-yl group,
a 1-cyclopenten-1-ylmethyl group or
a 2-furanylmethyl group,
as well as the compounds
1-(2-cyano-ethyl)-3-methyl-7-(2-cyano-benzyl)-8-(3-amino-piperidin-1-yl)-xanthine,
1-(2-{2-[(ethoxycarbonyl)methoxy]-phenyl}-2-oxo-ethyl)-3-methyl-7-(3-methyl-2-buten-1-yl)-8-(3-amino-piperidin-1-yl)-xanthine,
1-(2-{2-[(aminocarbonyl)methoxy]-phenyl}-2-oxo-ethyl)-3-methyl-7-(3-methyl-2-buten-1-yl)-8-(3-amino-piperidin-1-yl)-xanthine,
1-(2-{3-[(methanesulphinyl)methoxy]-phenyl}-2-oxo-ethyl)-3-methyl-7-(3-methyl-2-buten-1-yl)-8-(3-amino-piperidin-1-yl)-xanthine,
1-(1-methyl-2-oxo-2-phenyl-ethyl)-3-methyl-7-(3-methyl-2-buten-1-yl)-8-(3-amino-piperidin-1-yl)-xanthine,
1-(2-phenoxy-ethyl)-3-methyl-7-(2-cyano-benzyl)-8-(3-amino-piperidin-1-yl)-xanthine,
1-(2-phenyl-2-oxo-ethyl)-7-(3-methyl-2-buten-1-yl)-8-(3-amino-piperidin-1-yl)-xanthine,
1-(2-{3-[(ethoxycarbonyl)methoxy]-phenyl}-2-oxo-ethyl)-3-methyl-7-(3-methyl-2-buten-1-yl)-8-(3-amino-piperidin-1-yl)-xanthine,
1-(2-{2-[(methylaminocarbonyl)methoxy]-phenyl}-2-oxo-ethyl)-3-methyl-7-(3-methyl-2-buten-1-yl)-8-(3-amino-piperidin-1-yl)-xanthine,
1-(2-{2-[(dimethylaminocarbonyl)methoxy]-phenyl}-2-oxo-ethyl)-3-methyl-7-(3-methyl-2-buten-1-yl)-8-(3-amino-piperidin-1-yl)-xanthine,
1-(2-methoxy-ethyl)-3-methyl-7-(2-cyano-benzyl)-8-(3-amino-piperidin-1-yl)-xanthine,
1-methyl-3-[(methoxycarbonyl)methyl]-7-(2-cyano-benzyl)-8-(3-amino-piperidin-1-yl)-xanthine,
1-methyl-3-cyanomethyl-7-(2-cyano-benzyl)-8-(3-amino-piperidin-1-yl)-xanthine,
1-methyl-3-(2-propyn-1-yl)-7-(2-cyano-benzyl)-8-(3-amino-piperidin-1-yl)-xanthine,
1-{2-[3-(2-oxo-imidazolidin-1-yl)-phenyl]-2-oxo-ethyl}-3-methyl-7-(3-methyl-2-buten-1-yl)-8-(3-amino-piperidin-1-yl)-xanthine,
1-methyl-3-(2-propen-1-yl)-7-(2-cyano-benzyl)-8-(3-amino-piperidin-1-yl)-xanthine,
1-(2-{2-[(ethylcarbonyl)amino]-phenyl}-2-oxo-ethyl)-3-methyl-7-(3-methyl-2-buten-1-yl)-8-(3-amino-piperidin-1-yl)-xanthine,
1-methyl-3-phenyl-7-(2-cyano-benzyl)-8-(3-amino-piperidin-1-yl)-xanthine,
1-[2-(2-amino-phenyl)-2-oxo-ethyl]-3-methyl-7-(3-methyl-2-buten-1-yl)-8-((S)-3-amino-piperidin-1-yl)-xanthine,
1-(2-phenyl-2-oxo-ethyl)-3-cyanomethyl-7-(3-methyl-2-buten-1-yl)-8-(3-amino-piperidin-1-yl)-xanthine,
1-[(quinolin-2-yl)methyl]-3-methyl-7-(3-methyl-2-buten-1-yl)-8-(3-amino-piperidin-1-yl)-xanthine,
1-[(2-oxo-2H-chromen-4-yl)methyl]-3-methyl-7-(3-methyl-2-buten-1-yl)-8-(3-amino-piperidin-1-yl)-xanthine,
1-[(cinnolin-4-yl)methyl]-3-methyl-7-(3-methyl-2-buten-1-yl)-8-(3-amino-piperidin-1-yl)-xanthine,
1-[(1-methyl-2-oxo-1,2-dihydro-quinolin-4-yl)methyl]-3-methyl-7-(3-methyl-2-buten-1-yl)-8-(3-amino-piperidin-1-yl)-xanthine,
1-[(4-oxo-3,4-dihydro-phthalazin-1-yl)methyl]-3-methyl-7-(3-methyl-2-buten-1-yl)-8-(3-amino-piperidin-1-yl)-xanthine,
1-[(quinazolin-4-yl)methyl]-3-methyl-7-(3-methyl-2-buten-1-yl)-8-(3-amino-piperidin-1-yl)-xanthine,
1-[(5-methyl-3-phenyl-isoxazol-4-yl)methyl]-3-methyl-7-(3-methyl-2-buten-1-yl)-8-(3-amino-piperidin-1-yl)-xanthine,
1-[(isoquinolin-3-yl)methyl]-3-methyl-7-(3-methyl-2-buten-1-yl)-8-(3-amino-piperidin-1-yl)-xanthine,
1-[(3-phenyl-[1,2,4]oxadiazol-5-yl)methyl]-3-methyl-7-(3-methyl-2-buten-1-yl)-8-(3-amino-piperidin-1-yl)-xanthine,
1-[(4-phenyl-pyridin-2-yl)methyl]-3-methyl-7-(3-methyl-2-buten-1-yl)-8-(3-amino-piperidin-1-yl)-xanthine,
1-[(5-phenyl-pyridin-2-yl)methyl]-3-methyl-7-(3-methyl-2-buten-1-yl)-8-(3-amino-piperidin-1-yl)-xanthine,
1-[(3-methyl-4-oxo-3,4-dihydro-phthalazin-1-yl)methyl]-3-methyl-7-(3-methyl-2-buten-1-yl)-8-(3-amino-piperidin-1-yl)-xanthine,
1-[2-(3-methylsulphanyl-phenyl)-2-oxo-ethyl]-3-methyl-7-(3-methyl-2-buten-1-yl)-8-(3-amino-piperidin-1-yl)-xanthine,
1-[2-(3-methanesulphinyl-phenyl)-2-oxo-ethyl]-3-methyl-7-(3-methyl-2-buten-1-yl)-8-(3-amino-piperidin-1-yl)-xanthine,
1-[2-(3-methanesulphonyl-phenyl)-2-oxo-ethyl]-3-methyl-7-(3-methyl-2-buten-1-yl)-8-(3-amino-piperidin-1-yl)-xanthine,
1-[2-(3-carboxy-phenyl)-2-oxo-ethyl]-3-methyl-7-(3-methyl-2-buten-1-yl)-8-(3-amino-piperidin-1-yl)-xanthine,
1-[2-(3-methoxycarbonyl-phenyl)-2-oxo-ethyl]-3-methyl-7-(3-methyl-2-buten-1-yl)-8-(3-amino-piperidin-1-yl)-xanthine,
1-{2-[3-(methylaminocarbonyl)-phenyl]-2-oxo-ethyl}-3-methyl-7-(3-methyl-2-buten-1-yl)-8-(3-amino-piperidin-1-yl)-xanthine,
1-{2-[3-(dimethylaminocarbonyl)-phenyl]-2-oxo-ethyl}-3-methyl-7-(3-methyl-2-buten-1-yl)-8-(3-amino-piperidin-1-yl)-xanthine,
1-{2-[3-(morpholin-4-yl-carbonyl)-phenyl]-2-oxo-ethyl}-3-methyl-7-(3-methyl-2-buten-1-yl)-8-(3-amino-piperidin-1-yl)-xanthine,
1-[2-(2-carboxy-phenyl)-2-oxo-ethyl]-3-methyl-7-(3-methyl-2-buten-1-yl)-8-(3-amino-piperidin-1-yl)-xanthine,
1-[2-(2-ethoxycarbonyl-phenyl)-2-oxo-ethyl]-3-methyl-7-(3-methyl-2-buten-1-yl)-8-(3-amino-piperidin-1-yl)-xanthine,
1-{2-[2-(dimethylaminocarbonyl)-phenyl]-2-oxo-ethyl}-3-methyl-7-(3-methyl-2-buten-1-yl)-8-(3-amino-piperidin-1-yl)-xanthine,
1-{2-[2-(morpholin-4-yl-carbonyl)-phenyl]-2-oxo-ethyl}-3-methyl-7-(3-methyl-2-buten-1-yl)-8-(3-amino-piperidin-1-yl)-xanthine,
1-[2-(2,6-dimethoxy-phenyl)-2-oxo-ethyl]-3-methyl-7-(3-methyl-2-buten-1-yl)-8-(3-amino-piperidin-1-yl)-xanthine,
1-((E)-3-phenyl-allyl)-3-methyl-7-(3-methyl-2-buten-1-yl)-8-(3-amino-piperidin-1-yl)-xanthine,
1-[(benzo[b]thiophen-3-yl)methyl]-3-methyl-7-(3-methyl-2-buten-1-yl)-8-(3-amino-piperidin-1-yl)-xanthine,
1-[(1H-indol-3-yl)methyl]-3-methyl-7-(3-methyl-2-buten-1-yl)-8-(3-amino-piperidin-1-yl)-xanthine,
1-[(biphenyl-4-yl)methyl]-3-methyl-7-(3-methyl-2-buten-1-yl)-8-(3-amino-piperidin-1-yl)-xanthine,
1-(2-cyclohexyl-2-oxo-ethyl)-3-methyl-7-(3-methyl-2-buten-1-yl)-8-(3-amino-piperidin-1-yl)-xanthine,
1-(3,3-dimethyl-2-oxo-butyl)-3-methyl-7-(3-methyl-2-buten-1-yl)-8-(3-amino-piperidin-1-yl)-xanthine,
1-({5-[(methoxycarbonyl)methylamino]-isoquinolin-1-yl}methyl)-3-methyl-7-(3-methyl-2-buten-1-yl)-8-(3-amino-piperidin-1-yl)-xanthine, 1-(2-dimethylamino-2-oxo-ethyl)-3-methyl-7-(3-methyl-2-buten-1-yl)-8-(3-amino-piperidin-1-yl)-xanthine,
1-[2-(piperidin-1-yl)-2-oxo-ethyl]-3-methyl-7-(3-methyl-2-buten-1-yl)-8-(3-amino-piperidin-1-yl)-xanthine,
1-[(2-methyl-1-oxo-1,2-dihydro-isoquinolin-4-yl)methyl]-7-(3-methyl-2-buten-1-yl)-8-(3-amino-piperidin-1-yl)-xanthine,
1-[2-(2,3-dimethoxy-phenyl)-2-oxo-ethyl]-3-methyl-7-(3-methyl-2-buten-1-yl)-8-(3-amino-piperidin-1-yl)-xanthine,
1-[2-(pyrrolidin-1-yl)-2-oxo-ethyl]-3-methyl-7-(3-methyl-2-buten-1-yl)-8-(3-amino-piperidin-1-yl)-xanthine,
1-[2-(2,3-dihydro-benzo[1,4]dioxin-5-yl)-2-oxo-ethyl]-3-methyl-7-(3-methyl-2-buten-1-yl)-8-(3-amino-piperidin-1-yl)-xanthine,
1-[2-(3-methyl-2-oxo-2,3-dihydro-benzooxazol-7-yl)-2-oxo-ethyl]-3-methyl-7-(3-methyl-2-buten-1-yl)-8-(3-amino-piperidin-1-yl)-xanthine,
1-[2-(benzo[1,3]dioxol-4-yl)-2-oxo-ethyl]-3-methyl-7-(3-methyl-2-buten-1-yl)-8-(3-amino-piperidin-1-yl)-xanthine,
1-methyl-3-isopropyl-7-(2-cyano-benzyl)-8-(3-amino-piperidin-1-yl)-xanthine,
1-[2-(2-cyanomethylamino-phenyl)-2-oxo-ethyl]-3-methyl-7-(3-methyl-2-buten-1-yl)-8-(3-amino-piperidin-1-yl)-xanthine,
1-[(isoquinolin-1-yl)methyl]-3-[(methoxycarbonyl)methyl]-7-(3-methyl-2-buten-1-yl)-8-(3-amino-piperidin-1-yl)-xanthine,
1-(2-{2-[(isopropyloxycarbonyl)methoxy]-phenyl}-2-oxo-ethyl)-3-methyl-7-(3-methyl-2-buten-1-yl)-8-(3-amino-piperidin-1-yl)-xanthine,
1-[2-(2-{[(ethoxycarbonylamino)carbonyl]amino}-phenyl)-2-oxo-ethyl]-3-methyl-7-(3-methyl-2-buten-1-yl)-8-(3-amino-piperidin-1-yl)-xanthine,
1-[2-(2-acetylamino-phenyl)-2-oxo-ethyl]-3-methyl-7-(3-methyl-2-buten-1-yl)-8-((S)-3-amino-piperidin-1-yl)-xanthine,
1-(2-{2-[(methylaminocarbonyl)methoxy]-phenyl}-2-oxo-ethyl)-3-methyl-7-(3-methyl-2-buten-1-yl)-8-((S)-3-amino-piperidin-1-yl)-xanthine,
1-methyl-7-(2-cyano-benzyl)-8-(3-amino-piperidin-1-yl)-xanthine,
1-(2-{2-[(isopropylcarbonyl)amino]-phenyl}-2-oxo-ethyl)-3-methyl-7-(3-methyl-2-buten-1-yl)-8-(3-amino-piperidin-1-yl)-xanthine,
1-(2-{2-[(methoxycarbonyl)amino]-phenyl}-2-oxo-ethyl)-3-methyl-7-(3-methyl-2-buten-1-yl)-8-(3-amino-piperidin-1-yl)-xanthine,
1-[2-(3-methyl-2-oxo-2,3-dihydro-benzooxazol-4-yl)-2-oxo-ethyl]-3-methyl-7-(3-methyl-2-buten-1-yl)-8-(3-amino-piperidin-1-yl)-xanthine,
1-[2-(2-nitro-3-methoxy-phenyl)-2-oxo-ethyl]-3-methyl-7-(3-methyl-2-buten-1-yl)-8-(3-amino-piperidin-1-yl)-xanthine,
1-[2-(2-amino-3-methoxy-phenyl)-2-oxo-ethyl]-3-methyl-7-(3-methyl-2-buten-1-yl)-8-(3-amino-piperidin-1-yl)-xanthine,
1-[2-(2-oxo-2,3-dihydro-benzooxazol-7-yl)-2-oxo-ethyl]-3-methyl-7-(3-methyl-2-buten-1-yl)-8-(3-amino-piperidin-1-yl)-xanthine,
1-[(3-methyl-isoquinolin-1-yl)methyl]-3-methyl-7-(3-methyl-1-buten-1-yl)-8-((R)-3-amino-piperidin-1-yl)-xanthine,
1-[(3-methyl-isoquinolin-1-yl)methyl]-3-methyl-7-(2-cyano-benzyl)-8-(3-amino-piperidin-1-yl)-xanthine,
1-[2-(3-carboxymethoxy-phenyl)-2-oxo-ethyl]-3-methyl-7-(3-methyl-2-buten-1-yl)-8-(3-amino-piperidin-1-yl)-xanthine and
1-[2-(2-carboxymethoxy-phenyl)-2-oxo-ethyl]-3-methyl-7-(3-methyl-2-buten-1-yl)-8-(3-amino-piperidin-1-yl)-xanthine,
the tautomers, enantiomers, diastereomers, the mixtures thereof, the prodrugs thereof and the salts thereof.

A first preferred sub-group of the first object of the invention comprises compounds of general formula I wherein
$R^1$ denotes a 4-methoxy-1-naphthylmethyl group,
a 2-quinolinylmethyl, 4-quinolinylmethyl or a 6-quinolinylmethyl group,
a 1-isoquinolinylmethyl, 3-methyl-1-isoquinolinylmethyl, 4-methyl-1-isoquinolinylmethyl or a 3-isoquinolinylmethyl group or
a 2-quinazolinylmethyl, 4-methyl-2-quinazolinylmethyl or a 4-quinazolinyl-methyl group,
$R^2$ denotes a methyl group and
$R^3$ denotes a 2-buten-1-yl or a 2-butyn-1-yl group,
the tautomers, enantiomers, diastereomers, the mixtures thereof and the salts thereof.

A second preferred sub-group of the first object of the invention comprises compounds of general formula I, wherein
$R^1$ denotes a [2-(methylcarbonylamino)-phenyl]-carbonylmethyl group,
a [2-(ethylcarbonylamino)-phenyl]-carbonylmethyl group or a [2-(isopropylcarbonylamino)-phenyl]-carbonylmethyl group,
$R^2$ denotes a methyl group and
$R^3$ denotes a 2-buten-1-yl or a 2-butyn-1-yl group,
the tautomers, enantiomers, diastereomers, the mixtures thereof and the salts thereof.

A third preferred sub-group of the first object of the invention comprises compounds of general formula I, wherein
$R^1$ denotes a [2-(aminocarbonylmethoxy)-phenyl]-carbonylmethyl group,
[2-(methylaminocarbonylmethoxy)-phenyl]-carbonyl methyl group,
a [2-(ethylaminocarbonylmethoxy)-phenyl]-carbonylmethyl group or
a [2-(isopropylaminocarbonylmethoxy)-phenyl]-carbonylmethyl group,
$R^2$ denotes a methyl group and
$R^3$ denotes a 2-buten-1-yl group,
a 2-butyn-1-yl group or
a 1-cyclopenten-1-ylmethyl group,
the tautomers, enantiomers, diastereomers, the mixtures thereof and the salts thereof.

A second object of the invention relates to compounds of general formula I, wherein
$R^1$ denotes a methyl group which is substituted by a naphthyl, fluoronaphthyl, methylnaphthyl, methoxynaphthyl, (difluoromethoxy)-naphthyl, cyanonaphthyl, nitronaphthyl or (dimethylamino)-naphthyl group,
a methyl group which is substituted by a phenanthrenyl group, a methyl group which is substituted by a 2-phenylethenyl, 2-[(trifluoromethyl)-phenyl]-ethenyl, 2-(nitrophenyl)ethenyl, 2-(pentafluorophenyl)ethenyl or a biphenylyl group,
a methyl group which is substituted by a phenyloxadiazolyl, phenylpyridinyl, indolyl, methylindolyl, dimethyl-6,7-dihydro-5H-[2]pyrindinyl, benzimidazolyl, methylbenzimidazolyl, (cyanoethyl)-benzimidazolyl, (methylaminocarbonylmethyl)benzimidazolyl, benzylbenzimidazolyl, benzofuranyl, acetylbenzofuranyl, cyanobenzofuranyl, benzoxazolyl, nitrobenzoxazolyl, benzothiophenyl, methylbenzothiazolyl, quinolinyl, methoxyquinolinyl, isoquinolinyl, methylisoquinolinyl, (difluoromethyl)-isoquinolinyl, (trifluoromethyl)-isoquinolinyl, dimethylisoquinolinyl, (1-cyano-1-methyl-ethyl)isoquinolinyl, phenylisoquinolinyl, methoxyisoquinolinyl, methoxy-chloro-isoquinolinyl, methoxy-bromo-isoquinolinyl, (methoxycarbonylmethylamino)-isoquinolinyl, dimethyl-5,6,7,8-tetrahydroisoquinolinyl, 1,2,3,4-tetrahydro-phenanthridinyl, cinnolinyl, quinazolinyl, methylquinazolinyl, isopropylquinazolinyl, cyclopropylquinazolinyl, phenylquinazolinyl, aminoquinazolinyl, (dimethylamino)-quinazolinyl, pyrrolidin-1-ylquinazolinyl, piperidin-1-ylquinazolinyl, piperazin-1-ylquinazolinyl, morpholin-4-ylquinazolinyl, ethoxyquinazolinyl, isopropyloxyquinazolinyl, phenyl-oxyquinazolinyl, imidazo[1,2-a]pyridinyl, methylimidazo[1,2-a]pyridinyl, phenylimidazo[1,2-a]pyridinyl, benzylimidazo[1,2-a]pyridinyl, pyrazolo[1,5-a]pyridinyl, quinoxalinyl, methylquinoxalinyl, dimethylquinoxalinyl, trimethylquinoxalinyl, phenylquinoxalinyl, methylphthalazinyl, naphthyridinyl, 2,3-dihydro-benzo[1,4]-dioxinyl, 1,2-dihydro-2-oxo-quinolinyl, 1,2-dihydro-1-methyl-2-oxo-quinolinyl, 1,2-dihydro-2-methyl-1-oxo-isoquinolinyl, 3,4-dihydro-4-oxo-phthalazinyl, 3,4-dihydro-3-methyl-4-oxo-phthalazinyl, 3,4-dihydro-4-oxo-quinazolinyl, 3,4-dihydro-3-methyl-4-oxo-quinazolinyl or a 2-oxo-2H-chromenyl group, a phenylcarbonylmethyl group, a phenylcarbonylmethyl group wherein the phenyl moiety is substituted by an amino, cyanomethylamino, (ethyloxycarbonylmethyl)amino, (methylaminocarbonyl)methylamino, methylcarbonylamino, ethylcarbonylamino, isopropylcarbonylamino, phenylcarbonylamino, methoxycarbonylamino, (ethyloxycarbonylamino)-carbonylamino or a 2-oxo-imidazolidin-1-yl group, a phenylcarbonylmethyl group wherein the phenyl moiety is substituted by a phenyl group, a phenylcarbonylmethyl group wherein the phenyl moiety is substituted by a carboxy, methoxycarbonyl, ethyloxycarbonyl, aminocarbonyl, methylaminocarbonyl, dimethylaminocarbonyl or morpholin-4-ylcarbonyl group, a phenylcarbonylmethyl group wherein the phenyl moiety is substituted by a methylsulphanyl, methylsulphinyl or methylsulphonyl group, a phenylcarbonylmethyl group wherein the phenyl moiety is substituted by a methoxy, difluoromethoxy, trifluoromethoxy, ethyloxy, isopropyloxy or phenyloxy group, a phenylcarbonylmethyl group wherein the phenyl moiety is substituted by a methylsulphinylmethoxy, carboxymethoxy, ethyloxycarbonylmethoxy, isopropyloxycarbonylmethoxy, aminocarbonyl methoxy, methylaminocarbonylmethoxy, ethylaminocarbonylmethoxy, isopropylamino-carbonylmethoxy, dimethylaminocarbonylmethoxy, pyrrolidin-1-ylcarbonylmethoxy or morpholin-4-ylcarbonylmethoxy group, a phenylcarbonylmethyl group wherein the phenyl moiety is substituted by a 1-(ethyloxycarbonyl)-1-methyl-ethyloxy, 1-(methoxycarbonyl)-ethyloxy or a 1-(aminocarbonyl)-ethyloxy group, a phenylcarbonylmethyl group wherein the phenyl moiety is substituted by two methoxy groups, a phenylcarbonylmethyl group wherein the phenyl moiety is substituted by a methoxy group and a nitro group, a phenylcarbonylmethyl group wherein the phenyl moiety is substituted by a methoxy group and an amino group, a phenylcarbonylmethyl group wherein in the phenyl moiety two adjacent hydrogen atoms are replaced by a —O—$CH_2$—O—, —O—$CF_2$—O—, —O—$CH_2$—$CH_2$—O—, —NH—CO—NH—, —N($CH_3$)—CO—NH—, —N($CH_3$)—CO—N($CH_3$)—, —NH—CO—O— or a —N($CH_3$)—CO—O group, a (2-phenylethyl)carbonylmethyl group, a naphthylcarbonylmethyl, indolylcarbonylmethyl or quinolinylcarbonylmethyl group or a 2-cyanimino-2-phenyl-ethyl group, $R^2$ denotes a methyl, isopropyl, cyclopropyl, phenyl or fluorophenyl group and $R^3$ denotes a 2-methyl-2-propen-1-yl, 2-chloro-2-propen-1-yl or 3-bromo-2-propen-1-yl group a 1-buten-1-yl, 3-methyl-1-buten-1-yl, 2-buten-1-yl, 2-methyl-2-buten-1-yl-or 2,3-dimethyl-2-buten-1-yl group, a 2-butyn-1-yl group, a 1-cyclopenten-1-ylmethyl group or a 2-furanylmethyl group, the tautomers, enantiomers, diastereomers, the mixtures thereof, the prodrugs thereof and the salts thereof.

A preferred sub-group of the second object of the invention comprises compounds of general formula I wherein $R^1$ and $R^2$ are as hereinbefore defined and $R^3$ denotes a 1-buten-1-yl, 2-buten-1-yl or 2-butyn-1-yl group, the tautomers, enantiomers, diastereomers, the mixtures thereof and the salts thereof.

A particularly preferred sub-group of the second object of the invention comprises compounds of general formula I wherein $R^1$ denotes a methyl group which is substituted by a naphthyl, fluoronaphthyl, methylnaphthyl, methoxynaphthyl, (difluoromethoxy)-naphthyl, cyanonaphthyl or nitronaphthyl group, a methyl group which is substituted by a 2-(pentafluorophenyl)ethenyl group, a methyl group which is substituted by a benzofuranyl, methylbenzothiazolyl, quinolinyl, methoxyquinolinyl, isoquinolinyl, methylisoquinolinyl, (difluoromethyl)-isoquinolinyl, (trifluoromethyl)-isoquinolinyl, dimethylisoquinolinyl, (1-cyano-1-methyl-ethyl)isoquinolinyl, phenyl-isoquinolinyl, methoxyisoquinolinyl, 1,2,3,4-tetrahydrophenanthridinyl, quinazolinyl, methylquinazolinyl, isopropylquinazolinyl, cyclopropylquinazolinyl, phenylquinazolinyl, aminoquinazolinyl, (dimethylamino)-quinazolinyl, pyrrolidin-1-ylquinazolinyl, piperidin-1-ylquinazolinyl, piperazin-1-ylquinazolinyl, morpholin-4-ylquinazolinyl, ethoxyquinazolinyl, isopropyloxyquinazolinyl, quinoxalinyl, methylquinoxalinyl, dimethylquinoxalinyl, trimethylquinoxalinyl, phenylquinoxalinyl, [1,5]naphthyridinyl, [1,6]naphthyridinyl, [1,8]naphthyridinyl or a 1,2-dihydro-1-methyl-2-oxo-quinolinyl group, a phenylcarbonylmethyl group, a phenylcarbonylmethyl group wherein the phenyl moiety is substituted by a phenyl group, a phenylcarbonylmethyl group wherein the phenyl moiety is substituted by a methoxy, difluoromethoxy, trifluoromethoxy, ethyloxy, isopropyloxy or phenyloxy group, a phenylcarbonylmethyl group wherein in the phenyl moiety two adjacent hydrogen atoms are replaced by a —O—$CH_2$—O—, —O—$CF_2$—O—, —O—$CH_2$—$CH_2$—O—, —N($CH_3$)—CO—N($CH_3$)— or a —N($CH_3$)—CO—O group, a naphthylcarbonylmethyl, indolylcarbonylmethyl or quinolinylcarbonylmethyl group or
a 2-cyanimino-2-phenyl-ethyl group,
$R^2$ denotes a methyl, isopropyl, cyclopropyl, phenyl or 4-fluorophenyl group and
$R^3$ denotes a 1-buten-1-yl, 2-buten-1-yl or a 2-butyn-1-yl group,
the tautomers, enantiomers, diastereomers, the mixtures thereof and the salts thereof.

A second preferred sub-group of the second object of the invention comprises compounds of general formula I, wherein $R^1$ and $R^2$ are defined as immediately above and $R^3$ denotes a 1-buten-1-yl group,
the tautomers, enantiomers, diastereomers, the mixtures thereof and the salts thereof.

A third preferred sub-group of the second object of the invention comprises compounds of general formula I wherein $R^1$ and $R^2$ are defined as immediately above and $R^3$ denotes a 2-buten-1-yl group, the tautomers, enantiomers, diastereomers, the mixtures thereof and the salts thereof.

A fourth preferred sub-group of the second object of the invention comprises compounds of general formula I wherein $R^1$ and $R^2$ are defined as immediately above and $R^3$ denotes a 2-butyn-1-yl group, the tautomers, enantiomers, diastereomers, the mixtures thereof and the salts thereof.

A third object of the invention relates to compounds of general formula I wherein
$R^1$ denotes a methyl group which is substituted by a naphthyl, fluoronaphthyl, methylnaphthyl, methoxynaphthyl, (difluoromethoxy)-naphthyl, cyanonaphthyl or nitronaphthyl-group,
a methyl group which is substituted by a 2-(pentafluorophenyl)ethenyl group, or
a methyl group which is substituted by a benzofuranyl, methylbenzothiazolyl, quinolinyl, methoxyquinolinyl, isoquinolinyl, methylisoquinolinyl, (difluoromethyl)-isoquinolinyl, (trifluoromethyl)-isoquinolinyl, dimethylisoquinolinyl, (1-cyano-1-methyl-ethyl)isoquinolinyl, phenyl-isoquinolinyl, methoxyisoquinolinyl, 1,2,3,4-tetrahydrophenanthridinyl, quinazolinyl, methylquinazolinyl, isopropylquinazolinyl, cyclopropylquinazolinyl, phenylquinazolinyl, aminoquinazolinyl, (dimethylamino)-quinazolinyl, pyrrolidin-1-ylquinazolinyl, piperidin-1-ylquinazolinyl, piperazin-1-ylquinazolinyl, morpholin-4-ylquinazolinyl, ethoxyquinazolinyl, isopropyloxyquinazolinyl, quinoxalinyl, methylquinoxalinyl, dimethylquinoxalinyl, trimethylquinoxalinyl, phenylquinoxalinyl, [1,5]naphthyridinyl, [1,6]naphthyridinyl, [1,8]naphthyridinyl or a 1,2-dihydro-1-methyl-2-oxo-quinolinyl group,
$R^2$ denotes a methyl, isopropyl, cyclopropyl or phenyl group and
$R^3$ denotes a 2-chlorobenzyl, 2-bromobenzyl, 2-ethynylbenzyl or 2-cyanobenzyl group,
the tautomers, enantiomers, diastereomers, the mixtures thereof and the salts thereof.

A first preferred sub-group of the third object of the invention comprises compounds of general formula I wherein
$R^1$ denotes a (3-methyl-isoquinolin-1-yl)methyl group,
$R^2$ denotes a methyl group and
$R^3$ denotes a 2-chlorobenzyl, 2-bromobenzyl, 2-ethynylbenzyl or 2-cyanobenzyl group,
the tautomers, enantiomers, diastereomers, the mixtures thereof and the salts thereof.

A second preferred sub-group of the third object of the invention comprises compounds of general formula I wherein $R^1$ and $R^2$ are as hereinbefore defined and $R^3$ denotes a 2-chlorobenzyl group, the tautomers, enantiomers, diastereomers, the mixtures thereof and the salts thereof.

A third preferred sub-group of the third object of the invention comprises compounds of general formula I wherein $R^1$ and $R^2$ are as hereinbefore defined and $R^3$ denotes a 2-bromobenzyl group, the tautomers, enantiomers, diastereomers, the mixtures thereof and the salts thereof.

A fourth preferred sub-group of the third object of the invention comprises compounds of general formula I wherein $R^1$ and $R^2$ are as hereinbefore defined and $R^3$ denotes a 2-ethynylbenzyl group, the tautomers, enantiomers, diastereomers, the mixtures thereof and the salts thereof.

A fifth preferred sub-group of the third object of the invention comprises compounds of general formula I wherein $R^1$ and $R^2$ are as hereinbefore defined and $R^3$ denotes a 2-cyanobenzyl group, the tautomers, enantiomers, diastereomers, the mixtures thereof and the salts thereof.

Most particularly preferred are the following compounds of general formula I:

(1) 1-[(quinazolin-2-yl)methyl]-3-methyl-7-(2-butyn-1-yl)-8-((R)-3-amino-piperidin-1-yl)-xanthine,
(2) 1-(2-{2-[(ethylaminocarbonyl)methoxy]-phenyl}-2-oxo-ethyl)-3-methyl-7-(2-butyn-1-yl)-8-((R)-3-amino-piperidin-1-yl)-xanthine,
(3) 1-(2-{2-[(methylaminocarbonyl)methoxy]-phenyl}-2-oxo-ethyl)-3-methyl-7-(2-butyn-1-yl)-8-((R)-3-amino-piperidin-1-yl)-xanthine,
(4) 1-(2-phenyl-2-oxo-ethyl)-3-methyl-7-((E)-2-buten-1-yl)-8-((R)-3-amino-piperidin-1-yl)-xanthine,
(5) 1-[(3-methyl-isoquinolin-1-yl)methyl]-3-methyl-7-(2-butyn-1-yl)-8-((S)-3-amino-piperidin-1-yl)-xanthine,
(6) 1-[(3-methyl-isoquinolin-1-yl)methyl]-3-methyl-7-(2-butyn-1-yl)-8-((R)-3-amino-piperidin-1-yl)-xanthine,
(7) 1-[(4-methyl-isoquinolin-1-yl)methyl]-3-methyl-7-(2-butyn-1-yl)-8-((S)-3-amino-piperidin-1-yl)-xanthine,
(8) 1-[(4-methyl-isoquinolin-1-yl)methyl]-3-methyl-7-(2-butyn-1-yl)-8-((R)-3-amino-piperidin-1-yl)-xanthine,
(9) 1-[2-(2,3-dihydro-benzo[1,4]dioxin-5-yl)-2-oxo-ethyl]-3-methyl-7-(2-butyn-1-yl)-8-(3-(R)-amino-piperidin-1-yl)-xanthine,
(10) 1-[(4-methoxy-naphthalen-1-yl)methyl]-3-methyl-7-(2-butyn-1-yl)-8-((S)-3-amino-piperidin-1-yl)-xanthine,
(11) 1-[(4-methoxy-naphthalen-1-yl)methyl]-3-methyl-7-(2-butyn-1-yl)-8-((R)-3-amino-piperidin-1-yl)-xanthine,
(12) 1-[2-(benzo[1,3]dioxol-4-yl)-2-oxo-ethyl]-3-methyl-7-(2-butyn-1-yl)-8-((R)-3-amino-piperidin-1-yl)-xanthine,
(13) 1-[(4-methyl-quinazolin-2-yl)methyl]-3-methyl-7-(2-butyn-1-yl)-8-(3-(R)-amino-piperidin-1-yl)-xanthine,
(14) 1-(2-{2-[(isopropylcarbonyl)amino]-phenyl}-2-oxo-ethyl)-3-methyl-7-((E)-2-buten-1-yl)-8-((S)-3-amino-piperidin-1-yl)-xanthine,
(15) 1-(2-{2-[(methylaminocarbonyl)methoxy]-phenyl}-2-oxo-ethyl)-3-methyl-7-((E)-2-buten-1-yl)-8-((R)-3-amino-piperidin-1-yl)-xanthine,
(16) 1-(2-{2-[(methylaminocarbonyl)methoxy]-phenyl}-2-oxo-ethyl)-3-methyl-7-((E)-2-buten-1-yl)-8-((S)-3-amino-piperidin-1-yl)-xanthine,
(17) 1-(2-{2-[(isopropylcarbonyl)amino]-phenyl}-2-oxo-ethyl)-3-methyl-7-(2-butyn-1-yl)-8-((R)-3-amino-piperidin-1-yl)-xanthine,
(18) 1-(2-{2-[(isopropylcarbonyl)amino]-phenyl}-2-oxo-ethyl)-3-methyl-7-((E)-2-buten-1-yl)-8-((R)-3-amino-piperidin-1-yl)-xanthine,
(19) 1-[(4-cyano-naphthalen-1-yl)methyl]-3-methyl-7-(2-butyn-1-yl)-8-((R)-3-amino-piperidin-1-yl)-xanthine,
(20) 1-[(4-phenyl-quinazolin-2-yl)methyl]-3-methyl-7-(2-butyn-1-yl)-8-((R)-3-amino-piperidin-1-yl)-xanthine,

(21) 1-[(8-methyl-quinoxalin-6-yl)methyl]-3-methyl-7-(2-butyn-1-yl)-8-((R)-3-amino-piperidin-1-yl)-xanthine,
(22) 1-[(4-fluoro-naphthalen-1-yl)methyl]-3-methyl-7-(2-butyn-1-yl)-8-((R)-3-amino-piperidin-1-yl)-xanthine,
(23) 1-((E)-3-pentafluorophenyl-allyl)-3-methyl-7-(2-butyn-1-yl)-8-((R)-3-amino-piperidin-1-yl)-xanthine,
(24) 1-[(3-trifluoromethyl-isoquinolin-1-yl)methyl]-3-methyl-7-(2-butyn-1-yl)-8-((R)-3-amino-piperidin-1-yl)-xanthine,
(25) 1-[(3-difluoromethyl-isoquinolin-1-yl)methyl]-3-methyl-7-(2-butyn-1-yl)-8-((R)-3-amino-piperidin-1-yl)-xanthine,
(26) 1-[2-(biphenyl-2-yl)-2-oxo-ethyl]-3-methyl-7-(2-butyn-1-yl)-8-((R)-3-amino-piperidin-1-yl)-xanthine,
(27) 1-[(3-methyl-isoquinolin-1-yl)methyl]-3-cyclopropyl-7-(2-butyn-1-yl)-8-((R)-3-amino-piperidin-1-yl)-xanthine,
(28) 1-[2-(3-methoxy-phenyl)-2-oxo-ethyl]-3-methyl-7-(2-butyn-1-yl)-8-((R)-3-amino-piperidin-1-yl)-xanthine,
(29) 1-[(3-methyl-isoquinolin-1-yl)methyl]-3-methyl-7-(2-chloro-benzyl)-8-((R)-3-amino-piperidin-1-yl)-xanthine and
(30) 1-[(3-methyl-isoquinolin-1-yl)methyl]-3-methyl-7-(2-bromo-benzyl)-8-((R)-3-amino-piperidin-1-yl)-xanthine as well as the tautomers, enantiomers, diastereomers, the mixtures thereof and the salts thereof.

According to the invention the compounds of general formula I are obtained by methods known per se, for example by the following methods:

a) reacting a compound of general formula

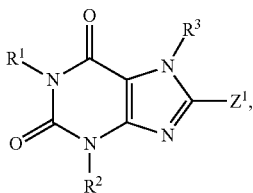
(II)

wherein
R$^1$ to R$^3$ are as hereinbefore defined and
Z$^1$ denotes a leaving group such as a halogen atom, a substituted hydroxy, mercapto, sulphinyl, sulphonyl or sulphonyloxy group such as a chlorine or bromine atom, a methanesulphonyl or methanesulphonyloxy group, with 3-aminopiperidine, the enantiomers thereof or the salts thereof.

The reaction is expediently carried out in a solvent such as isopropanol, butanol, tetrahydrofuran, dioxane, dimethylformamide, dimethylsulphoxide, ethyleneglycol monomethylether, ethyleneglycol diethylether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously also serve as solvent, and optionally in the presence of a reaction accelerator such as an alkali metal halide or a palladium-based catalyst at temperatures between −20 and 180° C., but preferably at temperatures between −10 and 120° C. The reaction may, however, also be carried out without a solvent or in an excess of the 3-aminopiperidine.

b) deprotecting a compound of general formula

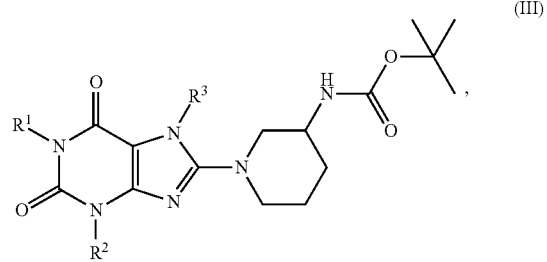
(III)

wherein R$^1$, R$^2$ and R$^3$ are as hereinbefore defined.

The tert.-butyloxycarbonyl group is preferably cleaved by treatment with an acid such as trifluoroacetic acid or hydrochloric acid or by treatment with bromotrimethylsilane or iodotrimethylsilane, optionally using a solvent such as methylene chloride, ethyl acetate, dioxane, methanol, isopropanol or diethyl ether at temperatures between 0 and 80° C.

c) In order to prepare a compound of general formula I wherein R$^1$ according to the definition provided hereinbefore contains a carboxy group:
deprotecting a compound of general formula

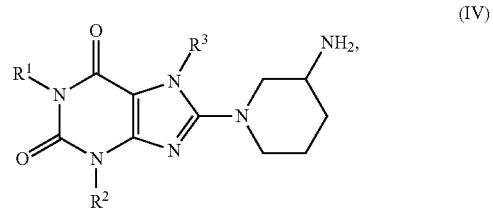
(IV)

wherein R$^2$ and R$^3$ are as hereinbefore defined and R$^{1'}$ contains a carboxy group protected by a C$_{1-4}$-alkyl group.

The protecting group is cleaved by hydrolysis, for example, using an acid such as hydrochloric acid or sulphuric acid or an alkali metal hydroxide such as lithium hydroxide, sodium hydroxide or potassium hydroxide in a solvent such as methanol, ethanol, isopropanol, tetrahydrofuran or dioxane in the presence of water.

In the reactions described hereinbefore, any reactive groups present such as carboxy, amino, alkylamino or imino groups may be protected during the reaction by conventional protecting groups which are cleaved again after the reaction.

For example, a protecting group for a carboxy group may be a trimethylsilyl, methyl, ethyl, tert.butyl, benzyl or tetrahydropyranyl group and
protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/ charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxan, methanol or diethylether.

A trifluoroacetyl group is preferably cleaved by treating with an acid such as hydrochloric acid, optionally in the presence of a solvent such as acetic acid at temperatures between 50 and 120° C., or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to IV used as starting materials are either known from the literature or may be obtained by methods known from the literature (cf. Examples I to LXXI).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in a test set-up in which an extract of human colon carcinoma cell line Caco-2 is used as the DPP-IV source. The differentiation of the cells in order to induce the DPP-IV expression was carried out as described by Reiher et al. in an article entitled "Increased expression of intestinal cell line Caco-2", which appeared in Proc. Natl. Acad. Sci. Vol. 90, pages 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifuging at 35,000 g of for 30 minutes at 4° C. (to remove cell debris).

The DPP-IV assay was carried out as follows:

50 µl substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by adding 30 µl of solubilised Caco-2 protein (final concentration 0.14 µg of protein per well). The test substances to be investigated were typically added prediluted in 20 µl, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case. The following results were obtained:

| Compound (Example no.) | DPP-IV inhibition $IC_{50}$ [nM] |
| --- | --- |
| 2(3) | 2160 |
| 2(9) | 264 |
| 2(12) | 16 |
| 2(17) | 32 |
| 2(20) | 12 |
| 2(25) | 4 |
| 2(27) | 9 |
| 2(35) | 5 |
| 2(37) | 5 |
| 2(43) | 6 |
| 2(51) | 6 |
| 2(52) | 9 |

-continued

| Compound (Example no.) | DPP-IV inhibition IC$_{50}$ [nM] |
|---|---|
| 2(59) | 250 |
| 2(66) | 22 |
| 2(80) | 1 |
| 2(86) | 2 |
| 2(96) | 2 |
| 2(99) | 1 |
| 2(100) | 3 |
| 2(108) | 3 |
| 2(129) | 3 |
| 2(130) | 3 |
| 2(131) | 3 |
| 2(132) | 1 |
| 2(135) | 3 |
| 2(137) | 13 |
| 2(138) | 8 |
| 2(139) | 4 |
| 2(142) | 1 |
| 2(145) | 4 |
| 2(148) | 1 |
| 2(150) | 1 |
| 2(151) | 3 |
| 2(152) | 4 |
| 2(185) | 3 |
| 2(217) | 4 |
| 2(247) | 2 |
| 2(251) | 12 |
| 2(256) | 8 |
| 2(260) | 13 |
| 2(264) | 6 |
| 2(277) | 6 |
| 2(280) | 5 |
| 2(285) | 3 |
| 2(287) | 11 |
| 2(288) | 14 |

The compounds prepared according to the invention are well tolerated, as for example when 10 mg/kg of the compound of Example 2 (80) were administered to rats by oral route no changes in the animals' behaviour could be detected.

In view of their ability to inhibit DPP-IV activity, the compounds of general formula I according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type 1 and type 2 diabetes mellitus, diabetic complications (such as e.g. retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and calcitonin-induced osteoporosis. In addition these substances are capable of preventing B-cell degeneration such as e.g. apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as e.g. GLP-1 and GLP-2 and their link with DPP-IV inhibition, it is likely that the compounds according to the invention are suitable for achieving, inter alia, a sedative or anxiety-relieving effect and also for favourably affecting catabolic states after operations or hormonal stress responses or reducing mortality or morbidity after myocardial infarct. They are also suitable for treating all conditions which are connected with the above mentioned effects and which are mediated by GLP-1 or GLP-2. The compounds according to the invention may also be used as diuretics or antihypertensives and are suitable for preventing and treating acute renal failure. Furthermore, the compounds according to the invention may be used to treat inflammatory diseases of the respiratory tract. They are also suitable for the prevention and treatment of chronic inflammatory intestinal diseases such as e.g. irritable bowel syndrome (IBS), Crohn's disease or ulcerative colitis and also pancreatitis. It is also likely that they can be used for all kinds of damage to or impairment of the gastrointestinal tract such as colitis and enteritis, for example. It is also expected that DPP-IV inhibitors and hence also the compounds according to the invention may be used to treat infertility or to improve fertility in humans or mammals, particularly when the infertility is connected with insulin resistance or polycystic ovary syndrome. On the other hand these substances are suitable for affecting sperm motility and can thus be used as male contraceptives. The substances are also suitable for treating deficiencies of growth hormone which are associated with reduced stature, and may also be used to advantage in any indications in which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based pancreatic carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive and neuropsychiatric diseases of all kinds.

The compounds according to the invention may also be used in conjunction with other active substances. Therapeutic agents which are suitable for such combinations include, for example, antidiabetics, such as metformin, sulphonylureas (e.g. glibenclamide, tolbutamide, glimepiride), nateglinide, repaglinide, thiazolidinedione (e.g. rosiglitazone, pioglitazone), PPAR-gamma agonists (e.g. GI 262570) and antagonists, PPAR-gamma/alpha modulators (e.g. KRP 297), alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, SGLT2 inhibitors such as T-1095, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol-pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol resorption inhibitors such as for example ezetimibe, bile acid-binding substances such as for example cholestyramine, inhibitors of ileac bile acid transport, HDL-raising compounds such as for example inhibitors of CETP or regulators of ABC1 or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or $\beta_3$-agonists such as SB-418790 or AD-9677 as well as agonists of the 5HT2c receptor.

It is also possible to combine the compounds with drugs for treating high blood pressure such as e.g. AII antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the Starting Compounds

Example I 1,3-dimethyl-7-(2,6-dicyano-benzyl)-8-bromo-xanthine

A mixture of 555 mg of 8-bromotheophyllin and 0.39 ml of Hünig base in 9 ml N,N-dimethylformamide is combined with 600 mg of 2-bromomethyl-isophthalonitrile and stirred overnight at ambient temperature. For working up the reaction mixture is poured onto water. The precipitate formed is suction filtered, washed with water and dried.

Yield: 686 mg (83% of theory)

$R_f$ value: 0.56 (silica gel, methylene chloride/methanol=95:5)

Mass spectrum (ESI$^+$): m/z=399, 401 [M+H]$^+$

The following compounds are obtained analogously to Example I:

(1) 3-methyl-7-(3-methyl-2-buten-1-yl)-8-chloro-xanthine
Mass spectrum (ESI$^+$): m/z=269, 271 [M+H]$^+$
(2) 3-methyl-7-(2-cyano-benzyl)-8-chloro-xanthine
Mass spectrum (ESI$^+$): m/z=316, 318 [M+H]$^+$
(3) 1-(2-phenyl-2-oxo-ethyl)-3-methyl-7-(2-butyn-1-yl)-8-bromo-xanthine
Mass spectrum (ESI$^+$): m/z=415, 417 [M+H]$^+$
(4) 3-methyl-7-[(2-trimethylsilanyl-ethoxy)methyl]-8-bromo-xanthine
(Carried out in the presence of potassium carbonate)
Mass spectrum (ESI$^+$): m/z=375, 377 [M+H]$^+$
(5) 3-methyl-7-(3-methyl-2-buten-1-yl)-8-bromo-xanthine
Mass spectrum (ESI$^+$): m/z=313, 315 [M+H]$^+$
(6) 3-methyl-7-(2,3-dimethyl-2-buten-1-yl)-8-bromo-xanthine
$R_f$ value: 0.43 (silica gel, methylene chloride/methanol=9:1)
Mass spectrum (ESI$^+$): m/z=327, 329 [M+H]$^+$ (7) 3-methyl-7-(2-butyn-1-yl)-8-bromo-xanthine
$R_f$ value: 0.72 (silica gel, ethyl acetate)
Mass spectrum (ESI$^+$): m/z=297/299 [M+H]$^+$
(8) 3-methyl-7-((E)-2-buten-1-yl)-8-bromo-xanthine
(The product is contaminated with approx. 10-20% of Z compound)
$R_f$ value: 0.55 (silica gel, cyclohexane/ethyl acetate/methanol=6:3:1)
Mass spectrum (ESI$^+$): m/z=299, 301 [M+H]$^+$
(9) 3-methyl-7-[(1-cyclopenten-1-yl)methyl]-8-bromo-xanthine
Mass spectrum (ESI$^+$): m/z=325, 327 [M+H]$^+$
(10) 1-(2-phenyl-2-oxo-ethyl)-3-methyl-7-[(1-cyclopenten-1-yl)methyl]-8-bromo-xanthine
Mass spectrum (ESI$^+$): m/z=443, 445 [M+H]$^+$
(11) 1-(2-phenyl-2-oxo-ethyl)-3-methyl-7-((E)-2-buten-1-yl)-8-bromo-xanthine
(product contains approx. 25% of Z isomer)
Mass spectrum (ESI$^+$): m/z=417, 419 [M+H]$^+$
(12) 1-(2-phenyl-2-oxo-ethyl)-3-methyl-7-(2-methyl-allyl)-8-bromo-xanthine
$R_f$ value: 0.71 (silica gel, methylene chloride/methanol=95:5)
Mass spectrum (ESI$^+$): m/z=417, 419 [M+H]$^+$
(13) 1-(2-phenyl-2-oxo-ethyl)-3-methyl-7-(3-bromo-allyl)-8-bromo-xanthine
$R_f$ value: 0.68 (silica gel, methylene chloride/methanol=95:5)
Mass spectrum (ESI$^+$): m/z=481, 483, 485 [M+H]$^+$
(14) 1-(2-phenyl-2-oxo-ethyl)-3-methyl-7-[(furan-2-yl)methyl]-8-bromo-xanthine
$R_f$ value: 0.60 (silica gel, methylene chloride/methanol=95:5)
Mass spectrum (ESI$^+$): m/z=443, 445 [M+H]$^+$
(15) 1-(2-phenyl-2-oxo-ethyl)-3-methyl-7-(2-chloro-allyl)-8-bromo-xanthine
$R_f$ value: 0.77 (silica gel, methylene chloride/methanol=95:5)
Mass spectrum (ESI$^+$): m/z=437, 439, 441 [M+H]$^+$
(16) 1-(2-phenyl-2-oxo-ethyl)-3-methyl-7-((Z)-2-methyl-2-buten-1-yl)-8-bromo-xanthine
$R_f$ value: 0.77 (silica gel, methylene chloride/methanol=95:5)
Mass spectrum (ESI$^+$): m/z=431, 433 [M+H]$^+$
(17) 1-(2-phenyl-2-oxo-ethyl)-3-methyl-7-((E)-2-methyl-2-buten-1-yl)-8-bromo-xanthine
$R_f$ value: 0.77 (silica gel, methylene chloride/methanol=95:5)
Mass spectrum (ESI$^+$): m/z=431, 433 [M+H]$^+$
(18) 1-(2-phenyl-2-oxo-ethyl)-3-methyl-7-(1-phenylsulphanyl-butyl)-8-bromo-xanthine
$R_f$ value: 0.83 (silica gel, methylene chloride/methanol=95:5)
Mass spectrum (ESI$^+$): m/z=527, 529 [M+H]$^+$
(19) 3-methyl-7-(3-methyl-1-phenylsulphanyl-butyl)-8-bromo-xanthine
(The [(1-chloro-3-methyl-butyl)sulphanyl]-benzene used as starting material for the reaction is obtained by chlorination of [(3-methyl-butyl)sulphanyl]-benzene with N-chlorosuccinimide in carbon tetrachloride)
$R_f$ value: 0.38 (silica gel, methylene chloride/methanol=95:5)
Mass spectrum (ESI$^+$): m/z=423, 425 [M+H]$^+$
(20) 1,3-dimethyl-7-(2-bromo-benzyl)-8-chloro-xanthine
$R_f$ value: 0.50 (silica gel, cyclohexane/ethyl acetate=1:1)
(21) 1,3-dimethyl-7-(2-chloro-benzyl)-8-chloro-xanthine
$R_f$ value: 0.50 (silica gel, cyclohexane/ethyl acetate=1:1)

(22) 3-cyclopropyl-7-(2-butyn-1-yl)-8-bromo-xanthine
$R_f$ value: 0.45 (ready-made reversed phase TLC plate (E. Merck), acetonitrile/water/trifluoroacetic acid=50:50:1)
Mass spectrum (ESI$^+$): m/z=223/225 [M+H]$^+$ Example II 1-(2-{2-[(ethoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine 63 mg of ethyl bromoacetate are added to a mixture of 200 mg of 1-[2-(2-hydroxy-phenyl)-2-oxo-ethyl]-3-methyl-7-(3-methyl-2-buten-1-yl)-8-[3-(tert.-butyloxycarbonylamino)-piperidin-1-yl]-xanthine and 63 mg of potassium carbonate in 3 ml N,N-dimethylformamide. The reaction mixture is stirred for five hours at ambient temperature. For working up it is combined with water and the precipitate formed is suction filtered, washed with water and dried for three hours at 80° C. in the drying cupboard.
Yield: 216 mg (94% of theory)
Mass spectrum (ESI$^+$): m/z=653 [M+H]$^+$
The following compounds are obtained analogously to Example II:
(1) 1-(2-{2-[(aminocarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=624 [M+H]$^+$
(2) 1-(2-{3-[(methylsulphanyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
$R_f$ value: 0.20 (silica gel, cyclohexane/ethyl acetate=6:4)
Mass spectrum (ESI$^+$): m/z=627 [M+H]$^+$
(3) 1-(2-{3-[(ethoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
$R_f$ value: 0.50 (silica gel, cyclohexane/ethyl acetate=3:7)
(4) 1-(2-{2-[(methylaminocarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=638 [M+H]$^+$
(5) 1-(2-{2-[(dimethylaminocarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=652 [M+H]$^+$
(6) 1-(2-{3-[(methoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=639 [M+H]$^+$
(7) 1-(2-{2-[(ethylaminocarbonyl)methoxy]-phenyl}-2-oxo-ethyl)-3-methyl-7-(2-butyn-1-yl)-8-[(R)-3-(tert.-butyloxycarbonylamino)-piperidin-1-yl]-xanthine
Mass spectrum (ESI$^+$): m/z=636 [M+H]$^+$
(8) 1-(2-{2-[(methylaminocarbonyl)methoxy]-phenyl}-2-oxo-ethyl)-3-methyl-7-[(1-cyclopenten-1-yl)methyl]-8-[3-(tert.-butyloxycarbonylamino)-piperidin-1-yl]-xanthine
Mass spectrum (ESI$^+$): m/z=650 [M+H]$^+$
(9) 1-(2-{2-[(methylaminocarbonyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=622 [M+H]$^+$
(10) 1-(2-{2-[(aminocarbonyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=608 [M+H]$^+$
(11) 1-(2-{2-[(methoxycarbonyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=623 [M+H]$^+$
(12) 1-(2-{2-[(isopropyloxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=667 [M+H]$^+$
(13) 1-(2-{2-[(methylaminocarbonyl)methoxy]-phenyl}-2-oxo-ethyl)-3-methyl-7-(2-butyn-1-yl)-8-[(R)-3-(tert.-butyloxycarbonylamino)-piperidin-1-yl]-xanthine
Mass spectrum (ESI$^+$): m/z=622 [M+H]$^+$
(14) 1-(2-{2-[(methylaminocarbonyl)methoxy]-phenyl}-2-oxo-ethyl)-3-methyl-7-((E)-2-buten-1-yl)-8-[3-(tert.-butyloxycarbonylamino)-piperidin-1-yl]-xanthine
(product contains some Z isomer)
$R_f$ value: 0.35 (silica gel, cyclohexane/ethyl acetate/methanol=5:4:1)
Mass spectrum (ESI$^+$): m/z=624 [M+H]$^+$
(15) 1-(2-{2-[(ethylaminocarbonyl)methoxy]-phenyl}-2-oxo-ethyl)-3-methyl-7-(2-butyn-1-yl)-8-[(S)-3-(tert.-butyloxycarbonylamino)-piperidin-1-yl]-xanthine
Mass spectrum (ESI$^+$): m/z=636 [M+H]$^+$
(16) 1-(2-{2-[(methylaminocarbonyl)methoxy]-phenyl}-2-oxo-ethyl)-3-methyl-7-(2-butyn-1-yl)-8-[(S)-3-(tert.-butyloxycarbonylamino)-piperidin-1-yl]-xanthine
Mass spectrum (ESI$^+$): m/z=622 [M+H]$^+$
(17) 1-(2-{2-[(methoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=639 [M+H]$^+$
(18) 1-(2-{2-[(methylaminocarbonyl)methoxy]-phenyl}-2-oxo-ethyl)-3-methyl-7-(3-methyl-2-buten-1-yl)-8-[(S)-3-(tert.-butyloxycarbonylamino)-piperidin-1-yl]-xanthine
Mass spectrum (ESI$^+$): m/z=638 [M+H]$^+$
(19) 2-(2-acetyl-phenoxy)-N-ethyl-acetamide
Mass spectrum (ESI$^+$): m/z=222 [M+H]$^+$
(20) 1-{2-[2-(1-methoxycarbonyl-ethoxy)-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=637 [M+H]$^+$
(21) 1-{2-[2-(1-aminocarbonyl-ethoxy)-phenyl]-2-oxo-ethyl}-3-methyl-7-(2-butyn-1-yl)-8-[3-(tert.-butyloxycarbonylamino)-piperidin-1-yl]xanthine
Mass spectrum (ESI$^+$): m/z=622 [M+H]$^+$
(22) 2-(2-acetyl-phenoxy)-N-methyl-acetamide
Mass spectrum (ESI$^+$): m/z=208 [M+H]$^+$
(23) 1-{2-[2-(2-oxo-propoxy)-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=607 [M+H]$^+$
(24) 1-{2-[2-(1-ethoxycarbonyl-1-methyl-ethoxy)-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=665 [M+H]$^+$
(25) 1-{2-[2-cyanomethoxy-phenyl]-2-oxo-ethyl}-3-methyl-7-(2-butyn-1-yl)-8-[3-(tert.-butyloxycarbonylamino)-piperidin-1-yl]-xanthine
Mass spectrum (ESI$^+$): m/z=590 [M+H]$^+$
(26) 1-(2-{2-[(methylsulphanyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=611 [M+H]$^+$
(27) 1-{[2-(tert.-butylcarbonyl)-benzofuran-3-yl]methyl}-3-methyl-7-(2-butyn-1-yl)-8-[3-(tert.-butyloxycarbonylamino)-piperidin-1-yl]-xanthine (Formed as main product when 1-[2-(2-hydroxy-phenyl)-2-oxo-ethyl]-3-methyl-7-(2-butyn-1-yl)-8-[3-(tert.-butyloxycarbonylamino)-piperidin-1-yl]-xanthine is reacted with 1-chloro-3,3-dimethyl-butan-2-one)

Mass spectrum (ESI$^+$): m/z=631 [M+H]$^+$

Example III

1-[2-(2-hydroxy-phenyl)-2-oxo-ethyl]-3-methyl-7-(3-methyl-2-buten-1-yl)-8-[3-(tert.-butyloxycarbonylamino)-piperidin-1-yl]-xanthine 1.30 g of 3-tert.-butyloxycarbonylamino-piperidine are added to a mixture of 2.51 g of 1-[2-(2-hydroxy-phenyl)-2-oxo-ethyl]-3-methyl-7-(3-methyl-2-buten-1-yl)-8-chloro-xanthine and 880 mg of sodium carbonate in 8 ml of dimethylsulphoxide. The reaction mixture is stirred for 18 hours at 60° C. For working up it is combined with water and the precipitate formed is suction filtered. The solid crude product is dissolved in ethyl acetate, the solution is dried over magnesium sulphate and evaporated down. The flask residue is chromatographed through a silica gel column with cyclohexane/ethyl acetate (10:1 to 1:1) as eluant.

Yield: 2.56 g (91% of theory)

Mass spectrum (ESI$^+$): m/z=567 [M+H]$^+$

The following compounds are obtained analogously to Example III:

(1) 3-methyl-7-(3-methyl-2-buten-1-yl)-8-[3-(tert.-butyloxycarbonylamino)-piperidin-1-yl]-xanthine
Mass spectrum (ESI$^+$): m/z=433 [M+H]$^+$ (2) 1-(1-methyl-2-oxo-2-phenyl-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=565 [M+H]$^+$ (3) 3-methyl-7-(2-cyano-benzyl)-8-[3-(tert.-butyloxycarbonylamino)-piperidin-1-yl]-xanthine
R$_f$ value: 0.90 (silica gel, methylene chloride/methanol=9:1)
Mass spectrum (ESI$^-$): m/z=478 [M−H]$^-$ (4) 1-methyl-3-[(methoxycarbonyl)methyl]-7-(2-cyano-benzyl)-8-[3-(tert.-butyloxycarbonylamino)-piperidin-1-yl]-xanthine
Mass spectrum (ESI$^+$): m/z=552 [M+H]$^+$ (5) 1-methyl-3-cyanomethyl-7-(2-cyano-benzyl)-8-[3-(tert.-butyloxycarbonyl-amino)-piperidin-1-yl]-xanthine
Mass spectrum (ESI$^+$): m/z=519 [M+H]$^+$ (6) 1-methyl-3-(2-propyn-1-yl)-7-(2-cyano-benzyl)-8-[3-(tert.-butyloxycarbonyl-amino)-piperidin-1-yl]-xanthine
Mass spectrum (ESI$^+$): m/z=518 [M+H]$^+$ (7) 1-[2-(3-nitro-phenyl)-2-oxo-ethyl]-3-methyl-7-(3-methyl-2-buten-1-yl)-8-[3-(tert.-butyloxycarbonylamino)-piperidin-1-yl]-xanthine
R$_f$ value: 0.25 (silica gel, cyclohexane/ethyl acetate/methanol=7:2:1)
Mass spectrum (ESI$^+$): m/z=596 [M+H]$^+$ (8) 1-methyl-3-(2-propen-1-yl)-7-(2-cyano-benzyl)-8-[3-(tert.-butyloxycarbonyl-amino)-piperidin-1-yl]-xanthine
Mass spectrum (ESI$^+$): m/z=520 [M+H]$^+$ (9) 1-(2-phenyl-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=535 [M+H]$^+$

(10) 1-[2-(2-nitro-phenyl)-2-oxo-ethyl]-3-methyl-7-(3-methyl-2-buten-1-yl)-8-[3-(tert.-butyloxycarbonylamino)-piperidin-1-yl]-xanthine
R$_f$ value: 0.52 (silica gel, cyclohexane/ethyl acetate=3:7)
Mass spectrum (ESI$^+$): m/z=596 [M+H]$^+$

(11) 1-methyl-3-phenyl-7-(2-cyano-benzyl)-8-[3-(tert.-butyloxycarbonylamino)-piperidin-1-yl]-xanthine
Mass spectrum (ESI$^+$): m/z=556 [M+H]$^+$

(12) 1-[2-(2-nitro-phenyl)-2-oxo-ethyl]-3-methyl-7-(3-methyl-2-buten-1-yl)-8-[(S)-3-(tert.-butyloxycarbonylamino)-piperidin-1-yl]-xanthine
Mass spectrum (ESI$^+$): m/z=596 [M+H]$^+$

(13) 1-[(cinnolin-4-yl)methyl]-3-methyl-7-(3-methyl-2-buten-1-yl)-8-[3-(tert.-butyloxycarbonylamino)-piperidin-1-yl]-xanthine mixed with 1-[(1,4-dihydro-cinnolin-4-yl)methyl]-3-methyl-7-(3-methyl-2-buten-1-yl)-8-[3-(tert.-butyloxycarbonylamino)-piperidin-1-yl]-xanthine
R$_f$ value: 0.62 (silica gel, ethyl acetate)

(14) 1-({4-oxo-3-[(2-trimethylsilanyl-ethoxy)methyl]-3,4-dihydro-phthalazin-1-yl}methyl)-3-methyl-7-(3-methyl-2-buten-1-yl)-8-[3-(tert.-butyloxycarbonylamino)-piperidin-1-yl]-xanthine
(Carried out with potassium carbonate in the presence of Hünig base)
R$_f$ value: 0.27 (silica gel, cyclohexane/ethyl acetate=1:1)
Mass spectrum (ESI$^+$): m/z=720 [M+H]$^+$

(15) 1-[(isoquinolin-3-yl)methyl]-3-methyl-7-(3-methyl-2-buten-1-yl)-8-[3-(tert.-butyloxycarbonylamino)-piperidin-1-yl]-xanthine
R$_f$ value: 0.31 (silica gel, ethyl acetate/petroleum ether=7:3)
Mass spectrum (ESI$^+$): m/z=574 [M+H]$^+$

(16) 1-[(3-methyl-4-oxo-3,4-dihydro-phthalazin-1-yl)methyl]-3-methyl-7-(3-methyl-2-buten-1-yl)-8-[3-(tert.-butyloxycarbonylamino)-piperidin-1-yl]-xanthine
R$_f$ value: 0.45 (silica gel, methylene chloride/methanol/conc. aqueous ammonia=95:5)
Mass spectrum (ESI$^+$): m/z=605 [M+H]$^+$

(17) 3-methyl-7-(2,3-dimethyl-2-buten-1-yl)-8-[3-(tert.-butyloxycarbonylamino)-piperidin-1-yl]-xanthine
(Carried out with potassium carbonate)
R$_f$ value: 0.42 (silica gel, methylene chloride/methanol=20:1)
Mass spectrum (ESI$^+$): m/z=447 [M+H]$^+$

(18) 3-methyl-7-(2-butyn-1-yl)-8-[3-(tert.-butyloxycarbonylamino)-piperidin-1-yl]-xanthine
(Carried out with potassium carbonate)
Melting point: 235-237° C.
Mass spectrum (ESI$^+$): m/z=417 [M+H]$^+$

(19) 1-[(quinolin-4-yl)methyl]-3-methyl-7-(2-butyn-1-yl)-8-[3-(tert.-butyloxycarbonylamino)-piperidin-1-yl]-xanthine
(Carried out with potassium carbonate)
R$_f$ value: 0.36 (silica gel, ethyl acetate)
Mass spectrum (ESI$^+$): m/z=558 [M+H]$^+$

(20) 1-[(isoquinolin-1-yl)methyl]-3-methyl-7-(2-butyn-1-yl)-8-[3-(tert.-butyloxycarbonylamino)-piperidin-1-yl]-xanthine
(Carried out with potassium carbonate)
R$_f$ value: 0.71 (silica gel, ethyl acetate)
Mass spectrum (ESI$^+$): m/z=558 [M+H]$^+$

(21) 1-[(isoquinolin-1-yl)methyl]-3-methyl-7-((E)-2-buten-1-yl)-8-[3-(tert.-butyloxycarbonylamino)-piperidin-1-yl]-xanthine
(Carried out with potassium carbonate; the product contains approx. 20% of Z isomer)
R$_f$ value: 0.24 (silica gel, ethyl acetate/petroleum ether=1:1)
Mass spectrum (ESI$^+$): m/z=560 [M+H]$^+$

(22) 3-methyl-7-(2-butyn-1-yl)-8-[(R)-3-(tert.-butyloxycarbonylamino)-piperidin-1-yl]-xanthine
(Carried out with potassium carbonate)
$R_f$ value: 0.64 (silica gel, ethyl acetate)
Mass spectrum (ESI$^+$): m/z=417 [M+H]$^+$

(23) 3-methyl-7-(2-butyn-1-yl)-8-[(S)-3-(tert.-butyloxycarbonylamino)-piperidin-1-yl]-xanthine
(Carried out with potassium carbonate)
$R_f$ value: 0.64 (silica gel, ethyl acetate)
Mass spectrum (ESI$^+$): m/z=417 [M+H]$^+$

(24) 3-methyl-7-((E)-2-buten-1-yl)-8-[(S)-3-(tert.-butyloxycarbonylamino)-piperidin-1-yl]-xanthine
(product contains approx. 15% of Z isomer)
$R_f$ value: 0.35 (silica gel, cyclohexane/ethyl acetate=3:7)
Mass spectrum (ESI$^+$): m/z=419 [M+H]$^+$

(25) 3-methyl-7-((E)-2-buten-1-yl)-8-[(R)-3-(tert.-butyloxycarbonylamino)-piperidin-1-yl]-xanthine
(product contains approx. 15% of Z isomer)
$R_f$ value: 0.35 (silica gel, cyclohexane/ethyl acetate=3:7)
Mass spectrum (ESI$^+$): m/z=419 [M+H]$^+$

(26) 1-[2-(2-hydroxy-phenyl)-2-oxo-ethyl]-3-methyl-7-(2-butyn-1-yl)-8-[(R)-3-(tert.-butyloxycarbonylamino)-piperidin-1-yl]-xanthine
Mass spectrum (ESI$^+$): m/z=551 [M+H]$^+$

(27) 1-[2-(2-amino-phenyl)-2-oxo-ethyl]-3-methyl-7-[(1-cyclopenten-1-yl)methyl]-8-[3-(tert.-butyloxycarbonylamino)-piperidin-1-yl]-xanthine
Mass spectrum (ESI$^+$): m/z=578 [M+H]$^+$

(28) 1-(2-phenyl-2-oxo-ethyl)-3-methyl-7-[(1-cyclopenten-1-yl)methyl]-8-[3-(tert.-butyloxycarbonylamino)-piperidin-1-yl]-xanthine
Mass spectrum (ESI$^+$): m/z=563 [M+H]$^+$

(29) 1-[2-(2-hydroxy-phenyl)-2-oxo-ethyl]-3-methyl-7-[(1-cyclopenten-1-yl)methyl]-8-[3-(tert.-butyloxycarbonylamino)-piperidin-1-yl]-xanthine
Mass spectrum (ESI$^+$): m/z=579 [M+H]$^+$

(30) 1-methyl-3-isopropyl-7-(2-cyano-benzyl)-8-[3-(tert.-butyloxycarbonylamino)-piperidin-1-yl]-xanthine
Mass spectrum (ESI$^+$): m/z=522 [M+H]$^+$

(31) 1-[2-(2-hydroxy-phenyl)-2-oxo-ethyl]-3-methyl-7-(2-butyn-1-yl)-8-[3-(tert.-butyloxycarbonylamino)-piperidin-1-yl]-xanthine
Mass spectrum (ESI$^+$): m/z=551 [M+H]$^+$

(32) 1-[2-(2-amino-phenyl)-2-oxo-ethyl]-3-methyl-7-((E)-2-buten-1-yl)-8-[3-(tert.-butyloxycarbonylamino)-piperidin-1-yl]-xanthine
(product contains approx. 10% of Z isomer)
$R_f$ value: 0.20 (silica gel, cyclohexane/ethyl acetate=1:1)
Mass spectrum (ESI$^+$): m/z=552 [M+H]$^+$

(33) 1-(2-phenyl-2-oxo-ethyl)-3-methyl-7-((E)-2-buten-1-yl)-8-[3-(tert.-butyloxy-carbonylamino)-piperidin-1-yl]-xanthine
(product contains approx. 25% of Z isomer)
Mass spectrum (ESI$^+$): m/z=537 [M+H]$^+$

(34) 1-[2-(2-hydroxy-phenyl)-2-oxo-ethyl]-3-methyl-7-(2-butyn-1-yl)-8-[(R)-3-(tert.-butyloxycarbonylamino)-piperidin-1-yl]-xanthine

(35) 1-[2-(2-hydroxy-phenyl)-2-oxo-ethyl]-3-methyl-7-((E)-2-buten-1-yl)-8-[3-(tert.-butyloxycarbonylamino)-piperidin-1-yl]-xanthine
(product contains some Z isomer)
$R_f$ value: 0.30 (silica gel, cyclohexane/ethyl acetate=4:6)
Mass spectrum (ESI$^+$): m/z=553 [M+H]$^+$

(36) 1-[2-(2-hydroxy-phenyl)-2-oxo-ethyl]-3-methyl-7-(2-butyn-1-yl)-8-[(S)-3-(tert.-butyloxycarbonylamino)-piperidin-1-yl]-xanthine
Mass spectrum (ESI$^+$): m/z=551 [M+H]$^+$

(37) 1-[2-(2-amino-phenyl)-2-oxo-ethyl]-3-methyl-7-(2-butyn-1-yl)-8-[3-(tert.-butyloxycarbonylamino)-piperidin-1-yl]-xanthine
$R_f$ value: 0.50 (silica gel, methylene chloride/methanol=95:5)
Mass spectrum (ESI$^+$): m/z=550 [M+H]$^+$

(38) 1-[2-(2-hydroxy-phenyl)-2-oxo-ethyl]-3-methyl-7-(3-methyl-2-buten-1-yl)-8-[(S)-3-(tert.-butyloxycarbonylamino)-piperidin-1-yl]-xanthine
Mass spectrum (ESI$^+$): m/z=567 [M+H]$^+$

(39) 1-(2-phenyl-2-oxo-ethyl)-3-methyl-7-(2-butyn-1-yl)-8-[(R)-3-(tert.-butyloxy-carbonylamino)-piperidin-1-yl]-xanthine
Mass spectrum (ESI$^+$): m/z=535 [M+H]$^+$

(40) 1-methyl-3-[(2-trimethylsilanyl-ethoxy)methyl]-7-(2-cyano-benzyl)-8-[3-(tert.-butyloxycarbonylamino)-piperidin-1-yl]-xanthine
Mass spectrum (ESI$^+$): m/z=610 [M+H]$^+$

(41) 3-methyl-7-(2-butyn-1-yl)-8-[(S)-3-(tert.-butyloxycarbonylamino)-piperidin-1-yl]-xanthine
(Carried out with potassium carbonate)
$R_f$ value: 0.52 (silica gel, ethyl acetate)
Mass spectrum (ESI$^+$): m/z=417 [M+H]$^+$

(42) 1-(2-phenyl-2-oxo-ethyl)-3-methyl-7-(2-methyl-allyl)-8-[3-(tert.-butyloxycarbonylamino)-piperidin-1-yl]-xanthine
$R_f$ value: 0.46 (silica gel, methylene chloride/methanol=95:5)

(43) 1-(2-phenyl-2-oxo-ethyl)-3-methyl-7-(3-bromo-allyl)-8-[3-(tert.-butyloxycarbonylamino)-piperidin-1-yl]-xanthine
$R_f$ value: 0.22 (silica gel, methylene chloride/methanol=95:5)
Mass spectrum (ESI$^+$): m/z=601, 603 [M+H]$^+$

(44) 1-(2-phenyl-2-oxo-ethyl)-3-methyl-7-[(furan-2-yl)methyl]-8-[3-(tert.-butyloxycarbonylamino)-piperidin-1-yl]-xanthine
$R_f$ value: 0.41 (silica gel, methylene chloride/methanol=95:5)

(45) 1-(2-phenyl-2-oxo-ethyl)-3-methyl-7-(2-chloro-allyl)-8-[3-(tert.-butyloxycarbonylamino)-piperidin-1-yl]-xanthine
$R_f$ value: 0.49 (silica gel, methylene chloride/methanol=95:5)
Mass spectrum (ESI$^+$): m/z=557, 559 [M+H]$^+$

(46) 1-(2-phenyl-2-oxo-ethyl)-3-methyl-7-(2-butyn-1-yl)-8-[(S)-3-(tert.-butyloxy-carbonylamino)-piperidin-1-yl]-xanthine
Mass spectrum (ESI$^+$): m/z=535 [M+H]$^+$

(47) 1-[2-(2-amino-phenyl)-2-oxo-ethyl]-3-methyl-7-((E)-2-buten-1-yl)-8-[(S)-3-(tert.-butyloxycarbonylamino)-piperidin-1-yl]-xanthine
$R_f$ value: 0.40 (silica gel, cyclohexane/ethyl acetate=4:6)
Mass spectrum (ESI$^+$): m/z=552 [M+H]$^+$

(48) 1-[2-(2-nitro-phenyl)-2-oxo-ethyl]-3-methyl-7-((E)-2-buten-1-yl)-8-[(R)-3-(tert.-butyloxycarbonylamino)-piperidin-1-yl]-xanthine
$R_f$ value: 0.50 (silica gel, cyclohexane/ethyl acetate=1:2)

(49) 1-[2-(2-nitro-phenyl)-2-oxo-ethyl]-3-methyl-7-((E)-2-buten-1-yl)-8-[(S)-3-(tert.-butyloxycarbonylamino)-piperidin-1-yl]-xanthine
Mass spectrum (ESI$^+$): m/z=582 [M+H]$^+$

(50) 1-[2-(2-nitro-3-methoxy-phenyl)-2-oxo-ethyl]-3-methyl-7-(3-methyl-2-buten-1-yl)-8-[3-(tert.-butyloxycarbonylamino)-piperidin-1-yl]-xanthine
Mass spectrum (ESI$^+$): m/z=626 [M+H]$^+$

(51) 1-(2-{2-oxo-3-[(2-trimethylsilanyl-ethoxy)methyl]-2,3-dihydro-benzooxazol-7-yl}-2-oxo-ethyl)-3-methyl-7-(3-methyl-2-buten-1-yl)-8-[3-(tert.-butyloxycarbonylamino)-piperidin-1-yl]-xanthine
Mass spectrum (ESI$^+$): m/z=738 [M+H]$^+$

(52) 1-(2-phenyl-2-oxo-ethyl)-3-methyl-7-((Z)-2-methyl-2-buten-1-yl)-8-[3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=551 [M+H]$^+$

(53) 1-(2-phenyl-2-oxo-ethyl)-3-methyl-7-((E)-2-methyl-2-buten-1-yl)-8-[3-(tert.-butyloxycarbonylamino)-piperidin-1-yl]-xanthine
Mass spectrum (ESI$^+$): m/z=551 [M+H]$^+$

(54) 1-(2-{2-oxo-3-[(2-trimethylsilanyl-ethoxy)methyl]-2,3-dihydro-benzooxazol-4-yl}-2-oxo-ethyl)-3-methyl-7-(2-butyn-1-yl)-8-[3-(tert.-butyloxycarbonylamino)-piperidin-1-yl]-xanthine
$R_f$ value: 0.40 (silica gel, petroleum ether/ethyl acetate=1:1)
Mass spectrum (ESI$^+$): m/z=722 [M+H]$^+$

(55) 1-[2-(2,2-difluoro-benzo[1,3]dioxol-4-yl)-2-oxo-ethyl]-3-methyl-7-(2-butyn-1-yl)-8-[(R)-3-(tert.-butyloxycarbonylamino)-piperidin-1-yl]-xanthine
Mass spectrum (ESI$^+$): m/z=615 [M+H]$^+$

(56) 1-[2-(2,2-difluoro-benzo[1,3]dioxol-4-yl)-2-oxo-ethyl]-3-methyl-7-(2-butyn-1-yl)-8-[(S)-3-(tert.-butyloxycarbonylamino)-piperidin-1-yl]-xanthine
Mass spectrum (ESI$^+$): m/z=615 [M+H]$^+$

(57) 1-[(1-methyl-1H-indol-2-yl)methyl]-3-methyl-7-(2-butyn-1-yl)-8-[3-(tert.-butyloxy-carbonylamino)-piperidin-1-yl]-xanthine
$R_f$ value: 0.80 (silica gel, methylene chloride/methanol=95:5)
Mass spectrum (ESI$^+$): m/z=560 [M+H]$^+$

(58) 1-[(quinolin-3-yl)methyl]-3-methyl-7-(2-butyn-1-yl)-8-[3-(tert.-butyloxycarbonyl-amino)-piperidin-1-yl]-xanthine
$R_f$ value: 0.50 (silica gel, ethyl acetate)
Mass spectrum (ESI$^+$): m/z=558 [M+H]$^+$

(59) 1-{[1-(tert.-butyloxycarbonylamino)-1H-indol-2-yl]methyl}-3-methyl-7-(2-butyn-1-yl)-8-[3-(tert.-butyloxycarbonylamino)-piperidin-1-yl]-xanthine
$R_f$ value: 0.40 (silica gel, petroleum ether/ethyl acetate=1:1)
Mass spectrum (ESI$^+$): m/z=646 [M+H]$^+$

(60) 1-[(2-methyl-1-[(2-trimethylsilanyl-ethoxy)methyl]-1H-benzoimidazol-5-yl)methyl]-3-methyl-7-(2-butyn-1-yl)-8-[3-(tert.-butyloxycarbonylamino)-piperidin-1-yl]-xanthine (mixed with 1-[(2-methyl-3-[(2-trimethylsilanyl-ethoxy)methyl]-3H-benzoimidazol-5-yl)methyl]-3-methyl-7-(2-butyn-1-yl)-8-[3-(tert.-butyloxycarbonylamino)-piperidin-1-yl]-xanthine)
$R_f$ value: 0.15 (silica gel, ethyl acetate)
Mass spectrum (ESI$^+$): m/z=691 [M+H]$^+$

(61) 1-[2-(quinolin-8-yl-]-2-oxo-ethyl]-3-methyl-7-(2-butyn-1-yl)-8-[3-(tert.-butyloxy-carbonylamino)-piperidin-1-yl]-xanthine
$R_f$ value: 0.35 (silica gel, methylene chloride/methanol=95:5)
Mass spectrum (ESI$^+$): m/z=586 [M+H]$^+$

(62) 1-[(1-[(2-trimethylsilanyl-ethoxy)methyl]-1H-benzoimidazol-5-yl)methyl]-3-methyl-7-(2-butyn-1-yl)-8-[3-(tert.-butyloxycarbonylamino)-piperidin-1-yl]-xanthine (mixed with 1-[(3-[(2-trimethylsilanyl-ethoxy)methyl]-3H-benzoimidazol-5-yl)methyl]-3-methyl-7-(2-butyn-1-yl)-8-[3-(tert.-butyloxycarbonylamino)-piperidin-1-yl]-xanthine)
$R_f$ value: 0.23 (silica gel, ethyl acetate)
Mass spectrum (ESI$^+$): m/z=677 [M+H]$^+$

(63) 1-[(pyrazolo[1,5-a]pyridin-2-yl)methyl]-3-methyl-7-(2-butyn-1-yl)-8-[3-(tert.-butyloxycarbonylamino)-piperidin-1-yl]-xanthine
$R_f$ value: 0.46 (silica gel, methylene chloride/methanol=95:5)
Mass spectrum (ESI$^+$): m/z=547 [M+H]$^+$

(64) 1-(2-phenyl-2-oxo-ethyl)-3-methyl-7-((E)-1-buten-1-yl)-8-[3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=537 [M+H]$^+$

(65) 1-{2-[1-(tert.-butyloxycarbonyl)-1H-indol-7-yl]-2-oxo-ethyl}-3-methyl-7-(2-butyn-1-yl)-8-[3-(tert.-butyloxycarbonylamino)-piperidin-1-yl]-xanthine
$R_f$ value: 0.38 (silica gel, petroleum ether/ethyl acetate=1:1)

(66) 1-[(3-methyl-isoquinolin-1-yl)methyl]-3-methyl-7-(3-methyl-1-buten-1-yl)-8-[(R)-3-(tert.-butyloxycarbonylamino)-piperidin-1-yl]-xanthine
$R_f$ value: 0.40 (silica gel, methylene chloride/methanol=95:5)
Mass spectrum (ESI$^+$): m/z=588 [M+H]$^+$

(67) 1,3-dimethyl-7-(2-bromo-benzyl)-8-[3-(tert.-butyloxycarbonylamino)-piperidin-1-yl]-xanthine
$R_f$ value: 0.40 (silica gel, cyclohexane/ethyl acetate=1:1)

(68) 1,3-dimethyl-7-(2-chloro-benzyl)-8-[3-(tert.-butyloxycarbonylamino)-piperidin-1-yl]-xanthine
$R_f$ value: 0.42 (silica gel, cyclohexane/ethyl acetate=1:1)

(69) 1-[(3-methyl-isoquinolin-1-yl)methyl]-3-methyl-7-(2-cyano-benzyl)-8-[3-(tert.-butyloxycarbonylamino)-piperidin-1-yl]-xanthine
Mass spectrum (ESI$^+$): m/z=635 [M+H]$^+$
$R_f$ value: 0.40 (silica gel, cyclohexane/ethyl acetate=3:7)

(70) 3-cyclopropyl-7-(2-butyn-1-yl)-8-[3-(tert.-butyloxycarbonylamino)-piperidin-1-yl]-xanthine
Mass spectrum (ESI$^+$): m/z=443 [M+H]$^+$
$R_f$ value: 0.70 (silica gel, ethyl acetate)

(71) 3-cyclopropyl-7-(2-butyn-1-yl)-8-[(R)-3-(tert.-butyloxycarbonylamino)-piperidin-1-yl]-xanthine
$R_f$ value: 0.35 (ready-made reversed phase TLC plate (E. Merck), acetonitrile/water/trifluoroacetic acid=50:50:1)
Mass spectrum (ESI$^+$): m/z=443 [M+H]$^+$

(72) 1-[(3-methyl-isoquinolin-1-yl)methyl]-3-methyl-7-(2-chloro-benzyl)-8-[(R)-3-(tert.-butyloxycarbonylamino)-piperidin-1-yl]-xanthine
Mass spectrum (ESI$^+$): m/z=644, 646 [M+H]$^+$
$R_f$ value: 0.39 (silica gel, cyclohexane/ethyl acetate=1:1)

(73) 1-[(3-methyl-isoquinolin-1-yl)methyl]-3-methyl-7-(2-bromo-benzyl)-8-[(R)-3-(tert.-butyloxycarbonylamino)-piperidin-1-yl]-xanthine
Mass spectrum (ESI$^+$): m/z=644, 646 [M+H]$^+$

(74) 1-[(4-methyl-quinazolin-2-yl)methyl]-3-methyl-7-(2-chloro-benzyl)-8-[(R)-3-(tert.-butyloxycarbonylamino)-piperidin-1-yl]-xanthine
Prepared by reacting (4-methyl-quinazolin-2-yl)-methyl-chloride and 3-methyl-7-(2-chlorobenzyl)-8-bromo-xanthine and subsequently reacting with (R)-3-(tert.-butyloxycarbonylamino)-piperidine
Mass spectrum (ESI$^+$): m/z=645, 647 [M+H]$^+$

(75) 1-[(4-phenyl-quinazolin-2-yl)methyl]-3-methyl-7-(2-chloro-benzyl)-8-[(R)-3-(tert.-butyloxycarbonylamino)-piperidin-1-yl]-xanthine Prepared by reacting (4-phenyl-quinazolin-2-yl)-methyl-chloride and 3-methyl-7-(2-chlorobenzyl)-8-bromo-xanthine and subsequently reacting with (R)-3-(tert.-butyloxycarbonylamino)-piperidine Mass spectrum (ESI$^+$): m/z=707, 709 [M+H]$^+$ Example IV 1-[2-(2-hydroxy-phenyl)-2-oxo-ethyl]-3-methyl-7-(3-methyl-2-buten-1-yl)-8-chloro-xanthine Prepared by treating 1-[2-(2-methoxy-phenyl)-2-oxo-ethyl]-3-methyl-7-(3-methyl-2-buten-1-yl)-8-chloro-xanthine with boron tribromide in methylene chloride. The desired product is contaminated with approx. 20% 1-[2-(2-hydroxy-phenyl)-2-oxo-ethyl]-3-methyl-7-(3-bromo-3-methyl-butyl)-8-chloro-xanthine.

Mass spectrum (ESI$^+$): m/z=403, 405 [M+H]$^+$

The following compounds are obtained analogously to Example IV:

(1) 1-[2-(2-hydroxy-phenyl)-2-oxo-ethyl]-3-methyl-7-(2-butyn-1-yl)-8-bromo-xanthine (product is contaminated with approx. 20% 1-[2-(2-hydroxy-phenyl)-2-oxo-ethyl]-3-methyl-7-(3-bromo-2-buten-1-yl)-8-bromo-xanthine)

Mass spectrum (ESI$^+$): m/z=431, 433 [M+H]$^+$ (2) 1-[2-(2-hydroxy-phenyl)-2-oxo-ethyl]-3-methyl-7-[(1-cyclopenten-1-yl)methyl]-8-bromo-xanthine Mass spectrum (ESI$^+$): m/z=459, 461 [M+H]$^+$ (3) 1-[2-(2-hydroxy-phenyl)-2-oxo-ethyl]-3-methyl-7-((E)-2-buten-1-yl)-8-bromo-xanthine (product contains some Z isomer)

$R_f$ value: 0.60 (silica gel, cyclohexane/ethyl acetate=4:6)

Mass spectrum (ESI$^+$): m/z=433, 435 [M+H]$^+$ (4) 1-[2-(2-hydroxy-phenyl)-2-oxo-ethyl]-3-methyl-7-(3-methyl-2-buten-1-yl)-8-bromo-xanthine Mass spectrum (ESI$^+$): m/z=447, 449 [M+H]$^+$ Example V 1-[2-(2-methoxy-phenyl)-2-oxo-ethyl]-3-methyl-7-(3-methyl-2-buten-1-yl)-8-chloro-xanthine 1.71 g of 2-bromo-1-(2-methoxy-phenyl)-ethanone are added to a mixture of 2.00 g of 3-methyl-7-(3-methyl-2-buten-1-yl)-8-chloro-xanthine and 1.38 mg of potassium carbonate in 15 ml of N,N-dimethylformamide. The reaction mixture is stirred for eight hours at ambient temperature. After aqueous working up the crude product is purified by chromatography through a silica gel column with cyclohexane/ethyl acetate (8:1 to 8:1) as eluant.

Yield: 2.61 g (84% of theory)

Mass spectrum (ESI$^+$): m/z=417, 419 [M+H]$^+$

The following compounds are obtained analogously to Example V:

(1) 1-[2-(3-hydroxy-phenyl)-2-oxo-ethyl]-3-methyl-7-(3-methyl-2-buten-1-yl)-8-[3-(tert.-butyloxycarbonylamino)-piperidin-1-yl]-xanthine (The reaction is carried out with 2-bromo-1-[3-(tert.-butyldimethylsilanyloxy)-phenyl]-ethanone)

$R_f$ value: 0.40 (silica gel, cyclohexane/ethyl acetate=3:7)

Mass spectrum (ESI$^+$): m/z=567 [M+H]$^+$ (2) 1-(1-methyl-2-oxo-2-phenyl-ethyl)-3-methyl-7-(3-methyl-2-buten-1-yl)-8-chloro-xanthine Mass spectrum (ESI$^+$): m/z=401, 403 [M+H]$^+$ (3) 1-(2-cyano-ethyl)-3-methyl-7-(2-cyano-benzyl)-8-chloro-xanthine Mass spectrum (ESI$^+$): m/z=391, 393 [M+Na]$^+$ (4) 1-(2-phenoxy-ethyl)-3-methyl-7-(2-cyano-benzyl)-8-[3-(tert.-butyloxycarbonylamino)-piperidin-1-yl]-xanthine $R_f$ value: 0.90 (silica gel, methylene chloride/methanol=9:1)

Mass spectrum (ESI$^+$): m/z=600 [M+H]$^+$ (5) 1-(2-phenyl-2-oxo-ethyl)-3-[(2-trimethylsilanyl-ethoxy)methyl]-7-(3-methyl-2-buten-1-yl)-8-[3-(tert.-butyloxycarbonylamino)-piperidin-1-yl]-xanthine Mass spectrum (ESI$^+$): m/z=667 [M+H]$^+$ (6) 1-(2-methoxy-ethyl)-3-methyl-7-(2-cyano-benzyl)-8-[3-(tert.-butyloxycarbonylamino)-piperidin-1-yl]-xanthine $R_f$ value: 0.90 (silica gel, methylene chloride/methanol=9:1)

Mass spectrum (ESI$^+$): m/z=538 [M+H]$^+$ (7) 1-methyl-3-[(2-trimethylsilanyl-ethoxy)methyl]-7-(2-cyano-benzyl)-xanthine $R_f$ value: 0.60 (silica gel, cyclohexane/ethyl acetate=1:1)

Mass spectrum (ESI$^+$): m/z=412 [M+H]$^+$ (8) 1-[2-(3-nitro-phenyl)-2-oxo-ethyl]-3-methyl-7-(3-methyl-2-buten-1-yl)-8-chloro-xanthine $R_f$ value: 0.40 (silica gel, cyclohexane/ethyl acetate/methanol=7:2:1)

Mass spectrum (ESI$^+$): m/z=432, 434 [M+H]$^+$ (9) 1-(2-phenyl-2-oxo-ethyl)-3-methyl-7-[(2-trimethylsilanyl-ethoxy)methyl]-8-bromo-xanthine Mass spectrum (ESI$^+$): m/z=493, 495 [M+H]$^+$

(10) 1-[2-(2-nitro-phenyl)-2-oxo-ethyl]-3-methyl-7-(3-methyl-2-buten-1-yl)-8-chloro-xanthine $R_f$ value: 0.64 (silica gel, cyclohexane/ethyl acetate=3:7)

Mass spectrum (ESI$^+$): m/z=432, 434 [M+H]$^+$

(11) 1-[2-(2-nitro-phenyl)-2-oxo-ethyl]-3-methyl-7-(3-methyl-2-buten-1-yl)-8-bromo-xanthine Mass spectrum (ESI$^+$): m/z=476, 478 [M+H]$^+$

(12) 1-[(quinolin-2-yl)methyl]-3-methyl-7-(3-methyl-2-buten-1-yl)-8-[3-(tert.-butyloxycarbonylamino)-piperidin-1-yl]-xanthine $R_f$ value: 0.45 (silica gel, ethyl acetate/petroleum ether=7:3)

Mass spectrum (ESI$^+$): m/z=574 [M+H]$^+$

(13) 1-[(2-oxo-2H-chromen-4-yl)methyl]-3-methyl-7-(3-methyl-2-buten-1-yl)-8-[3-(tert.-butyloxycarbonylamino)-piperidin-1-yl]-xanthine (The starting material 4-bromomethyl-chromen-2-one is prepared analogously to Kimura et al., *Chem. Pharm. Bull.* 1982, 30, 552-558.)

$R_f$ value: 0.52 (silica gel, methylene chloride/methanol=95:5)

Mass spectrum (ESI$^+$): m/z=591 [M+H]$^+$

(14) 1-[(1-methyl-2-oxo-1,2-dihydro-quinolin-4-yl)methyl]-3-methyl-7-(3-methyl-2-buten-1-yl)-8-[3-(tert.-butyloxycarbonylamino)-piperidin-1-yl]-xanthine $R_f$ value: 0.54 (silica gel, methylene chloride/methanol=95:5)

Mass spectrum (ESI$^+$): m/z=604 [M+H]$^+$

(15) 1-[(quinazolin-4-yl)methyl]-3-methyl-7-(3-methyl-2-buten-1-yl)-8-[3-(tert.-butyloxycarbonylamino)-piperidin-1-yl]-xanthine Melting point: 195-197° C.

Mass spectrum (ESI$^+$): m/z=575 [M+H]$^+$

(16) 1-[(5-methyl-3-phenyl-isoxazol-4-yl)methyl]-3-methyl-7-(3-methyl-2-buten-1-yl)-8-[3-(tert.-butyloxycarbonylamino)-piperidin-1-yl]-xanthine
$R_f$ value: 0.40 (silica gel, cyclohexane/ethyl acetate=1:1)
Mass spectrum (ESI$^+$): m/z=604 [M+H]$^+$

(17) 1-[(3-phenyl-[1,2,4]oxadiazol-5-yl)methyl]-3-methyl-7-(3-methyl-2-buten-1-yl)-8-[3-(tert.-butyloxycarbonylamino)-piperidin-1-yl]-xanthine
$R_f$ value: 0.18 (silica gel, petroleum ether/ethyl acetate=2:1)
Mass spectrum (ESI$^+$): m/z=591 [M+H]$^+$

(18) 1-[(4-phenyl-pyridin-2-yl)methyl]-3-methyl-7-(3-methyl-2-buten-1-yl)-8-[3-(tert.-butyloxycarbonylamino)-piperidin-1-yl]-xanthine
$R_f$ value: 0.53 (silica gel, methylene chloride/methanol=95:5)
Mass spectrum (ESI$^+$): m/z=600 [M+H]$^+$

(19) 1-[(5-phenyl-pyridin-2-yl)methyl]-3-methyl-7-(3-methyl-2-buten-1-yl)-8-[3-(tert.-butyloxycarbonylamino)-piperidin-1-yl]-xanthine
$R_f$ value: 0.73 (silica gel, ethyl acetate)
Mass spectrum (ESI$^+$): m/z=600 [M+H]$^+$

(20) 1-[2-(3-methylsulphanyl-phenyl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.43 (silica gel, cyclohexane/ethyl acetate=1:1)
Mass spectrum (ESI$^+$): m/z=597 [M+H]$^+$

(21) 1-[2-(3-methoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.27 (silica gel, methylene chloride/methanol=20:1)
Mass spectrum (ESI$^+$): m/z=609 [M+H]$^+$

(22) 1-[2-(2-ethoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.35 (silica gel, methylene chloride/methanol=20:1)
Mass spectrum (ESI$^+$): m/z=623 [M+H]$^+$

(23) 1-[2-(2,6-dimethoxy-phenyl)-2-oxo-ethyl]-3-methyl-7-(3-methyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.53 (silica gel, methylene chloride/methanol=20:1)
Mass spectrum (ESI$^+$): m/z=611 [M+H]$^+$

(24) 1-(2-phenyl-2-oxo-ethyl)-3-methyl-7-(2,3-dimethyl-2-buten-1-yl)-8-[3-(tert.-butyloxycarbonylamino)-piperidin-1-yl]-xanthine
(Carried out in N-methylpyrrolidin-2-one at 60° C.)
$R_f$ value: 0.38 (silica gel, methylene chloride/methanol=20:1)
Mass spectrum (ESI$^+$): m/z=565 [M+H]$^+$

(25) 1-((E)-3-phenyl-allyl)-3-methyl-7-(3-methyl-2-buten-1-yl)-8-[3-(tert.-butyloxycarbonylamino)-piperidin-1-yl]-xanthine
$R_f$ value: 0.54 (silica gel, methylene chloride/methanol/conc. aqueous ammonia=95:5:0.1)
Mass spectrum (ESI$^+$): m/z=549 [M+H]$^+$

(26) 1-[(1-benzo[b]thiophen-3-yl)methyl]-3-methyl-7-(3-methyl-2-buten-1-yl)-8-[3-(tert.-butyloxycarbonylamino)-piperidin-1-yl]-xanthine
$R_f$ value: 0.75 (silica gel, methylene chloride/methanol=95:5)
Mass spectrum (ESI$^+$): m/z=579 [M+H]$^+$

(27) 1-{[1-(tert.-butyloxycarbonyl)-indol-3-yl]methyl}-3-methyl-7-(3-methyl-2-buten-1-yl)-8-[3-(tert.-butyloxycarbonylamino)-piperidin-1-yl]-xanthine
$R_f$ value: 0.61 (silica gel, methylene chloride/methanol=9:1)
Mass spectrum (ESI$^+$): m/z=662 [M+H]$^+$

(28) 1-[(biphenyl-4-yl)methyl]-3-methyl-7-(3-methyl-2-buten-1-yl)-8-[3-(tert.-butyloxycarbonylamino)-piperidin-1-yl]-xanthine
$R_f$ value: 0.68 (silica gel, cyclohexane/ethyl acetate=1:1)
Mass spectrum (ESI$^+$): m/z=599 [M+H]$^+$

(29) 1-[(1-naphthyl)methyl]-3-methyl-7-(2-butyn-1-yl)-8-[3-(tert.-butyloxycarbonylamino)-piperidin-1-yl]-xanthine
$R_f$ value: 0.83 (silica gel, ethyl acetate/petroleum ether=4:1)
Mass spectrum (ESI$^+$): m/z=557 [M+H]$^+$

(30) 1-[(1-methyl-2-oxo-1,2-dihydro-quinolin-4-yl)methyl]-3-methyl-7-(2-butyn-1-yl)-8-[3-(tert.-butyloxycarbonylamino)-piperidin-1-yl]-xanthine
$R_f$ value: 0.25 (silica gel, ethyl acetate/petroleum ether=4:1)
Mass spectrum (ESI$^+$): m/z=588 [M+H]$^+$

(31) 1-(2-cyclohexyl-2-oxo-ethyl)-3-methyl-7-(3-methyl-2-buten-1-yl)-8-[3-(tert.-butyloxycarbonylamino)-piperidin-1-yl]-xanthine
Melting point: 163-165° C.
Mass spectrum (ESI$^+$): m/z=557 [M+H]$^+$

(32) 1-(3,3-dimethyl-2-oxo-butyl)-3-methyl-7-(3-methyl-2-buten-1-yl)-8-[3-(tert.-butyloxycarbonylamino)-piperidin-1-yl]-xanthine
$R_f$ value: 0.95 (silica gel, ethyl acetate/petroleum ether=4:1)
Mass spectrum (ESI$^+$): m/z=531 [M+H]$^+$

(33) 1-[(quinazolin-2-yl)methyl]-3-methyl-7-(2-butyn-1-yl)-8-[3-(tert.-butyloxycarbonylamino)-piperidin-1-yl]-xanthine
$R_f$ value: 0.40 (silica gel, ethyl acetate)
Mass spectrum (ESI$^+$): m/z=559 [M+H]$^+$

(34) 1-[(2-methyl-naphthalen-1-yl)methyl]-3-methyl-7-(2-butyn-1-yl)-8-[3-(tert.-butyloxycarbonylamino)-piperidin-1-yl]-xanthine
$R_f$ value: 0.80 (silica gel, ethyl acetate)
Mass spectrum (ESI$^+$): m/z=571 [M+H]$^+$

(35) 1-[(5-nitro-isoquinolin-1-yl)methyl]-3-methyl-7-(3-methyl-2-buten-1-yl)-8-[3-(tert.-butyloxycarbonylamino)-piperidin-1-yl]-xanthine
$R_f$ value: 0.54 (silica gel, methylene chloride/methanol=95:5)

(36) 1-(2-dimethylamino-2-oxo-ethyl)-3-methyl-7-(3-methyl-2-buten-1-yl)-8-[3-(tert.-butyloxycarbonylamino)-piperidin-1-yl]-xanthine
$R_f$ value: 0.23 (silica gel, ethyl acetate)
Mass spectrum (ESI$^+$): m/z=518 [M+H]$^+$

(37) 1-[2-(piperidin-1-yl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.44 (silica gel, ethyl acetate)
Mass spectrum (ESI$^+$): m/z=558 [M+H]$^+$

(38) 1-[(2-methyl-1-oxo-1,2-dihydro-isoquinolin-4-yl)methyl]-7-(2-butyn-1-yl)-8-[3-(tert.-butyloxycarbonylamino)-piperidin-1-yl]-xanthine
$R_f$ value: 0.25 (silica gel, ethyl acetate)
Mass spectrum (ESI$^+$): m/z=588 [M+H]$^+$

(39) 1-[(2-methyl-1-oxo-1,2-dihydro-isoquinolin-4-yl)methyl]-7-(3-methyl-2-buten-1-yl)-8-[3-(tert.-butyloxycarbonylamino)-piperidin-1-yl]-xanthine $R_f$ value: 0.30 (silica gel, ethyl acetate)
Mass spectrum (ESI⁺): m/z=604 [M+H]⁺

(40) 1-[(2-methoxy-naphthalen-1-yl)methyl]-3-methyl-7-(2-butyn-1-yl)-8-[3-(tert.-butyloxycarbonylamino)-piperidin-1-yl]-xanthine
$R_f$ value: 0.75 (silica gel, ethyl acetate)
Mass spectrum (ESI⁺): m/z=587 [M+H]⁺

(41) 1-[(4-methoxy-naphthalen-1-yl)methyl]-3-methyl-7-(2-butyn-1-yl)-8-[3-(tert.-butyloxycarbonylamino)-piperidin-1-yl]-xanthine
$R_f$ value: 0.80 (silica gel, ethyl acetate)
Mass spectrum (ESI⁺): m/z=587 [M+H]⁺

(42) 1-[(3-methyl-isoquinolin-1-yl)methyl]-3-methyl-7-(2-butyn-1-yl)-8-[3-(tert.-butyloxycarbonylamino)-piperidin-1-yl]-xanthine
$R_f$ value: 0.56 (silica gel, methylene chloride/methanol=95:5)
Mass spectrum (ESI⁺): m/z=572 [M+H]⁺

(43) 1-[2-(2,3-dimethoxy-phenyl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.83 (silica gel, ethyl acetate)
Mass spectrum (ESI⁺): m/z=611 [M+H]⁺

(44) 1-[(5-nitro-naphthalen-1-yl)methyl]-3-methyl-7-(2-butyn-1-yl)-8-[3-(tert.-butyloxycarbonylamino)-piperidin-1-yl]-xanthine
$R_f$ value: 0.78 (silica gel, ethyl acetate)
Mass spectrum (ESI⁺): m/z=602 [M+H]⁺

(45) 1-[2-(pyrrolidin-1-yl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.39 (silica gel, ethyl acetate)
Mass spectrum (ESI⁺): m/z=544 [M+H]⁺

(46) 1-[(4-methyl-isoquinolin-1-yl)methyl]-3-methyl-7-(2-butyn-1-yl)-8-[3-(tert.-butyloxycarbonylamino)-piperidin-1-yl]-xanthine
$R_f$ value: 0.56 (silica gel, methylene chloride/methanol=95:5)
Mass spectrum (ESI⁺): m/z=572 [M+H]⁺

(47) 1-[(2-naphthyl)methyl]-3-methyl-7-(2-butyn-1-yl)-8-[3-(tert.-butyloxycarbonylamino)-piperidin-1-yl]-xanthine
$R_f$ value: 0.78 (silica gel, ethyl acetate)
Mass spectrum (ESI⁺): m/z=557 [M+H]⁺

(48) 1-cyanomethyl-3-methyl-7-(2-butyn-1-yl)-8-[3-(tert.-butyloxycarbonyl-amino)-piperidin-1-yl]-xanthine
$R_f$ value: 0.80 (silica gel, ethyl acetate)
Mass spectrum (ESI⁺): m/z=456 [M+H]⁺

(49) 1-[(quinolin-6-yl)methyl]-3-methyl-7-(2-butyn-1-yl)-8-[3-(tert.-butyloxycarbonylamino)-piperidin-1-yl]-xanthine
$R_f$ value: 0.40 (silica gel, ethyl acetate)
Mass spectrum (ESI⁺): m/z=558 [M+H]⁺

(50) 1-[(3-methoxy-naphthalen-2-yl)methyl]-3-methyl-7-(2-butyn-1-yl)-8-[3-(tert.-butyloxycarbonylamino)-piperidin-1-yl]-xanthine
$R_f$ value: 0.83 (silica gel, ethyl acetate)
Mass spectrum (ESI⁺): m/z=587 [M+H]⁺

(51) 1-[2-(2,3-dihydro-benzo[1,4]dioxin-5-yl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.38 (silica gel, ethyl acetate/petroleum ether=1:1)
Mass spectrum (ESI⁺): m/z=609 [M+H]⁺

(52) 1-[2-(3-methyl-2-oxo-2,3-dihydro-benzooxazol-7-yl)-2-oxo-ethyl]-3-methyl-7-(3-methyl-2-buten-1-yl)-8-[3-(tert.-butyloxycarbonylamino)-piperidin-1-yl]-xanthine
(Carried out with potassium-tert.butoxide in dimethylsulphoxide)
$R_f$ value: 0.48 (silica gel, ethyl acetate/petroleum ether=2:1)
Mass spectrum (ESI⁺): m/z=622 [M+H]⁺

(53) 1-[2-(benzo[1,3]dioxol-4-yl)-2-oxo-ethyl]-3-methyl-7-(3-methyl-2-buten-1-yl)-8-[3-(tert.-butyloxycarbonylamino)-piperidin-1-yl]-xanthine
Mass spectrum (ESI⁺): m/z=595 [M+H]⁺

(54) 1-[(quinazolin-2-yl)methyl]-3-methyl-7-(2-butyn-1-yl)-8-[(R)-3-(tert.-butyloxycarbonylamino)-piperidin-1-yl]-xanthine
Mass spectrum (ESI⁺): m/z=559 [M+H]⁺

(55) 1-[(quinazolin-2-yl)methyl]-3-methyl-7-(2-butyn-1-yl)-8-[(S)-3-(tert.-butyloxycarbonylamino)-piperidin-1-yl]-xanthine
Mass spectrum (ESI⁺): m/z=559 [M+H]⁺

(56) 1-[(quinazolin-2-yl)methyl]-3-methyl-7-((E)-2-buten-1-yl)-8-[(S)-3-(tert.-butyloxycarbonylamino)-piperidin-1-yl]-xanthine
(product contains approx. 15% of Z isomer)
$R_f$ value: 0.30 (silica gel, ethyl acetate/cyclohexane=8:2)
Mass spectrum (ESI⁺): m/z=561 [M+H]⁺

(57) 1-[(quinazolin-2-yl)methyl]-3-methyl-7-((E)-2-buten-1-yl)-8-[(R)-3-(tert.-butyloxycarbonylamino)-piperidin-1-yl]-xanthine
(product contains approx. 15% of Z isomer)
$R_f$ value: 0.30 (silica gel, ethyl acetate/cyclohexane=8:2)
Mass spectrum (ESI⁺): m/z=561 [M+H]⁺

(58) 1-[(3-methyl-isoquinolin-1-yl)methyl]-3-methyl-7-((E)-2-buten-1-yl)-8-[(R)-3-(tert.-butyloxycarbonylamino)-piperidin-1-yl]-xanthine
(product contains approx. 17% of Z isomer)
$R_f$ value: 0.58 (silica gel, methylene chloride/methanol=95:5)
Mass spectrum (ESI⁺): m/z=574 [M+H]⁺

(59) 1-[(3-methyl-isoquinolin-1-yl)methyl]-3-methyl-7-((E)-2-buten-1-yl)-8-[(S)-3-(tert.-butyloxycarbonylamino)-piperidin-1-yl]-xanthine
(product contains approx. 17% of Z isomer)
$R_f$ value: 0.58 (silica gel, methylene chloride/methanol=95:5)
Mass spectrum (ESI⁺): m/z=574 [M+H]⁺

(60) 1-[2-(2-methoxy-phenyl)-2-oxo-ethyl]-3-methyl-7-(2-butyn-1-yl)-8-bromo-xanthine
Mass spectrum (ESI⁺): m/z=445, 447 [M+H]⁺

(61) 1-[2-(2-nitro-phenyl)-2-oxo-ethyl]-3-methyl-7-[(1-cyclopenten-1-yl)methyl]-8-bromo-xanthine
Mass spectrum (ESI⁺): m/z=488, 490 [M+H]⁺

(62) 1-[2-(2-methoxy-phenyl)-2-oxo-ethyl]-3-methyl-7-[(1-cyclopenten-1-yl)methyl]-8-bromo-xanthine
Mass spectrum (ESI⁺): m/z=473, 475 [M+H]⁺

(63) 1-[(isoquinolin-1-yl)methyl]-3-[(methoxycarbonyl)methyl]-7-(3-methyl-2-buten-1-yl)-8-[3-(tert.-butyloxycarbonylamino)-piperidin-1-yl]-xanthine
$R_f$ value: 0.35 (silica gel, methylene chloride/methanol=95:5)

(64) 1-[2-(2-nitro-phenyl)-2-oxo-ethyl]-3-methyl-7-((E)-2-buten-1-yl)-8-bromo-xanthine
(product contains approx. 10% of Z isomer)
$R_f$ value: 0.60 (silica gel, cyclohexane/ethyl acetate=4:6)
Mass spectrum (ESI⁺): m/z=462, 464 [M+H]⁺

(65) 1-[2-(2-methoxy-phenyl)-2-oxo-ethyl]-3-methyl-7-((E)-2-buten-1-yl)-8-bromo-xanthine
(product contains some Z isomer)
$R_f$ value: 0.30 (silica gel, cyclohexane/ethyl acetate=1:1)
Mass spectrum (ESI$^+$): m/z=447, 449 [M+H]$^+$

(66) 1-[2-(2-nitro-phenyl)-2-oxo-ethyl]-3-methyl-7-(2-butyn-1-yl)-8-bromo-xanthine
$R_f$ value: 0.77 (silica gel, methylene chloride/methanol=95:5)
Mass spectrum (ESI$^+$): m/z=460, 462 [M+H]$^+$

(67) 1-(2-phenyl-2-oxo-ethyl)-3-methyl-7-((E)-2-buten-1-yl)-8-[(R)-3-(tert.-butyloxycarbonylamino)-piperidin-1-yl]-xanthine
(product contains approx. 20% of Z isomer)
Mass spectrum (ESI$^+$): m/z=537 [M+H]$^+$

(68) 1-[2-(2-methoxy-phenyl)-2-oxo-ethyl]-3-methyl-7-(3-methyl-2-buten-1-yl)-8-bromo-xanthine
Mass spectrum (ESI$^+$): m/z=461, 463 [M+H]$^+$

(69) 1-(2-phenyl-2-oxo-ethyl)-3-methyl-7-(2-butyn-1-yl)-8-bromo-xanthine
$R_f$ value: 0.61 (silica gel, cyclohexane/ethyl acetate=4:6)

(70) 1-(2-{2-[(ethylaminocarbonyl)methoxy]-phenyl}-2-oxo-ethyl)-3-methyl-7-((E)-2-buten-1-yl)-8-[(R)-3-(tert.-butyloxycarbonylamino)-piperidin-1-yl]-xanthine
(product contains approx. 17% of Z isomer)
Mass spectrum (ESI$^+$): m/z=638 [M+H]$^+$

(71) 1-(2-phenyl-2-oxo-ethyl)-3-methyl-7-((E)-2-buten-1-yl)-8-[(S)-3-(tert.-butyloxycarbonylamino)-piperidin-1-yl]-xanthine
(product contains approx. 18% of Z isomer)
$R_f$ value: 0.35 (silica gel, cyclohexane/ethyl acetate=6:4)
Mass spectrum (ESI$^+$): m/z=537 [M+H]$^+$

(72) 1-[2-(2-nitro-phenyl)-2-oxo-ethyl]-3-methyl-7-(2-butyn-1-yl)-8-[(S)-3-(tert.-butyloxycarbonylamino)-piperidin-1-yl]-xanthine
$R_f$ value: 0.60 (silica gel, methylene chloride/methanol=95:5)
Mass spectrum (ESI$^+$): m/z=580 [M+H]$^+$

(73) 1-[(3-methyl-isoquinolin-1-yl)methyl]-3-methyl-7-(2-butyn-1-yl)-8-[(S)-3-(tert.-butyloxycarbonylamino)-piperidin-1-yl]-xanthine
$R_f$ value: 0.52 (silica gel, methylene chloride/methanol=95:5)
Mass spectrum (ESI$^+$): m/z=572 [M+H]$^+$

(74) 1-[(3-methyl-isoquinolin-1-yl)methyl]-3-methyl-7-(2-butyn-1-yl)-8-[(R)-3-(tert.-butyloxycarbonylamino)-piperidin-1-yl]-xanthine
Mass spectrum (ESI$^+$): m/z=572 [M+H]$^+$

(75) 1-[(4-methyl-isoquinolin-1-yl)methyl]-3-methyl-7-(2-butyn-1-yl)-8-[(S)-3-(tert.-butyloxycarbonylamino)-piperidin-1-yl]-xanthine
Mass spectrum (ESI$^+$): m/z=572 [M+H]$^+$

(76) 1-[(4-methyl-isoquinolin-1-yl)methyl]-3-methyl-7-(2-butyn-1-yl)-8-[(R)-3-(tert.-butyloxycarbonylamino)-piperidin-1-yl]-xanthine
Mass spectrum (ESI$^+$): m/z=572 [M+H]$^+$

(77) 1-[(4-methyl-isoquinolin-1-yl)methyl]-3-methyl-7-((E)-2-buten-1-yl)-8-[(S)-3-(tert.-butyloxycarbonylamino)-piperidin-1-yl]-xanthine
$R_f$ value: 0.52 (silica gel, methylene chloride/methanol=95:5)
Mass spectrum (ESI$^+$): m/z=574 [M+H]$^+$

(78) 1-[(4-methyl-isoquinolin-1-yl)methyl]-3-methyl-7-((E)-2-buten-1-yl)-8-[(R)-3-(tert.-butyloxycarbonylamino)-piperidin-1-yl]-xanthine
$R_f$ value: 0.52 (silica gel, methylene chloride/methanol=95:5)
Mass spectrum (ESI$^+$): m/z=574 [M+H]$^+$

(79) 1-[2-(2,3-dihydro-benzo[1,4]dioxin-5-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.18 (silica gel, ethyl acetate/petroleum ether=1:1)
Mass spectrum (ESI$^+$): m/z=593 [M+H]$^+$

(80) 1-[2-(2,3-dihydro-benzo[1,4]dioxin-5-yl)-2-oxo-ethyl]-3-methyl-7-(2-butyn-1-yl)-8-[(S)-3-(tert.-butyloxycarbonylamino)-piperidin-1-yl]-xanthine
Mass spectrum (ESI$^+$): m/z=593 [M+H]$^+$

(81) 1-[(4-methoxy-naphthalen-1-yl)methyl]-3-methyl-7-(2-butyn-1-yl)-8-[(S)-3-(tert.-butyloxycarbonylamino)-piperidin-1-yl]-xanthine
$R_f$ value: 0.56 (silica gel, petroleum ether/ethyl acetate=1:2)
Mass spectrum (ESI$^+$): m/z=587 [M+H]$^+$

(82) 1-[(4-methoxy-naphthalen-1-yl)methyl]-3-methyl-7-(2-butyn-1-yl)-8-[(R)-3-(tert.-butyloxycarbonylamino)-piperidin-1-yl]-xanthine
Mass spectrum (ESI$^+$): m/z=587 [M+H]$^+$

(83) 1-[2-(benzo[1,3]dioxol-4-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.86 (silica gel, ethyl acetate/petroleum ether=4:1)
Mass spectrum (ESI$^+$): m/z=579 [M+H]$^+$

(84) 1-[2-(benzo[1,3]dioxol-4-yl)-2-oxo-ethyl]-3-methyl-7-(2-butyn-1-yl)-8-[(S)-3-(tert.-butyloxycarbonylamino)-piperidin-1-yl]-xanthine
$R_f$ value: 0.86 (silica gel, ethyl acetate/petroleum ether=4:1)
Mass spectrum (ESI$^+$): m/z=579 [M+H]$^+$

(85) 1-[(4-methyl-quinazolin-2-yl)methyl]-3-methyl-7-(2-butyn-1-yl)-8-[(S)-3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=573 [M+H]$^+$

(86) 1-[(4-methyl-quinazolin-2-yl)methyl]-3-methyl-7-(2-butyn-1-yl)-8-[(R)-3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=573 [M+H]$^+$

(87) 1-[2-(3-methyl-2-oxo-2,3-dihydro-benzooxazol-4-yl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.50 (silica gel, petroleum ether/ethyl acetate=1:2)
Mass spectrum (ESI$^+$): m/z=622 [M+H]$^+$

(88) 1-(2-{2-[(ethylaminocarbonyl)methoxy]-phenyl}-2-oxo-ethyl)-3-methyl-7-((E)-2-buten-1-yl)-8-[(S)-3-(tert.-butyloxycarbonylamino)-piperidin-1-yl]-xanthine
Mass spectrum (ESI$^+$): m/z=638 [M+H]$^+$

(89) 1-(2-{2-[(methylaminocarbonyl)methoxy]-phenyl}-2-oxo-ethyl)-3-methyl-7-((E)-2-buten-1-yl)-8-[(R)-3-(tert.-butyloxycarbonylamino)-piperidin-1-yl]-xanthine
Mass spectrum (ESI$^+$): m/z=624 [M+H]$^+$

(90) 1-(2-{2-[(methylaminocarbonyl)methoxy]-phenyl}-2-oxo-ethyl)-3-methyl-7-((E)-2-buten-1-yl)-8-[(S)-3-(tert.-butyloxycarbonylamino)-piperidin-1-yl]-xanthine
Mass spectrum (ESI$^+$): m/z=624 [M+H]$^+$

(91) 1-[2-(2-nitro-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.60 (silica gel, methylene chloride/methanol=95:5)

(92) 1-[2-(2-nitro-3-methoxy-phenyl)-2-oxo-ethyl]-3-methyl-7-(3-methyl-2-buten-1-yl)-8-bromo-xanthine
Mass spectrum (ESI$^+$): m/z=506, 508 [M+H]$^+$

(93) 1-[(4-dimethylamino-quinazolin-2-yl)methyl]-3-methyl-7-(2-butyn-1-yl)-8-[3-(tert.-butyloxycarbonylamino)-piperidin-1-yl]-xanthine
(Carried out in the presence of caesium carbonate)
$R_f$ value: 0.40 (silica gel, methylene chloride/methanol=95:5)
Mass spectrum (ESI$^+$): m/z=602 [M+H]$^+$

(94) 1-(2-{2-oxo-3-[(2-trimethylsilanyl-ethoxy)methyl]-2,3-dihydro-benzooxazol-7-yl}-2-oxo-ethyl)-3-methyl-7-(3-methyl-2-buten-1-yl)-8-bromo-xanthine
$R_f$ value: 0.75 (silica gel, ethyl acetate/petroleum ether=1:1)
Mass spectrum (ESI$^+$): m/z=618, 620 [M+H]$^+$

(95) 1-[(imidazo[1,2-a]pyridin-2-yl)methyl]-3-methyl-7-(2-butyn-1-yl)-8-[3-(tert.-butyloxycarbonylamino)-piperidin-1-yl]-xanthine
$R_f$ value: 0.44 (silica gel, methylene chloride/methanol=95:5)
Mass spectrum (ESI$^+$): m/z=547 [M+H]$^+$

(96) 1-[(quinoxalin-2-yl)methyl]-3-methyl-7-(2-butyn-1-yl)-8-[3-(tert.-butyloxycarbonyl-amino)-piperidin-1-yl]-xanthine
$R_f$ value: 0.50 (silica gel, methylene chloride/methanol=95:5)
Mass spectrum (ESI$^+$): m/z=559 [M+H]$^+$

(97) 1-[2-(1,3-dimethyl-2-oxo-2,3-dihydro-1H-benzoimidazol-4-yl)-2-oxo-ethyl]-3-methyl-7-(2-butyn-1-yl)-8-[3-(tert.-butyloxycarbonylamino)-piperidin-1-yl]-xanthine
$R_f$ value: 0.50 (silica gel, methylene chloride/methanol=95:5)
Mass spectrum (ESI$^+$): m/z=619 [M+H]$^+$

(98) 1-[(quinoxalin-6-yl)methyl]-3-methyl-7-(2-butyn-1-yl)-8-[3-(tert.-butyloxycarbonylamino)-piperidin-1-yl]-xanthine
$R_f$ value: 0.35 (silica gel, ethyl acetate)
Mass spectrum (ESI$^+$): m/z=559 [M+H]$^+$

(99) 1-(2-{2-oxo-3-[(2-trimethylsilanyl-ethoxy)methyl]-2,3-dihydro-benzooxazol-4-yl}-2-oxo-ethyl)-3-methyl-7-(2-butyn-1-yl)-8-bromo-xanthine
$R_f$ value: 0.30 (silica gel, petroleum ether/ethyl acetate=2:1)
Mass spectrum (ESI$^-$): m/z=600, 602 [M−H]$^-$ (100) 1-[(3-methyl-quinoxalin-2-yl)methyl]-3-methyl-7-(2-butyn-1-yl)-8-[3-(tert.-butyloxycarbonylamino)-piperidin-1-yl]-xanthine
$R_f$ value: 0.44 (silica gel, petroleum ether/ethyl acetate=1:2)
Mass spectrum (ESI$^+$): m/z=573 [M+H]$^+$ (101) 1-[(3-phenyl-isoquinolin-1-yl)methyl]-3-methyl-7-(2-butyn-1-yl)-8-[3-(tert.-butyloxycarbonylamino)-piperidin-1-yl]-xanthine
$R_f$ value: 0.85 (silica gel, ethyl acetate)
Mass spectrum (ESI$^+$): m/z=634 [M+H]$^+$ (102) 1-[(3,4-dimethyl-isoquinolin-1-yl)methyl]-3-methyl-7-(2-butyn-1-yl)-8-[3-(tert.-butyloxycarbonylamino)-piperidin-1-yl]-xanthine
$R_f$ value: 0.60 (silica gel, ethyl acetate/methanol=3:1)
Mass spectrum (ESI$^+$): m/z=586 [M+H]$^+$ (103) 1-[(benzofuran-2-yl)methyl]-3-methyl-7-(2-butyn-1-yl)-[(R)-3-(tert.-butyl-oxycarbonylamino)-piperidin-1-yl]-xanthine
Mass spectrum (ESI$^+$): m/z=547 [M+H]$^+$ (104) 1-{[4-(morpholin-4-yl)-quinazolin-2-yl]methyl}-3-methyl-7-(2-butyn-1-yl)-8-[3-(tert.-butyloxycarbonylamino)-piperidin-1-yl]-xanthine
(Carried out in the presence of caesium carbonate)
$R_f$ value: 0.28 (silica gel, ethyl acetate)
Mass spectrum (ESI$^+$): m/z=644 [M+H]$^+$ (105) 1-{[4-(piperidin-1-yl)-quinazolin-2-yl]methyl}-3-methyl-7-(2-butyn-1-yl)-8-[3-(tert.-butyloxycarbonylamino)-piperidin-1-yl]-xanthine
(Carried out in the presence of caesium carbonate)
$R_f$ value: 0.35 (silica gel, ethyl acetate)
Mass spectrum (ESI$^+$): m/z=642 [M+H]$^+$ (106) 1-({4-[4-(tert.-butyloxycarbonyl)-piperazin-1-yl]-quinazolin-2-yl}methyl)-3-methyl-7-(2-butyn-1-yl)-8-[3-(tert.-butyloxycarbonylamino)-piperidin-1-yl]-xanthine
(Carried out in the presence of caesium carbonate)
$R_f$ value: 0.50 (silica gel, ethyl acetate)
Mass spectrum (ESI$^+$): m/z=743 [M+H]$^+$ (107) 1-{[4-(pyrrolidin-1-yl)-quinazolin-2-yl]methyl}-3-methyl-7-(2-butyn-1-yl)-8-[3-(tert.-butyloxycarbonylamino)-piperidin-1-yl]-xanthine
(Carried out in the presence of caesium carbonate)
$R_f$ value: 0.59 (silica gel, ethyl acetate/methanol/conc. aqueous ammonia=95:5:0.1)
Mass spectrum (ESI$^+$): m/z=628 [M+H]$^+$ (108) 1-[2-(1-ethoxycarbonyl-3-methyl-2-oxo-2,3-dihydro-1H-benzoimidazol-4-yl)-2-oxo-ethyl]-3-methyl-7-(2-butyn-1-yl)-8-[3-(tert.-butyloxycarbonylamino)-piperidin-1-yl]-xanthine
$R_f$ value: 0.25 (silica gel, petroleum ether/ethyl acetate=1:2)
Mass spectrum (ESI$^+$): m/z=677 [M+H]$^+$ (109) 1-[(4-cyano-naphthalen-1-yl)methyl]-3-methyl-7-(2-butyn-1-yl)-8-[(R)-3-(tert.-butyloxycarbonylamino)-piperidin-1-yl]-xanthine
$R_f$ value: 0.77 (silica gel, methylene chloride/methanol/conc. aqueous ammonia=90:10:1)
Mass spectrum (ESI$^+$): m/z=582 [M+H]$^+$ (110) 1-[(imidazo[1,2-a]pyridine-3-yl)methyl]-3-methyl-7-(2-butyn-1-yl)-8-[3-(tert.-butyloxycarbonylamino)-piperidin-1-yl]-xanthine
Mass spectrum (ESI$^+$): m/z=547 [M+H]$^+$ (111) 1-[(8-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine
$R_f$ value: 0.25 (silica gel, ethyl acetate)
Mass spectrum (ESI$^+$): m/z=561 [M+H]$^+$ (112) 1-[(8-methoxy-quinolin-5-yl)methyl]-3-methyl-7-(2-butyn-1-yl)-8-[3-(tert.-butyloxycarbonylamino)-piperidin-1-yl]-xanthine
$R_f$ value: 0.60 (silica gel, ethyl acetate/methanol=9:1)
Mass spectrum (ESI$^+$): m/z=588 [M+H]$^+$ (113) 1-[(5-methoxy-quinolin-8-yl)methyl]-3-methyl-7-(2-butyn-1-yl)-8-[3-(tert.-butyloxycarbonylamino)-piperidin-1-yl]-xanthine
$R_f$ value: 0.40 (silica gel, methylene chloride/methanol=20:1)
Mass spectrum (ESI$^+$): m/z=588 [M+H]$^+$ (114) 1-[(4-phenyl-quinazolin-2-yl)methyl]-3-methyl-7-(2-butyn-1-yl)-8-[3-(tert.-butyloxycarbonylamino)-piperidin-1-yl]-xanthine
Mass spectrum (ESI$^+$): m/z=635 [M+H]$^+$ (115) 1-[(7-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, methylene chloride/methanol=95:5)

Mass spectrum (ESI⁺): m/z=561 [M+H]⁺

(116) 1-(2-oxo-4-phenyl-butyl)-3-methyl-7-(2-butyn-1-yl)-8-[(R)-3-(tert.-butyloxycarbonylamino)-piperidin-1-yl]-xanthine Mass spectrum (ESI⁺): m/z=563 [M+H]⁺

(117) 1-(2-{2-oxo-1,3-bis-[(2-trimethylsilanyl-ethoxy)methyl]-2,3-dihydro-1H-benzoimidazol-4-yl}-2-oxo-ethyl)-3-methyl-7-(2-butyn-1-yl)-8-[3-(tert.-butyloxy-carbonylamino)-piperidin-1-yl]-xanthine $R_f$ value: 0.50 (silica gel, ethyl acetate/petroleum ether=1:1)

Mass spectrum (ESI⁺): m/z=851 [M+H]⁺

(118) 1-[(3-difluoromethyl-isoquinolin-1-yl)methyl]-3-methyl-7-(2-butyn-1-yl)-8-[3-(tert.-butyloxycarbonylamino)-piperidin-1-yl]-xanthine (By-product of the reaction of 3-methyl-7-(2-butyn-1-yl)-8-[3-(tert.-butyloxy-carbonylamino)-piperidin-1-yl]-xanthine with 1-chloromethyl-3-trifluoromethyl-3,4-dihydro-isoquinoline)

$R_f$ value: 0.75 (aluminium oxide, petroleum ether/ethyl acetate=1:2)

Mass spectrum (ESI⁺): m/z=608 [M+H]⁺

(119) 1-[2-(2,2-difluoro-benzo[1,3]dioxol-4-yl)-2-oxo-ethyl]-3-methyl-7-(2-butyn-1-yl)-8-bromo-xanthine Mass spectrum (ESI⁺): m/z=495, 497 [M+H]⁺

(120) 1-[(3-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, methylene chloride/methanol=95:5)

Mass spectrum (ESI⁺): m/z=561 [M+H]⁺

(121) 1-[(5-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, methylene chloride/methanol/conc. aqueous ammonia=90:10:1)

Mass spectrum (ESI⁺): m/z=561 [M+H]⁺

(122) 1-[(6-methyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.10 (silica gel, ethyl acetate/methanol=98:2)

Mass spectrum (ESI⁺): m/z=561 [M+H]⁺

(123) 1-[(3-benzyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.60 (silica gel, methylene chloride/methanol=95:5)

Mass spectrum (ESI⁺): m/z=637 [M+H]⁺

(124) 1-[(4-isopropyl-quinazolin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, ethyl acetate/petroleum ether=8:2)

Mass spectrum (ESI⁺): m/z=601 [M+H]⁺

(125) 1-[(2,3-dihydro-benzo[1,4]dioxin-6-yl)methyl]-3-methyl-7-(2-butyn-1-yl)-8-[3-(tert.-butyloxycarbonylamino)-piperidin-1-yl]-xanthine $R_f$ value: 0.53 (silica gel, ethyl acetate/petroleum ether=3:2)

(126) 1-[(3-phenyl-imidazo[1,2-a]pyridin-2-yl)methyl]-3-methyl-7-(2-butyn-1-yl)-8-[3-(tert.-butyloxycarbonylamino)-piperidin-1-yl]-xanthine $R_f$ value: 0.50 (silica gel, methylene chloride/methanol=95:5)

Mass spectrum (ESI⁺): m/z=623 [M+H]⁺

(127) 1-[2-(naphthalen-1-yl)-2-oxo-ethyl]-3-methyl-7-(2-butyn-1-yl)-8-[3-(tert.-butyloxycarbonylamino)-piperidin-1-yl]-xanthine $R_f$ value: 0.54 (silica gel, methylene chloride/methanol=95:5)

Mass spectrum (ESI⁺): m/z=585 [M+H]⁺

(128) 1-[(5-methoxy-isoquinolin-8-yl)methyl]-3-methyl-7-(2-butyn-1-yl)-8-[3-(tert.-butyloxycarbonylamino)-piperidin-1-yl]-xanthine $R_f$ value: 0.50 (silica gel, ethyl acetate/methanol=24:1)

Mass spectrum (ESI⁺): m/z=588 [M+H]⁺

(129) 1-[(3-difluoromethyl-isoquinolin-1-yl)methyl]-3-methyl-7-(2-butyn-1-yl)-8-[3-(tert.-butyloxycarbonylamino)-piperidin-1-yl]-xanthine (By-product of the reaction of 3-methyl-7-(2-butyn-1-yl)-8-[3-(tert.-butyloxy-carbonylamino)-piperidin-1-yl]-xanthine with 1-chloromethyl-3-trifluoromethyl-3,4-dihydro-isoquinoline)

$R_f$ value: 0.75 (aluminium oxide, petroleum ether/ethyl acetate=1:2)

Mass spectrum (ESI⁺): m/z=608 [M+H]⁺

(130) 1-{[1-(1-cyano-1-methyl-ethyl)-isoquinolin-3-yl]methyl}-3-methyl-7-(2-butyn-1-yl)-8-[3-(tert.-butyloxycarbonylamino)-piperidin-1-yl]-xanthine $R_f$ value: 0.75 (silica gel, ethyl acetate)

Mass spectrum (ESI⁺): m/z=625 [M+H]⁺

(132) 1-methoxycarbonylmethyl-3-methyl-7-(2-butyn-1-yl)-8-[3-(tert.-butyloxycarbonyl-amino)-piperidin-1-yl]-xanthine Mass spectrum (ESI⁺): m/z=489 [M+H]⁺

(133) 1-[(4-phenyl-quinazolin-2-yl)methyl]-3-methyl-7-(2-butyn-1-yl)-8-[(R)-3-(tert.-butyloxycarbonylamino)-piperidin-1-yl]-xanthine Mass spectrum (ESI⁺): m/z=635 [M+H]⁺

(134) 1-[(2,3-dimethyl-quinoxalin-6-yl)methyl]-3-methyl-7-(2-butyn-1-yl)-8-[3-(tert.-butyloxycarbonylamino)-piperidin-1-yl]-xanthine (Carried out in the presence of caesium carbonate)

$R_f$ value: 0.40 (silica gel, ethyl acetate)

Mass spectrum (ESI⁺): m/z=587 [M+H]⁺

(135) 1-[(4-phenyl-quinazolin-2-yl)methyl]-3-methyl-7-(2-butyn-1-yl)-8-[(S)-3-(tert.-butyloxycarbonylamino)-piperidin-1-yl]-xanthine $R_f$ value: 0.55 (silica gel, ethyl acetate/petroleum ether=8:2)

Mass spectrum (ESI⁺): m/z=635 [M+H]⁺

(136) 1-[2-(quinolin-8-yl-]-2-oxo-ethyl]-3-methyl-7-(2-butyn-1-yl)-8-bromo-xanthine $R_f$ value: 0.55 (silica gel, methylene chloride/methanol=95:5)

Mass spectrum (ESI⁺): m/z=466, 468 [M+H]⁺

(137) 1-[(3,4-dimethyl-6,7-dihydro-5H-[2]pyrindin-1-yl)methyl]-3-methyl-7-(2-butyn-1-yl)-8-[3-(tert.-butyloxycarbonylamino)-piperidin-1-yl]-xanthine $R_f$ value: 0.65 (aluminium oxide, ethyl acetate/petroleum ether=3:1)

Mass spectrum (ESI⁺): m/z=576 [M+H]⁺

(138) 1-[(3,4-dimethyl-5,6,7,8-tetrahydro-isoquinolin-1-yl)methyl]-3-methyl-7-(2-butyn-1-yl)-8-[3-(tert.-butyloxycarbonylamino)-piperidin-1-yl]-xanthine $R_f$ value: 0.40 (aluminium oxide, methylene chloride/methanol=20:1)

Mass spectrum (ESI⁺): m/z=590 [M+H]⁺

(139) 1-{2-[1-(tert.-butyloxycarbonyl)-1H-indol-4-yl]-2-oxo-ethyl}-3-methyl-7-(2-butyn-1-yl)-8-[3-(tert.-butyloxycarbonylamino)-piperidin-1-yl]-xanthine
$R_f$ value: 0.55 (silica gel, petroleum ether/ethyl acetate=1:2)
Mass spectrum (ESI$^+$): m/z=674 [M+H]$^+$ (140) 1-[(1-methyl-2-oxo-1,2-dihydro-quinolin-6-yl)methyl]-3-methyl-7-(2-butyn-1-yl)-8-[3-(tert.-butyloxycarbonylamino)-piperidin-1-yl]-xanthine
Mass spectrum (EI): m/z=587 [M]$^+$ (141) 1-({1-[(2-trimethylsilanyl-ethoxy)methyl]-2-oxo-1,2-dihydro-quinolin-6-yl}methyl)-3-methyl-7-(2-butyn-1-yl)-8-[3-(tert.-butyloxycarbonylamino)-piperidin-1-yl]-xanthine
Mass spectrum (ESI$^+$): m/z=704 [M+H]$^+$ (142) 1-[(2,3,8-trimethyl-quinoxalin-6-yl)methyl]-3-methyl-7-(2-butyn-1-yl)-8-[3-(tert.-butyloxycarbonylamino)-piperidin-1-yl]-xanthine
Mass spectrum (ESI$^+$): m/z=601 [M+H]$^+$ (143) 1-[(8-methyl-quinoxalin-6-yl)methyl]-3-methyl-7-(2-butyn-1-yl)-8-[3-(tert.-butyloxycarbonylamino)-piperidin-1-yl]-xanthine
Mass spectrum (ESI$^+$): m/z=573 [M+H]$^+$ (144) 1-[(4-methyl-phthalazin-1-yl)methyl]-3-methyl-7-(2-butyn-1-yl)-8-[3-(tert.-butyloxycarbonylamino)-piperidin-1-yl]-xanthine
$R_f$ value: 0.65 (silica gel, methylene chloride/methanol=9:1)
Mass spectrum (ESI$^+$): m/z=573 [M+H]$^+$ (145) 1-[(4-bromo-3-methoxy-isoquinolin-1-yl)methyl]-3-methyl-7-(2-butyn-1-yl)-8-[3-(tert.-butyloxycarbonylamino)-piperidin-1-yl]-xanthine
$R_f$ value: 0.65 (silica gel, methylene chloride/ethyl acetate=1:1)
Mass spectrum (ESI$^+$): m/z=666, 668 [M+H]$^+$ (146) 1-[(4-difluoromethoxy-naphthalen-1-yl)methyl]-3-methyl-7-(2-butyn-1-yl)-8-[(R)-3-(tert.-butyloxycarbonylamino)-piperidin-1-yl]-xanthine
$R_f$ value: 0.80 (silica gel, methylene chloride/methanol/conc. aqueous ammonia=90:10:1)
Mass spectrum (ESI$^+$): m/z=623 [M+H]$^+$ (147) 1-{2-[1-(tert.-butyloxycarbonyl)-1H-indol-7-yl]-2-oxo-ethyl}-3-methyl-7-(2-butyn-1-yl)-8-bromo-xanthine
$R_f$ value: 0.83 (silica gel, methylene chloride/methanol=95:5)

(148) 1-[(E)-3-(2-nitro-phenyl)-2-propen-1-yl]-3-methyl-7-(2-butyn-1-yl)-8-[3-(tert.-butyloxycarbonylamino)-piperidin-1-yl]-xanthine
Mass spectrum (ESI$^+$): m/z=578 [M+H]$^+$ (149) 1-((E)-3-pentafluorophenyl-2-propen-1-yl)-3-methyl-7-(2-butyn-1-yl)-8-[3-(tert.-butyloxycarbonylamino)-piperidin-1-yl]-xanthine
Mass spectrum (ESI$^+$): m/z=623 [M+H]$^+$ (150) 1-[(4-nitro-naphthalen-1-yl)methyl]-3-methyl-7-(2-butyn-1-yl)-8-[(R)-3-(tert.-butyloxycarbonylamino)-piperidin-1-yl]-xanthine
$R_f$ value: 0.41 (silica gel, methylene chloride/methanol=95:5)
Mass spectrum (ESI$^+$): m/z=602 [M+H]$^+$ (151) 1-[(benzooxazol-2-y)methyl]-3-methyl-7-(2-butyn-1-yl)-8-[3-(tert.-butyloxycarbo-nylamino)-piperidin-1-yl]-xanthine
$R_f$ value: 0.40 (silica gel, cyclohexane/ethyl acetate=3:7)
Mass spectrum (ESI$^+$): m/z=548 [M+H]$^+$ (152) 1-[(5-nitro-benzooxazol-2-y)methyl]-3-methyl-7-(2-butyn-1-yl)-8-[3-(tert.-butyloxycarbonylamino)-piperidin-1-yl]-xanthine
$R_f$ value: 0.50 (silica gel, cyclohexane/ethyl acetate/methanol=5:4:1)
Mass spectrum (ESI$^+$): m/z=593 [M+H]$^+$ (153) 1-[(3-methyl-isoquinolin-1-yl)methyl]-3-methyl-7-(3-methyl-1-buten-1-yl)-8-bromo-xanthine
$R_f$ value: 0.65 (silica gel, methylene chloride/methanol=95:5)
Mass spectrum (ESI$^+$): m/z=468, 470 [M+H]$^+$ (154) 1-[(quinolin-7-yl)methyl]-3-methyl-7-(2-butyn-1-yl)-8-[3-(tert.-butyloxycarbonyl-amino)-piperidin-1-yl]-xanthine
Mass spectrum (ESI$^+$): m/z=558 [M+H]$^+$ (155) 1-[([1,5]naphthyridin-2-yl)methyl]-3-methyl-7-(2-butyn-1-yl)-8-[3-(tert.-butyloxycarbonylamino)-piperidin-1-yl]-xanthine
Mass spectrum (ESI$^+$): m/z=559 [M+H]$^+$ (156) 1-[(8-methyl-quinoxalin-6-yl)methyl]-3-methyl-7-(2-butyn-1-yl)-8-[(R)-3-(tert.-butyloxycarbonylamino)-piperidin-1-yl]-xanthine
$R_f$ value: 0.45 (silica gel, methylene chloride/methanol=19:1)
Mass spectrum (ESI$^+$): m/z=573 [M+H]$^+$ (157) 1-[(2,3,8-trimethyl-quinoxalin-6-yl)methyl]-3-methyl-7-(2-butyn-1-yl)-8-[(R)-3-(tert.-butyloxycarbonylamino)-piperidin-1-yl]xanthine
$R_f$ value: 0.32 (silica gel, methylene chloride/methanol=96:4)
Mass spectrum (ESI$^+$): m/z=601 [M+H]$^+$ (158) 1-[([1,6]naphthyridin-5-yl)methyl]-3-methyl-7-(2-butyn-1-yl)-8-[3-(tert.-butyloxycarbonylamino)-piperidin-1-yl]-xanthine
$R_f$ value: 0.20 (silica gel, ethyl acetate/methanol=98:2)
Mass spectrum (ESI$^+$): m/z=559 [M+H]$^+$ (159) 1-[([1,8]naphthyridin-2-yl)methyl]-3-methyl-7-(2-butyn-1-yl)-8-[3-(tert.-butyloxycarbonylamino)-piperidin-1-yl]-xanthine
$R_f$ value: 0.12 (silica gel, ethyl acetate/methanol=98:2)
Mass spectrum (ESI$^+$): m/z=559 [M+H]$^+$ (160) 1-[(4-fluoro-naphthalen-1-yl)methyl]-3-methyl-7-(2-butyn-1-yl)-8-[(R)-3-(tert.-butyloxycarbonylamino)-piperidin-1-yl]-xanthine
$R_f$ value: 0.47 (silica gel, petroleum ether/ethyl acetate=1:1)
Mass spectrum (ESI$^+$): m/z=575 [M+H]$^+$ (161) 1-[([1,5]naphthyridin-2-yl)methyl]-3-methyl-7-(2-butyn-1-yl)-8-[(R)-3-(tert.-butyloxycarbonylamino)-piperidin-1-yl]-xanthine
$R_f$ value: 0.39 (silica gel, ethyl acetate)
Mass spectrum (ESI$^+$): m/z=559 [M+H]$^+$ (162) 1-[2-(3-methyl-2-oxo-2,3-dihydro-benzooxazol-4-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.60 (silica gel, methylene chloride/methanol=95:5)
Mass spectrum (ESI$^+$): m/z=606 [M+H]$^+$ (163) 1-[(8-phenyl-quinoxalin-6-yl)methyl]-3-methyl-7-(2-butyn-1-yl)-8-[(R)-3-(tert.-butyloxycarbonylamino)-piperidin-1-yl]-xanthine
$R_f$ value: 0.48 (silica gel, methylene chloride/methanol=95:5)
Mass spectrum (ESI$^+$): m/z=356 [M+H]$^+$ (164) 1-[([1,5]naphthyridin-4-yl)methyl]-3-methyl-7-(2-butyn-1-yl)-8-[(R)-3-(tert.-butyloxycarbonylamino)-piperidin-1-yl]-xanthine
$R_f$ value: 0.25 (silica gel, ethyl acetate/petroleum ether=4:1)
Mass spectrum (ESI$^+$): m/z=559 [M+H]$^+$ (165) 1-((E)-3-pentafluorophenyl-allyl)-3-methyl-7-(2-butyn-1-yl)-8-[(R)-3-(tert.-butyloxycarbonylamino)-piperidin-1-yl]-xanthine
Mass spectrum (ESI$^+$): m/z=623 [M+H]$^+$
(166) 1-[(E)-3-(2-trifluoromethyl-phenyl)-allyl]-3-methyl-7-(2-butyn-1-yl)-8-[(R)-3-(tert.-butyloxycarbonylamino)-piperidin-1-yl]-xanthine
Mass spectrum (ESI$^+$): m/z=601 [M+H]$^+$
(167) 1-[(E)-3-(3-trifluoromethyl-phenyl)-allyl]-3-methyl-7-(2-butyn-1-yl)-8-[(R)-3-(tert.-butyloxycarbonylamino)-piperidin-1-yl]-xanthine
Mass spectrum (ESI$^+$): m/z=601 [M+H]$^+$
(168) 1-[(E)-3-(4-trifluoromethyl-phenyl)-allyl]-3-methyl-7-(2-butyn-1-yl)-8-[(R)-3-(tert.-butyloxycarbonylamino)-piperidin-1-yl]-xanthine
Mass spectrum (ESI$^+$): m/z=601 [M+H]$^+$
(169) 1-[(3-trifluoromethyl-isoquinolin-1-yl)methyl]-3-methyl-7-(2-butyn-1-yl)-8-[(R)-3-(tert.-butyloxycarbonylamino)-piperidin-1-yl]-xanthine
$R_f$ value: 0.68 (silica gel, cyclohexane/ethyl acetate=3:7)
Mass spectrum (ESI$^+$): m/z=626 [M+H]$^+$
(170) 1-[(3-methyl-isoquinolin-1-yl)methyl]-3-methyl-7-(2-cyano-benzyl)-8-chloro-xanthine
(171) 1-[(3-difluoromethyl-isoquinolin-1-yl)methyl]-3-methyl-7-(2-butyn-1-yl)-8-[(R)-3-(tert.-butyloxycarbonylamino)-piperidin-1-yl]-xanthine
$R_f$ value: 0.38 (silica gel, cyclohexane/ethyl acetate=1:1)
Mass spectrum (ESI$^+$): m/z=608 [M+H]$^+$
(172) 1-[(4-chloro-3-methoxy-isoquinolin-1-yl)methyl]-3-methyl-7-(2-butyn-1-yl)-8-[3-(tert.-butyloxycarbonylamino)-piperidin-1-yl]-xanthine
$R_f$ value: 0.65 (silica gel, methylene chloride/ethyl acetate=1:1)
Mass spectrum (ESI$^+$): m/z=622, 624 [M+H]$^+$
(173) 1-[(4-ethoxy-quinazolin-2-yl)methyl]-3-methyl-7-(2-butyn-1-yl)-8-[3-(tert.-butyloxycarbonylamino)-piperidin-1-yl]-xanthine
$R_f$ value: 0.25 (silica gel, methylene chloride/ethyl acetate=1:1)
Mass spectrum (ESI$^+$): m/z=603 [M+H]$^+$
(174) 1-[(4-isopropyloxy-quinazolin-2-yl)methyl]-3-methyl-7-(2-butyn-1-yl)-8-[3-(tert.-butyloxycarbonylamino)-piperidin-1-yl]-xanthine
$R_f$ value: 0.40 (silica gel, methylene chloride/ethyl acetate=1:1)
Mass spectrum (ESI$^+$): m/z=617 [M+H]$^+$
(175) 1-[(2-methyl-benzothiazol-6-yl)methyl]-3-methyl-7-(2-butyn-1-yl)-8-[3-(tert.-butyloxycarbonylamino)-piperidin-1-yl]-xanthine
$R_f$ value: 0.56 (silica gel, methylene chloride/ethyl acetate=1:1)
Mass spectrum (ESI$^+$): m/z=578 [M+H]$^+$
(176) 1-[(3-phenyl-isoquinolin-1-yl)methyl]-3-methyl-7-(2-butyn-1-yl)-8-[(R)-3-(tert.-butyloxycarbonylamino)-piperidin-1-yl]-xanthine
$R_f$ value: 0.75 (silica gel, methylene chloride/ethyl acetate=1:1)
Mass spectrum (ESI$^+$): m/z=634 [M+H]$^+$
(177) 1-[(4-phenyloxy-quinazolin-2-yl)methyl]-3-methyl-7-(2-butyn-1-yl)-8-[3-(tert.-butyloxycarbonylamino)-piperidin-1-yl]-xanthine
$R_f$ value: 0.35 (silica gel, methylene chloride/ethyl acetate=1:1)
Mass spectrum (ESI$^+$): m/z=651 [M+H]$^+$
(178) 1-[(4-phenyl-quinazolin-2-yl)methyl]-3-cyclopropyl-7-(2-butyn-1-yl)-8-[3-(tert.-butyloxycarbonylamino)-piperidin-1-yl]-xanthine
$R_f$ value: 0.45 (silica gel, methylene chloride/ethyl acetate=1:1)
Mass spectrum (ESI$^+$): m/z=661 [M+H]$^+$
(179) 1-[(3-methyl-isoquinolin-1-yl)methyl]-3-cyclopropyl-7-(2-butyn-1-yl)-8-[3-(tert.-butyloxycarbonylamino)-piperidin-1-yl]-xanthine
$R_f$ value: 0.50 (silica gel, methylene chloride/ethyl acetate=1:1)
Mass spectrum (ESI$^+$): m/z=598 [M+H]$^+$
(180) 1-[2-(3-difluoromethoxy-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.77 (silica gel, methylene chloride/ethyl acetate=1:1)
Mass spectrum (ESI$^+$): m/z=601 [M+H]$^+$
(181) 1-[(2-phenyl-quinazolin-4-yl)methyl]-3-methyl-7-(2-butyn-1-yl)-8-[3-(tert.-butyloxycarbonylamino)-piperidin-1-yl]-xanthine
$R_f$ value: 0.65 (silica gel, methylene chloride/ethyl acetate=1:1)
Mass spectrum (ESI$^+$): m/z=635 [M+H]$^+$
(182) 1-[2-(2-methoxy-phenyl)-2-oxo-ethyl]-3-methyl-7-(2-butyn-1-yl)-8-[3-(tert.-butyloxycarbonylamino)-piperidin-1-yl]-xanthine
$R_f$ value: 0.57 (silica gel, methylene chloride/ethyl acetate=1:1)
Mass spectrum (ESI$^+$): m/z=565 [M+H]$^+$
(183) 1-[2-(3-methoxy-phenyl)-2-oxo-ethyl]-3-methyl-7-(2-butyn-1-yl)-8-[3-(tert.-butyloxycarbonylamino)-piperidin-1-yl]-xanthine
$R_f$ value: 0.63 (silica gel, methylene chloride/ethyl acetate=1:1)
Mass spectrum (ESI$^+$): m/z=565 [M+H]$^+$
(184) 1-[2-(3-trifluoromethoxy-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.64 (silica gel, methylene chloride/ethyl acetate=1:1)
Mass spectrum (ESI$^+$): m/z=619 [M+H]$^+$
(185) 1-[2-(biphenyl-2-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.70 (silica gel, methylene chloride/ethyl acetate=1:1)
Mass spectrum (ESI$^+$): m/z=611 [M+H]$^+$
(186) 1-[2-(biphenyl-3-yl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.75 (silica gel, methylene chloride/ethyl acetate=1:1)
Mass spectrum (ESI$^+$): m/z=611 [M+H]$^+$
(187) 1-[2-(3-isopropyloxy-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.66 (silica gel, methylene chloride/ethyl acetate=1:1)
Mass spectrum (ESI$^+$): m/z=593 [M+H]$^+$
(188) 1-[(3-methyl-isoquinolin-1-yl)methyl]-3-cyclopropyl-7-(2-butyn-1-yl)-8-[(R)-3-(tert.-butyloxycarbonylamino)-piperidin-1-yl]-xanthine
$R_f$ value: 0.50 (silica gel, methylene chloride/ethyl acetate=1:1)
Mass spectrum (ESI$^+$): m/z=598 [M+H]$^+$
(189) 1-[(4-phenyl-quinazolin-2-yl)methyl]-3-cyclopropyl-7-(2-butyn-1-yl)-8-[(R)-3-(tert.-butyloxycarbonylamino)-piperidin-1-yl]-xanthine R$_f$ value: 0.50 (silica gel, methylene chloride/ethyl acetate=1:1)
Mass spectrum (ESI$^+$): m/z=661 [M+H]$^+$ (190) 1-[(4-cyano-naphthalen-1-yl)methyl]-3-cyclopropyl-7-(2-butyn-1-yl)-8-[(R)-3-(tert.-butyloxycarbonylamino)-piperidin-1-yl]-xanthine
R$_f$ value: 0.75 (silica gel, methylene chloride/ethyl acetate=1:1)
Mass spectrum (ESI$^+$): m/z=608 [M+H]$^+$ (191) 1-[2-(2-phenyloxy-phenyl)-2-oxo-ethyl]-3-methyl-7-(2-butyn-1-yl)-8-[(R)-3-(tert.-butyloxycarbonylamino)-piperidin-1-yl]-xanthine
R$_f$ value: 0.85 (silica gel, methylene chloride/ethyl acetate=1:1)
Mass spectrum (ESI$^+$): m/z=627 [M+H]$^+$ (192) 1-[2-(3-ethoxy-phenyl)-2-oxo-ethyl]-3-methyl-7-(2-butyn-1-yl)-8-[(R)-3-(tert.-butyloxycarbonylamino)-piperidin-1-yl]-xanthine
R$_f$ value: 0.72 (silica gel, methylene chloride/ethyl acetate=1:1)
Mass spectrum (ESI$^+$): m/z=579 [M+H]$^+$ (193) 1-[2-(3-methoxy-phenyl)-2-oxo-ethyl]-3-methyl-7-(2-butyn-1-yl)-8-[(R)-3-(tert.-butyloxycarbonylamino)-piperidin-1-yl]-xanthine
R$_f$ value: 0.67 (silica gel, methylene chloride/ethyl acetate=1:1)
Mass spectrum (ESI$^+$): m/z=565 [M+H]$^+$ (194) 1-[2-(2-methoxy-phenyl)-2-oxo-ethyl]-3-methyl-7-(2-butyn-1-yl)-8-[(R)-3-(tert.-butyloxycarbonylamino)-piperidin-1-yl)-xanthine
R$_f$ value: 0.57 (silica gel, methylene chloride/ethyl acetate=1:1)
Mass spectrum (ESI$^+$): m/z=565 [M+H]$^+$ (195) 1-[(3-methyl-isoquinolin-1-yl)methyl]-3-methyl-7-(2-chloro-benzyl)-8-bromo-xanthine (196) 1-[(3-methyl-isoquinolin-1-yl)methyl]-3-methyl-7-(2-bromo-benzyl)-8-[(R)-3-(tert.-butyloxycarbonylamino)-piperidin-1-yl]-xanthine (197) 1-[(1,2,3,4-tetrahydro-phenanthridin-6-yl)methyl]-3-methyl-7-(2-butyn-1-yl)-8-[3-(tert.-butyloxycarbonylamino)-piperidin-1-yl]-xanthine
R$_f$ value: 0.55 (silica gel, ethyl acetate/petroleum ether=2:1)
Mass spectrum (ESI$^+$): m/z=612 [M+H]$^+$ Example VI 1-(2-{3-[(methanesulphinyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine To a solution of 402 mg of 1-(2-{3-[(methylsulphanyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine in 10 ml hexafluoroisopropanol are added 0.15 ml of a 35% hydrogen peroxide solution. The reaction mixture is stirred for half an hour at ambient temperature. Then 5 ml of a 10% sodium thiosulphate solution are added. The aqueous phase is extracted twice with 5 ml of methylene chloride. The combined extracts are dried over sodium sulphate and evaporated down. The yellow residue is purified by chromatography through a silica gel column with cyclohexane/ethyl acetate/methanol (5:4:1) as eluant.

Yield: 299 mg (73% of theory)
R$_f$ value: 0.28 (silica gel, cyclohexane/ethyl acetate/methanol=5:4:1)
Mass spectrum (ESI$^+$): m/z=643 [M+H]$^+$ The following compounds are obtained analogously to Example VI:

(1) 1-[2-(3-methanesulphinyl-phenyl)-2-oxo-ethyl]-3-methyl-7-(3-methyl-2-buten-1-yl)-8-[3-(tert.-butyloxycarbonylamino)-piperidin-1-yl]-xanthine
R$_f$ value: 0.05 (silica gel, ethyl acetate/cyclohexane=3:1)
Mass spectrum (ESI$^+$): m/z=613 [M+H]$^+$ (2) 1-(2-{2-[(methanesulphinyl)methoxy]-phenyl}-2-oxo-ethyl)-3-methyl-7-(2-butyn-1-yl)-8-[3-(tert.-butyloxycarbonylamino)-piperidin-1-yl]-xanthine
Mass spectrum (ESI$^+$): m/z=627 [M+H]$^+$ Example VII 3-[(2-trimethylsilanyl-ethoxy)methyl]-7-(3-methyl-2-buten-1-yl)-8-[3-(tert.-butyloxycarbonylamino)-piperidin-1-yl]-xanthine 236 µl of 1,8-diazabicyclo[5.4.0]undec-7-ene are added dropwise to 630 mg of 7-(3-methyl-2-buten-1-yl)-8-[3-(tert.-butyloxycarbonylamino)-piperidin-1-yl]-xanthine in 11 ml of acetonitrile. The solution is stirred for two hours at ambient temperature, then the acetonitrile is distilled off in vacuo. The flask residue is taken up in 11 ml of N,N-dimethylformamide and combined with 258 mg of (2-trimethylsilanyl-ethoxy)methyl chloride. The reaction mixture is stirred for three hours at 120° C. For working up water is added, the precipitate formed is filtered off and taken up in ethyl acetate. The solution is dried over magnesium sulphate, evaporated down and chromatographed through a silica gel column with cyclohexane/ethyl acetate/methanol (6:1:0 to 0:5:1) as eluant.

Yield: 435 mg (53% of theory)
Mass spectrum (ESI$^+$): m/z=549 [M+H]$^+$

The following compounds are obtained analogously to Example VII:

(1) 3-[(2-trimethylsilanyl-ethoxy)methyl]-7-(2-cyano-benzyl)-xanthine
Mass spectrum (ESI$^-$): m/z=396 [M–H]$^-$ (2) 3-[(methoxycarbonyl)methyl]-7-(3-methyl-2-buten-1-yl)-8-[3-(tert.-butyloxy-carbonylamino)-piperidin-1-yl]-xanthine
R$_f$ value: 0.31 (silica gel, methylene chloride/methanol/conc. aqueous ammonia=90:10:1)
Mass spectrum (ESI$^+$): m/z=491 [M+H]$^+$ Example VIII 7-(3-methyl-2-buten-1-yl)-8-[3-(tert.-butyloxycarbonylamino)-piperidin-1-yl]-xanthine 510 mg of potassium-tert.butoxide are added to 2.32 g of 2-[3-(tert.-butyloxycarbonylamino)-piperidin-1-yl]-3-(3-methyl-2-buten-1-yl)-4-ethoxycarbonyl-5-{[(ethoxycarbonylamino)carbonyl]amino}-3H-imidazole in 35 ml of ethanol. The yellow solution is refluxed for five hours. After cooling to ambient temperature it is diluted with methylene chloride. The organic phase is washed with saturated ammonium chloride solution and saturated sodium chloride solution, dried over magnesium sulphate and evaporated down. The crude product is purified by chromatography through a silica gel column with methylene chloride/methanol/conc. methanolic ammonia (95:5:1 to 90:10:1) as eluant.

Yield: 630 mg (35% of theory)
$R_f$ value: 0.24 (silica gel, methylene chloride/methanol/conc. aqueous ammonia=90:10:1)
Mass spectrum (ESI$^+$): m/z=419 [M+H]$^+$

Example IX

2-[3-(tert.-butyloxycarbonylamino)-piperidin-1-yl]-3-(3-methyl-2-buten-1-yl)-4-ethoxycarbonyl-5-{[(ethoxycarbonylamino)carbonyl]amino}-3H-imidazole 2.97 ml of ethyl isocanatoformate are added to 4.00 g of 2-[3-(tert.-butyloxycarbonylamino)-piperidin-1-yl]-3-(3-methyl-2-buten-1-yl)-4-ethoxycarbonyl-5-amino-3H-imidazole in 90 ml of 1,2-dimethoxyethane and the light brown solution is heated overnight at 120° C. in an oil bath. Then a further 0.6 ml of ethyl isocyanatoformate is added and heating is continued for a further four hours. For working up the reaction mixture is combined with saturated potassium carbonate solution and extracted with ethyl acetate. The organic phase is dried over magnesium sulphate, evaporated down and purified through a silica gel column with methylene chloride/methanol/conc. methanolic ammonia (98:2:1 to 90:10:1) as eluant.
Yield: 2.27 g (45% of theory)
$R_f$ value: 0.29 (silica gel, methylene chloride/methanol/conc. aqueous ammonia=90:10:1)
Mass spectrum (ESI$^+$): m/z=537 [M+H]$^+$

Example X

2-[3-(tert.-butyloxycarbonylamino)-piperidin-1-yl]-3-(3-methyl-2-buten-1-yl)-4-ethoxycarbonyl-5-amino-3H-imidazole Prepared by refluxing cyanimino-[N-(3-methyl-2-buten-1-yl)-N-(ethoxy-carbonylmethyl)-amino]-[3-(tert.-butyloxycarbonylamino)-piperidin-1-yl]-methane with sodium in ethanol.
$R_f$ value: 0.26 (aluminium oxide, ethyl acetate/petroleum ether=8:2)
Mass spectrum (ESI$^+$): m/z=422 [M+H]$^+$

Example XI

Cyanimino-[N-(3-methyl-2-buten-1-yl)-N-(ethoxycarbonylmethyl)-amino]-[3-(tert.-butyloxycarbonylamino)-piperidin-1-yl]-methane Prepared by reacting cyanimino-[N-(3-methyl-2-buten-1-yl)-N-(ethoxy-carbonylmethyl)-amino]-phenyloxy-methane with 3-(tert.-butyloxycarbonylamino)-piperidine in the presence of potassium carbonate in N,N-dimethylformamide at ambient temperature.
$R_f$ value: 0.10 (silica gel, petroleum ether/ethyl acetate=6:4)
Mass spectrum (ESI$^+$): m/z=422 [M+H]$^+$

Example XII cyanimino-[N-(3-methyl-2-buten-1-yl)-N-(ethoxycarbonylmethyl)-amino]-phenyloxy-methane Prepared by reacting cyanimino-[(ethoxycarbonylmethyl)amino]-phenyloxy-methane with 1-bromo-3-methyl-2-butene in the presence of potassium carbonate in acetone at ambient temperature.

$R_f$ value: 0.70 (silica gel, cyclohexane/ethyl acetate=1:1)
Mass spectrum (ESI$^+$): m/z=316 [M+H]$^+$

Example XIII cyanimino-[(ethoxycarbonylmethyl)amino]-phenyloxy-methan

Prepared by reacting diphenylcyanocarbonimidate with ethyl aminoacetate-hydrochloride in the presence of triethylamine in isopropanol at ambient temperature (analogously to R. Besse et al., *Tetrahedron* 1990, 46, 7803-7812).
$R_f$ value: 0.73 (silica gel, petroleum ether/ethyl acetate=8:2)
Mass spectrum (ESI$^+$): m/z=248 [M+H]$^+$

Example XIV 1-methyl-3-[(methoxycarbonyl)methyl]-7-(2-cyanobenzyl)-8-chloro-xanthine Prepared by reacting 1-methyl-7-(2-cyano-benzyl)-8-chloro-xanthine with methyl bromoacetate in the presence of potassium carbonate in N,N-dimethylformamide at ambient temperature.
$R_f$ value: 0.80 (silica gel, methylene chloride/methanol=9:1)
Mass spectrum (ESI$^+$): m/z=388, 390 [M+H]$^+$
The following compounds are obtained analogously to Example XIV:
(1) 1-methyl-3-cyanomethyl-7-(2-cyano-benzyl)-8-chloro-xanthine
Mass spectrum (ESI$^+$): m/z=355, 357 [M+H]$^+$
(2) 1-methyl-3-(2-propyn-1-yl)-7-(2-cyano-benzyl)-8-chloro-xanthine
$R_f$ value: 0.80 (silica gel, methylene chloride/methanol=95:5)
Mass spectrum (ESI$^+$): m/z=354, 356 [M+H]$^+$
(3) 1-methyl-3-(2-propen-1-yl)-7-(2-cyano-benzyl)-8-chloro-xanthine
$R_f$ value: 0.90 (silica gel, methylene chloride/methanol=95:5)
Mass spectrum (ESI$^+$): m/z=356, 358 [M+H]$^+$
(4) 1-(2-phenyl-2-oxo-ethyl)-3-cyanomethyl-7-(3-methyl-2-buten-1-yl)-8-[3-(tert.-butyloxycarbonylamino)-piperidin-1-yl]-xanthine
$R_f$ value: 0.78 (silica gel, methylene chloride/methanol/conc. aqueous ammonia=90:10:1)
Mass spectrum (ESI$^+$): m/z=576 [M+H]$^+$
(5) 1-methyl-3-isopropyl-7-(2-cyano-benzyl)-8-chloro-xanthine
Mass spectrum (ESI$^+$): m/z=358, 360 [M+H]$^+$

Example XV 1-methyl-7-(2-cyano-benzyl)-8-chloro-xanthine

Prepared by treating 1-methyl-3-[(2-trimethylsilanylethoxy)methyl]-7-(2-cyano-benzyl)-8-chloro-xanthine with trifluoroacetic acid in methylene chloride at ambient temperature.
$R_f$ value: 0.50 (silica gel, methylene chloride/methanol=9:1)
Mass spectrum (ESI$^+$): m/z=316, 318 [M+H]$^+$
The following compounds are obtained analogously to Example XV:
(1) 1-(2-phenyl-2-oxo-ethyl)-3-methyl-8-bromo-xanthine R$_f$ value: 0.26 (silica gel, methylene chloride/methanol=95:5)
Mass spectrum (ESI$^-$): m/z=361, 363 [M–H]$^-$
(2) 1-[(4-oxo-3,4-dihydro-phthalazin-1-yl)methyl]-3-methyl-7-(3-methyl-2-buten-1-yl)-8-(3-amino-piperidin-1-yl)-xanthine
(As the compound still contains impurities which cannot be removed by chromatography, the material is again converted into the BOC-protected derivative and then purified by chromatography, cf. Ex. XXV (1).)
Mass spectrum (ESI$^+$): m/z=491 [M+H]$^+$ Example XVI 1-methyl-3-[(2-trimethylsilanyl-ethoxy)methyl]-7-(2-cyano-benzyl)-8-chloro-xanthine Prepared by chlorination of 1-methyl-3-[(2-trimethylsilanyl-ethoxy)methyl]-7-(2-cyano-benzyl)-xanthine with N-chlorosuccinimide in dichloroethane while refluxing.
Mass spectrum (EI): m/z=445, 447 [M]$^+$ Example XVII 7-(2-cyano-benzyl)-xanthine Prepared by treating 16.68 g of 2-amino-7-(2-cyano-benzyl)-1,7-dihydro-purin-6-one with 17.00 g of sodium nitrite in a mixture of 375 ml of conc. acetic acid, 84 ml of water and 5.2 ml of conc. hydrochloric acid at 50° C.
Yield: 8.46 g (50% of theory)
Mass spectrum (ESI$^+$): m/z=268 [M+H]$^+$ Example XVIII 2-amino-7-(2-cyano-benzyl)-1,7-dihydro-purin-6-one Prepared by reacting 20.00 g of guanosine-hydrate with 22.54 g of 2-cyano-benzylbromide in dimethylsulphoxide at 60° C. and subsequent treatment with 57 ml of conc. hydrochloric acid.
Yield: 18.00 g (97% of theory)
Mass spectrum (ESI$^+$): m/z=267 [M+H]$^+$ Example XIX 1-{2-[3-(2-oxo-imidazolidin-1-yl)-phenyl]-2-oxo-ethyl}-3-methyl-7-(3-methyl-2-buten-1-yl)-8-[3-(tert.-butyloxycarbonylamino)-piperidin-1-yl]-xanthine Prepared by treating 1-[2-(3-{[(2-chloro-ethylamino)carbonyl]amino}-phenyl)-2-oxo-ethyl]-3-methyl-7-(3-methyl-2-buten-1-yl)-8-[3-(tert.-butyloxy-carbonylamino)-piperidin-1-yl]-xanthine with potassium-tert.butoxide in N,N-dimethylformamide at ambient temperature.
R$_f$ value: 0.50 (silica gel, methylene chloride/methanol=9:1)

Example XX

1-[2-(3-{[(2-chloro-ethylamino)carbonyl]amino}-phenyl)-2-oxo-ethyl]-3-methyl-7-(3-methyl-2-buten-1-yl)-8-[3-(tert.-butyloxycarbonylamino)-piperidin-1-yl]-xanthine Prepared by reacting 221 mg of 1-[2-(3-amino-phenyl)-2-oxo-ethyl]-3-methyl-7-(3-methyl-2-buten-1-yl)-8-[3-(tert.-butyloxycarbonylamino)-piperidin-1-yl]-xanthine with 60 μl of 2-chloroethyl isocyanate in 3 ml methylene chloride at ambient temperature.
Yield: 163 mg (64% of theory)
R$_f$ value: 0.20 (silica gel, cyclohexane/ethyl acetate/methanol=6:3:1)
Mass spectrum (ESI$^+$): m/z=671, 673 [M+H]$^+$
The following compounds are obtained analogously to Example XX:
(1) 1-[2-(2-{[(ethoxycarbonylamino)carbonyl]amino}-phenyl)-2-oxo-ethyl]-3-methyl-7-(3-methyl-2-buten-1-yl)-8-[3-(tert.-butyloxycarbonylamino)-piperidin-1-yl]-xanthine
(Carried out in N,N-dimethylformamide at 30° C.)
R$_f$ value: 0.26 (silica gel, cyclohexane/ethyl acetate=4:6)
Mass spectrum (ESI$^+$): m/z=681 [M+H]$^+$ Example XXI 1-[2-(3-amino-phenyl)-2-oxo-ethyl]-3-methyl-7-(3-methyl-2-buten-1-yl)-8-[3-(tert.-butyloxycarbonylamino)-piperidin-1-yl]-xanthine Prepared by treating 1-[2-(3-nitro-phenyl)-2-oxo-ethyl]-3-methyl-7-(3-methyl-2-buten-1-yl)-8-[3-(tert.-butyloxycarbonylamino)-piperidin-1-yl]-xanthine with iron powder in a mixture of ethanol, water and glacial acetic acid (80:25:10) at 100° C.
R$_f$ value: 0.55 (silica gel, cyclohexane/ethyl acetate/methanol/conc. aqueous ammonia=50:30:20:1)
Mass spectrum (ESI$^+$): m/z=566 [M+H]$^+$
The following compounds are obtained analogously to Example XXI:
(1) 1-[2-(2-amino-phenyl)-2-oxo-ethyl]-3-methyl-7-(3-methyl-2-buten-1-yl)-8-[3-(tert.-butyloxycarbonylamino)-piperidin-1-yl]-xanthine
Mass spectrum (ESI$^+$): m/z=566 [M+H]$^+$
(2) 1-[2-(2-amino-phenyl)-2-oxo-ethyl]-3-methyl-7-(3-methyl-2-buten-1-yl)-8-[(S)-3-(tert.-butyloxycarbonylamino)-piperidin-1-yl]-xanthine
Mass spectrum (ESI$^+$): m/z=566 [M+H]$^+$
(3) 1-[(5-amino-isoquinolin-1-yl)methyl]-3-methyl-7-(3-methyl-2-buten-1-yl)-8-[3-(tert.-butyloxycarbonylamino)-piperidin-1-yl]-xanthine
R$_f$ value: 0.22 (silica gel, ethyl acetate)
Mass spectrum (ESI$^+$): m/z=589 [M+H]$^+$
(4) 1-[2-(2-amino-phenyl)-2-oxo-ethyl]-3-methyl-7-[(1-cyclopenten-1-yl)methyl]-8-bromo-xanthine
Mass spectrum (ESI$^+$): m/z=458, 460 [M+H]$^+$
(5) 1-[2-(2-amino-phenyl)-2-oxo-ethyl]-3-methyl-7-((E)-2-buten-1-yl)-8-bromo-xanthine
(product contains approx. 10% of Z isomer)
R$_f$ value: 0.55 (silica gel, cyclohexane/ethyl acetate=4:6)
Mass spectrum (ESI$^+$): m/z=432, 434 [M+H]$^+$
(6) 1-[2-(2-amino-phenyl)-2-oxo-ethyl]-3-methyl-7-(2-butyn-1-yl)-8-bromo-xanthine
R$_f$ value: 0.50 (silica gel, methylene chloride/methanol=95:5)
Mass spectrum (ESI$^+$): m/z=430, 432 [M+H]$^+$
(7) 1-[2-(2-amino-phenyl)-2-oxo-ethyl]-3-methyl-7-((E)-2-buten-1-yl)-8-[(R)-3-(tert.-butyloxycarbonylamino)-piperidin-1-yl]-xanthine
Mass spectrum (ESI$^+$): m/z=552 [M+H]$^+$
(8) 1-[2-(2-amino-phenyl)-2-oxo-ethyl]-3-methyl-7-((E)-2-buten-1-yl)-8-[(S)-3-(tert.-butyloxycarbonylamino)-piperidin-1-yl]-xanthine
Mass spectrum (ESI$^+$): m/z=552 [M+H]$^+$ (9) 1-[2-(2-amino-3-methoxy-phenyl)-2-oxo-ethyl]-3-methyl-7-(3-methyl-2-buten-1-yl)-8-[3-(tert.-butyloxycarbonylamino)-piperidin-1-yl]-xanthine
$R_f$ value: 0.82 (silica gel, ethyl acetate/petroleum ether=4:1)
Mass spectrum (ESI$^+$): m/z=596 [M+H]$^+$ Example XXII 1-(2-{2-[(ethylcarbonyl)amino]-phenyl}-2-oxo-ethyl)-3-methyl-7-(3-methyl-2-buten-1-yl)-8-[3-(tert.-butyloxycarbonylamino)-piperidin-1-yl]-xanthine Prepared by reacting 248 mg of 1-[2-(2-amino-phenyl)-2-oxo-ethyl]-3-methyl-7-(3-methyl-2-buten-1-yl)-8-[3-(tert.-butyloxycarbonylamino)-piperidin-1-yl]-xanthine with 40 µl of propionic acid chloride in the presence of 60 µl of pyridine in N,N-dimethylformamide at 80° C.
Yield: 168 mg (62% of theory)
$R_f$ value: 0.55 (silica gel, cyclohexane/ethyl acetate=3:7)
Mass spectrum (ESI$^+$): m/z=622 [M+H]$^+$ The following compounds are obtained analogously to Example XXII:
(1) 1-({5-[methoxycarbonyl)methylamino]-isoquinolin-1-yl}methyl)-3-methyl-7-(3-methyl-2-buten-1-yl)-8-[3-(tert.-butyloxycarbonylamino)-piperidin-1-yl]-xanthine
(Carried out with methyl bromoacetate and potassium carbonate)
$R_f$ value: 0.42 (silica gel, methylene chloride/methanol=95:5)
Mass spectrum (ESI$^+$): m/z=661 [M+H]$^+$
(2) 1-[2-(2-acetylamino-phenyl)-2-oxo-ethyl]-3-methyl-7-((E)-2-buten-1-yl)-8-[3-(tert.-butyloxycarbonylamino)-piperidin-1-yl]-xanthine
(product contains approx. 10% of Z isomer)
Mass spectrum (ESI$^+$): m/z=594 [M+H]$^+$
(3) 1-(2-{2-[(isopropylcarbonyl)amino]-phenyl}-2-oxo-ethyl)-3-methyl-7-((E)-2-buten-1-yl)-8-[3-(tert.-butyloxycarbonylamino)-piperidin-1-yl]-xanthine
(product contains approx. 10% of Z isomer)
Mass spectrum (ESI$^+$): m/z=622 [M+H]$^+$
(4) 1-[2-(2-acetylamino-phenyl)-2-oxo-ethyl]-3-methyl-7-(3-methyl-2-buten-1-yl)-8-[(S)-3-(tert.-butyloxycarbonylamino)-piperidin-1-yl]-xanthine
$R_f$ value: 0.50 (silica gel, cyclohexane/ethyl acetate=3:7)
Mass spectrum (ESI$^+$): m/z=608 [M+H]$^+$
(5) 1-[2-(2-acetylamino-phenyl)-2-oxo-ethyl]-3-methyl-7-(2-butyn-1-yl)-8-[3-(tert.-butyloxycarbonylamino)-piperidin-1-yl]-xanthine
$R_f$ value: 0.34 (silica gel, cyclohexane/ethyl acetate=3:7)
Mass spectrum (ESI$^+$): m/z=592 [M+H]$^+$
(6) 1-(2-{2-[(isopropylcarbonyl)amino]-phenyl}-2-oxo-ethyl)-3-methyl-7-(3-methyl-2-buten-1-yl)-8-[3-(tert.-butyloxycarbonylamino)-piperidin-1-yl]-xanthine
$R_f$ value: 0.25 (silica gel, cyclohexane/ethyl acetate=1:1)
Mass spectrum (ESI$^+$): m/z=636 [M+H]$^+$
(7) 1-(2-{2-[(isopropylcarbonyl)amino]-phenyl}-2-oxo-ethyl)-3-methyl-7-(2-butyn-1-yl)-8-[3-(tert.-butyloxycarbonylamino)-piperidin-1-yl]-xanthine
$R_f$ value: 0.44 (silica gel, methylene chloride/methanol=95:5)
Mass spectrum (ESI$^+$): m/z=620 [M+H]$^+$
(8) 1-[2-(2-acetylamino-phenyl)-2-oxo-ethyl]-3-methyl-7-(2-butyn-1-yl)-8-[(S)-3-(tert.-butyloxycarbonylamino)-piperidin-1-yl]-xanthine
$R_f$ value: 0.34 (silica gel, cyclohexane/ethyl acetate=3:7)
Mass spectrum (ESI$^+$): m/z=592 [M+H]$^+$
(9) 1-(2-{2-[(isopropylcarbonyl)amino]-phenyl}-2-oxo-ethyl)-3-methyl-7-(2-butyn-1-yl)-8-[(S)-3-(tert.-butyloxycarbonylamino)-piperidin-1-yl]-xanthine
$R_f$ value: 0.44 (silica gel, methylene chloride/methanol=95:5)
Mass spectrum (ESI$^+$): m/z=620 [M+H]$^+$
(10) 1-(2-{2-[(methoxycarbonyl)amino]-phenyl}-2-oxo-ethyl)-3-methyl-7-(3-methyl-2-buten-1-yl)-8-[3-(tert.-butyloxycarbonylamino)-piperidin-1-yl]-xanthine
(Carried out in acetonitrile at 55° C.)
$R_f$ value: 0.25 (silica gel, cyclohexane/ethyl acetate=1:1)
Mass spectrum (ESI$^+$): m/z=624 [M+H]$^+$
(11) 1-(2-{2-[(isopropylcarbonyl)amino]-phenyl}-2-oxo-ethyl)-3-methyl-7-((E)-2-buten-1-yl)-8-[(S)-3-(tert.-butyloxycarbonylamino)-piperidin-1-yl]-xanthine
(Carried out in acetonitrile at 65° C.)
$R_f$ value: 0.50 (silica gel, cyclohexane/ethyl acetate/isopropanol=14:3:3)
Mass spectrum (ESI$^+$): m/z=622 [M+H]$^+$
(12) 1-(2-{2-[(ethylcarbonyl)amino]-phenyl}-2-oxo-ethyl)-3-methyl-7-((E)-2-buten-1-yl)-8-[(R)-3-(tert.-butyloxycarbonylamino)-piperidin-1-yl]-xanthine
Mass spectrum (ESI$^+$): m/z=608 [M+H]$^+$
(13) 1-[2-(2-acetylamino-phenyl)-2-oxo-ethyl]-3-methyl-7-((E)-2-buten-1-yl)-8-[(R)-3-(tert.-butyloxycarbonylamino)-piperidin-1-yl]-xanthine
Mass spectrum (ESI$^+$): m/z=594 [M+H]$^+$
(14) 1-[2-(2-acetylamino-phenyl)-2-oxo-ethyl]-3-methyl-7-((E)-2-buten-1-yl)-8-[(S)-3-(tert.-butyloxycarbonylamino)-piperidin-1-yl]-xanthine
$R_f$ value: 0.28 (silica gel, cyclohexane/ethyl acetate/isopropanol=8:1:1)
Mass spectrum (ESI$^+$): m/z=594 [M+H]$^+$
(15) 1-(2-{2-[(isopropylcarbonyl)amino]-phenyl}-2-oxo-ethyl)-3-methyl-7-(2-butyn-1-yl)-8-[(R)-3-(tert.-butyloxycarbonylamino)-piperidin-1-yl]-xanthine
$R_f$ value: 0.90 (silica gel, methylene chloride/methanol=9:1)
(16) 1-(2-{2-[(isopropylcarbonyl)amino]-phenyl}-2-oxo-ethyl)-3-methyl-7-((E)-2-buten-1-yl)-8-[(R)-3-(tert.-butyloxycarbonylamino)-piperidin-1-yl]-xanthine
(Carried out in 1,2-dichloroethane at 45° C.)
$R_f$ value: 0.30 (silica gel, cyclohexane/ethyl acetate/isopropanol=8:1:1)
Mass spectrum (ESI$^+$): m/z=622 [M+H]$^+$
(17) 1-(2-{2-[(ethylcarbonyl)amino]-phenyl}-2-oxo-ethyl)-3-methyl-7-((E)-2-buten-1-yl)-8-[(S)-3-(tert.-butyloxycarbonylamino)-piperidin-1-yl]-xanthine
$R_f$ value: 0.48 (silica gel, cyclohexane/ethyl acetate/isopropanol=14:3:3)
Mass spectrum (ESI$^+$): m/z=608 [M+H]$^+$
(18) 1-(2-{2-[(ethylcarbonyl)amino]-phenyl}-2-oxo-ethyl)-3-methyl-7-(2-butyn-1-yl)-8-[(R)-3-(tert.-butyloxycarbonylamino)-piperidin-1-yl]-xanthine
Mass spectrum (ESI$^+$): m/z=606 [M+H]$^+$
(19) 1-(2-{2-[(ethylcarbonyl)amino]-phenyl}-2-oxo-ethyl)-3-methyl-7-(2-butyn-1-yl)-8-[(S)-3-(tert.-butyloxycarbonylamino)-piperidin-1-yl]-xanthine
$R_f$ value: 0.22 (silica gel, methylene chloride/methanol=95:5)
(20) 1-(2-{2-[(phenylcarbonyl)amino]-phenyl}-2-oxo-ethyl)-3-methyl-7-((E)-2-buten-1-yl)-8-[3-(tert.-butyloxycarbonylamino)-piperidin-1-yl]-xanthine
$R_f$ value: 0.55 (silica gel, cyclohexane/ethyl acetate/isopropanol=14:3:3)
Mass spectrum (ESI$^+$): m/z=656 [M+H]$^+$

(21) 1-(2-{2-[(cyclopropylcarbonyl)amino]-phenyl}-2-oxo-ethyl)-3-methyl-7-[(1-cyclopenten-1-yl)methyl]-8-[3-(tert.-butyloxycarbonylamino)-piperidin-1-yl]-xanthine
(Carried out with Hünig base and 4-dimethylamino-pyridine in methylene chloride)
$R_f$ value: 0.60 (silica gel, methylene chloride/methanol=18:1)

Example XXIII 1-(2-{3-[(methoxycarbonyl)methoxy]-phenyl}-2-oxo-ethyl)-3-methyl-7-(3-methyl-2-buten-1-yl)-8-(3-amino-piperidin-1-yl)-xanthine Prepared by treating 1-(2-{3-[(methoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine with trifluoroacetic acid in methylene chloride at ambient temperature.
Mass spectrum (ESI$^+$): m/z=539 [M+H]$^+$
The following compounds are obtained analogously to Example XXIII:
(1) 1-(2-{2-[(methoxycarbonyl)methoxy]-phenyl}-2-oxo-ethyl)-3-methyl-7-(3-methyl-2-buten-1-yl)-8-(3-amino-piperidin-1-yl)-xanthine
Mass spectrum (ESI$^+$): m/z=539 [M+H]$^+$

Example XXIV 1-methyl-3-phenyl-7-(2-cyano-benzyl)-8-chloro-xanthine

A mixture of 829 mg of 1-methyl-7-(2-cyano-benzyl)-8-chloro-xanthine, 640 mg of phenylboric acid, 509 mg of anhydrous copper acetate and 0.43 ml of pyridine in 20 ml methylene chloride is stirred for four days at ambient temperature in the presence of 100 mg of 4 Å molecular sieves. Then another 320 mg of phenylboric acid are added and the reaction mixture is stirred for another day at ambient temperature. For working up the mixture is filtered through talc and washed with ethyl acetate. The filtrate is evaporated down and chromatographed through a silica gel column with cyclohexane/ethyl acetate (7:3 to 1:1) as eluant.
Yield: 142 mg (14% of theory)
Mass spectrum (ESI$^+$): m/z=392, 394 [M+H]$^+$

Example XXV 1-(2-phenyl-2-oxo-ethyl)-7-(3-methyl-2-buten-1-yl)-8-[3-(tert.-butyloxycarbonyl-amino)-piperidin-1-yl]-xanthine Prepared by reacting 1-(2-phenyl-2-oxo-ethyl)-7-(3-methyl-2-buten-1-yl)-8-(3-amino-piperidin-1-yl)-xanthine with di-tert.butyl pyrocarbonate in the presence of Hünig base in methylene chloride at ambient temperature.
$R_f$ value: 0.27 (silica gel, methylene chloride/methanol/conc. aqueous ammonia=90:10:1)
The following compounds are obtained analogously to Example XXV:
(1) 1-[(4-oxo-3,4-dihydro-phthalazin-1-yl)methyl]-3-methyl-7-(3-methyl-2-buten-1-yl)-8-[3-(tert.-butyloxycarbonyl-amino)-piperidin-1-yl]-xanthine
$R_f$ value: 0.27 (silica gel, methylene chloride/methanol=95:5)
Mass spectrum (ESI$^+$): m/z=591 [M+H]$^+$
(2) 7-acetyl-1-(tert.-butyloxycarbonyl)-1H-indole
$R_f$ value: 0.82 (silica gel, methylene chloride/petroleum ether/ethyl acetate=5:4:1)
Mass spectrum (ESI$^+$): m/z=260 [M+H]$^+$

Example XXVI

1-[(cinnolin-4-yl)methyl]-3-methyl-7-(3-methyl-2-buten-1-yl)-8-chloro-xanthine and 1-[(1,4-dihydro-cinnolin-4-yl)methyl]-3-methyl-7-(3-methyl-2-buten-1-yl)-8-chloro-xanthine 510 mg of a mixture of (cinnolin-4-yl)-methanol and (1,4-dihydro-cinnolin-4-yl)-methanol (see Ex. XXVII) are added to 830 mg of 3-methyl-7-(3-methyl-2-buten-1-yl)-8-chloro-xanthine and 1.25 g of triphenylphosphine in 25 ml of tetrahydrofuran. The reaction mixture is combined with 0.92 ml diethyl azodicarboxylate and stirred overnight at ambient temperature. Then it is evaporated down and chromatographed through a silica gel column with ethyl acetate/petroleum ether (7:3 to 0:1) as eluant. A mixture of cinnoline and 1,4-dihydro-cinnoline compound is obtained.
Yield: 660 mg (52% of theory)
$R_f$ value: 0.60 (silica gel, ethyl acetate/petroleum ether=7:3)
The following compounds are obtained analogously to Example XXVI:
(1) 1-({4-oxo-3-[(2-trimethylsilanyl-ethoxy)methyl]-3,4-dihydro-phthalazin-1-yl}methyl)-3-methyl-7-(3-methyl-2-buten-1-yl)-8-chloro-xanthine
$R_f$ value: 0.85 (silica gel, methylene chloride/methanol=95:5)
Mass spectrum (ESI$^+$): m/z=557, 559 [M+H]$^+$
(2) 1-[(isoquinolin-3-yl)methyl]-3-methyl-7-(3-methyl-2-buten-1-yl)-8-chloro-xanthine
Melting point: 194-195° C.
Mass spectrum (ESI$^+$): m/z=410, 412 [M+H]$^+$
(3) 1-[(3-methyl-4-oxo-3,4-dihydro-phthalazin-1-yl)methyl]-3-methyl-7-(3-methyl-2-buten-1-yl)-8-chloro-xanthine
$R_f$ value: 0.66 (silica gel, ethyl acetate)
Mass spectrum (ESI$^+$): m/z=441, 443 [M+H]$^+$
(4) 1-[(quinolin-4-yl)methyl]-3-methyl-7-(2-butyn-1-yl)-8-bromo-xanthine
(Carried out with potassium carbonate)
$R_f$ value: 0.45 (silica gel, ethyl acetate)
Mass spectrum (ESI$^+$): m/z=438, 440 [M+H]$^+$
(5) 1-[(isoquinolin-1-yl)methyl]-3-methyl-7-(2-butyn-1-yl)-8-bromo-xanthine
$R_f$ value: 0.78 (silica gel, ethyl acetate)
Mass spectrum (ESI$^+$): m/z=438, 440 [M+H]$^+$
(6) 1-[(4-dimethylamino-naphthalen-1-yl)methyl]-3-methyl-7-(2-butyn-1-yl)-8-[3-(tert.-butyloxycarbonylamino)-piperidin-1-yl]-xanthine
$R_f$ value: 0.80 (silica gel, ethyl acetate)
Mass spectrum (ESI$^+$): m/z=600 [M+H]$^+$
(7) 1-[(isoquinolin-1-yl)methyl]-3-methyl-7-((E)-2-buten-1-yl)-8-bromo-xanthine (The product contains approx. 20% of Z isomer)
$R_f$ value: 0.71 (silica gel, ethyl acetate)
Mass spectrum (ESI$^+$): m/z=440, 442 [M+H]$^+$
(8) 1-[(1-methyl-1H-indol-2-yl)methyl]-3-methyl-7-(2-butyn-1-yl)-8-bromo-xanthine
$R_f$ value: 0.95 (silica gel, methylene chloride/methanol=95:5)
Mass spectrum (ESI$^+$): m/z=440, 442 [M+H]$^+$ (9) 1-[(quinolin-3-yl)methyl]-3-methyl-7-(2-butyn-1-yl)-8-bromo-xanthine
$R_f$ value: 0.55 (silica gel, ethyl acetate/petroleum ether=8:2)
Mass spectrum (ESI$^+$): m/z=438, 440 [M+H]$^+$
(10) 1-{[1-(tert.-butyloxycarbonylamino)-1H-indol-2-yl]methyl}-3-methyl-7-(2-butyn-1-yl)-8-bromo-xanthine
$R_f$ value: 0.74 (silica gel, petroleum ether/ethyl acetate=1:1)
Mass spectrum (ESI$^+$): m/z=526, 528 [M+H]$^+$
(11) 1-({2-methyl-1-[(2-trimethylsilanyl-ethoxy)methyl]-1H-benzoimidazol-5-yl}methyl)-3-methyl-7-(2-butyn-1-yl)-8-bromo-xanthine (mixed with 1-({2-methyl-3-[(2-trimethylsilanyl-ethoxy)methyl]-3H-benzoimidazol-5-yl}methyl)-3-methyl-7-(2-butyn-1-yl)-8-bromo-xanthine)
Mass spectrum (ESI$^+$): m/z=571, 573 [M+H]$^+$
(12) 1-[(1-[(2-trimethylsilanyl-ethoxy)methyl]-1H-benzoimidazol-5-yl)methyl]-3-methyl-7-(2-butyn-1-yl)-8-bromo-xanthine (mixed with 1-[(3-[(2-trimethylsilanyl-ethoxy)methyl]-3H-benzoimidazol-5-yl)methyl]-3-methyl-7-(2-butyn-1-yl)-8-bromo-xanthine)
$R_f$ value: 0.50 (silica gel, methylene chloride/methanol=95:5)
Mass spectrum (ESI$^+$): m/z=557, 559 [M+H]$^+$
(13) 1-[(pyrazolo[1,5-a]pyridin-2-yl)methyl]-3-methyl-7-(2-butyn-1-yl)-8-bromo-xanthine
$R_f$ value: 0.35 (silica gel, petroleum ether/ethyl acetate=1:2)
Mass spectrum (ESI$^+$): m/z=427, 429 [M+H]$^+$ Example XXVII (cinnolin-4-yl)-methanol and (1,4-dihydro-cinnolin-4-yl)-methanol A solution of 1.00 g of methyl cinnolin-4-carboxylate in 15 ml diethyl ether is added dropwise at 0° C. to a suspension of 222 mg of lithium aluminium hydride in 5 ml of diethyl ether. After 1.5 hours water is carefully added dropwise to the reaction mixture, this is stirred with methylene chloride and suction filtered through a glass fibre filter. The aqueous phase is extracted with methylene chloride and the combined organic phases are dried over magnesium sulphate and evaporated down. According to $^1$H-NMR a mixture of cinnoline and 1,4-dihydro-cinnoline compound is obtained as a yellow oil which is reacted further without any more purification.
Yield: 530 mg (62% of theory)
$R_f$ value: 0.63 (silica gel, ethyl acetate)
Mass spectrum (ESI$^+$): m/z=161 [M1+H]$^+$ and 163 [M2+H]$^+$
The following compounds are obtained analogously to Example XXVII:
(1) {2-methyl-1-[(2-trimethylsilanyl-ethoxy)methyl]-1H-benzoimidazol-5-yl}-methanol
(mixed with {2-methyl-3-[(2-trimethylsilanyl-ethoxy)methyl]-3H-benzoimidazol-5-yl}-methanol)
Mass spectrum (ESI$^+$): m/z=293 [M+H]$^+$
(2) (2,3,8-trimethyl-quinoxalin-6-yl)-methanol
$R_f$ value: 0.45 (silica gel, petroleum ether/ethyl acetate=1:2)
Mass spectrum (ESI$^+$): m/z=203 [M+H]$^+$
(3) (8-methyl-quinoxalin-6-yl)-methanol
$R_f$ value: 0.18 (silica gel, cyclohexane/ethyl acetate=1:1)
Mass spectrum (ESI$^+$): m/z=175 [M+H]$^+$
(4) (E)-3-pentafluorophenyl-2-propen-1-ol
(Carried out with diisobutylaluminium hydride in toluene)
Mass spectrum (EI): m/z=224 [M]$^+$
(5) (E)-3-(2-trifluoromethyl-phenyl)-2-propen-1-ol
(Carried out with diisobutylaluminium hydride in toluene)
(6) (E)-3-(3-trifluoromethyl-phenyl)-2-propen-1-ol
(Carried out with diisobutylaluminium hydride in toluene)
Mass spectrum (EI): m/z=202 [M]$^+$
(7) (E)-3-(4-trifluoromethyl-phenyl)-2-propen-1-ol
(Carried out with diisobutylaluminium hydride in toluene)

Example XXVIII 4-hydroxymethyl-2-[(2-trimethylsilanyl-ethoxy)methyl]-2H-phthalazin-1-one Prepared by treating methyl 4-oxo-3-[(2-trimethylsilanyl-ethoxy)methyl]-3,4-dihydro-phthalazin-1-carboxylate with sodium borohydride in tetrahydrofuran at 40° C.
$R_f$ value: 0.55 (silica gel, cyclohexane/ethyl acetate 1:1)
Mass spectrum (ESI$^+$): m/z=307 [M+H]$^+$
The following compounds are obtained analogously to Example XXVIII:
(1) (3,4-dimethyl-isoquinolin-1-yl)-methanol
(Carried out with lithium borohydride in tetrahydrofuran)
$R_f$ value: 0.35 (silica gel, petroleum ether/ethyl acetate=2:1)
Mass spectrum (ESI$^+$): m/z=188 [M+H]$^+$
(2) (3-methyl-imidazo[1,2-a]pyridin-2-yl)-methanol
(Carried out with lithium borohydride in tetrahydrofuran)
$R_f$ value: 0.48 (silica gel, methylene chloride/methanol/conc. aqueous ammonia=90:10:1)
Mass spectrum (ESI$^+$): m/z=163 [M+H]$^+$
(3) (3,4-dimethyl-6,7-dihydro-5H-[2]pyrindin-1-yl)-methanol
(Carried out with lithium borohydride in tetrahydrofuran)
$R_f$ value: 0.40 (aluminium oxide, petroleum ether/ethyl acetate=1:1)
Mass spectrum (ESI$^+$): m/z=178 [M+H]$^+$
(4) (3,4-dimethyl-5,6,7,8-tetrahydro-isoquinolin-1-yl)-methanol
(Carried out with lithium borohydride in tetrahydrofuran)
$R_f$ value: 0.45 (aluminium oxide, petroleum ether/ethyl acetate=3:1)
Mass spectrum (ESI$^+$): m/z=192 [M+H]$^+$
(5) 6-hydroxymethyl-1,2,3,4-tetrahydro-phenanthridine
(Carried out with lithium borohydride in tetrahydrofuran at ambient temperature)
$R_f$ value: 0.40 (silica gel, petroleum ether/ethyl acetate=2:1)
Mass spectrum (ESI$^+$): m/z=214 [M+H]$^+$ Example XXIX Methyl 4-oxo-3-[(2-trimethylsilanyl-ethoxy)methyl]-3,4-dihydro-phthalazin-1-carboxylate Prepared by reacting methyl 4-oxo-3,4-dihydro-phthalazin-1-carboxylate with (2-trimethylsilanyl-ethoxy)methylchloride in the presence of Hünig base in methylene chloride at ambient temperature.
$R_f$ value: 0.75 (silica gel, cyclohexane/ethyl acetate 6:4)
Mass spectrum (ESI$^+$): m/z=335 [M+H]$^+$ The following compounds are obtained analogously to Example XXIX:

(1) 7-acetyl-3-[(2-trimethylsilanyl-ethoxy)methyl]-3H-benzooxazol-2-one

Mass spectrum (ESI⁺): m/z=308 [M+H]⁺

(2) 4-acetyl-3-[(2-trimethylsilanyl-ethoxy)methyl]-3H-benzooxazol-2-one $R_f$ value: 0.87 (silica gel, methylene chloride/methanol=99:1)

(3) 4-acetyl-1,3-bis-[(2-trimethylsilanyl-ethoxy)methyl]-1,3-dihydro-benzoimidazol-2-one (Carried out with potassium-tert.butoxide in N,N-dimethylformamide)

$R_f$ value: 0.90 (silica gel, petroleum ether/ethyl acetate=1:1)

Mass spectrum (ESI⁺): m/z=437 [M+H]⁺

(4) 6-methyl-1-[(2-trimethylsilanyl-ethoxy)methyl]-1H-quinolin-2-one $R_f$ value: 0.78 (silica gel, petroleum ether/ethyl acetate=1:1)

Mass spectrum (ESI⁺): m/z=290 [M+H]⁺

(5) methyl {2-methyl-1-[(2-trimethylsilanyl-ethoxy)methyl]-1H-benzoimidazol-5-yl}-carboxylate (mixed with methyl {2-methyl-3-[(2-trimethylsilanyl-ethoxy)methyl]-3H-benzoimidazol-5-yl}-carboxylate)

Mass spectrum (ESI⁺): m/z=321 [M+H]⁺

Example XXX

1-[2-(3-methanesulphonyl-phenyl)-2-oxo-ethyl]-3-methyl-7-(3-methyl-2-buten-1-yl)-8-[3-(tert.-butyloxycarbonylamino)-piperidin-1-yl]-xanthine 0.22 ml of a 35% hydrogen peroxide solution and 20 mg of sodium tungstate are added to 500 mg of 1-[2-(3-methylsulphanyl-phenyl)-2-oxo-ethyl]-3-methyl-7-(3-methyl-2-buten-1-yl)-8-[3-(tert.-butyloxycarbonylamino)-piperidin-1-yl]-xanthine in 5 ml methylene chloride. The reaction mixture is stirred overnight at ambient temperature, then 1 ml of methanol is added. After another 48 hours a further 1.5 ml of 35% hydrogen peroxide solution, a spatula tip of sodium tungstate and two drops of water are added. The next morning, the oxidation is complete according to thin layer chromatography and the reaction mixture is diluted with 50 ml methylene chloride and washed twice with 30 ml of 10% sodium thiosulphate solution. The organic phase is dried over magnesium sulphate and evaporated down, leaving a viscous resin which is reacted further without any more purification.

Yield: 530 mg (100% of theory)

$R_f$ value: 0.72 (silica gel, ethyl acetate)

Mass spectrum (ESI⁺): m/z=629 [M+H]⁺

Example XXXI

1-[2-(3-carboxy-phenyl)-2-oxo-ethyl]-3-methyl-7-(3-methyl-2-buten-1-yl)-8-[3-(tert.-butyloxycarbonylamino)-piperidin-1-yl]-xanthine Prepared by treating 1-[2-(3-methoxycarbonyl-phenyl)-2-oxo-ethyl]-3-methyl-7-(3-methyl-2-buten-1-yl)-8-[3-(tert.-butyloxycarbonylamino)-piperidin-1-yl]-xanthine with 3 M sodium hydroxide solution in methanol at ambient temperature.

$R_f$ value: 0.34 (silica gel, methylene chloride/methanol=9:1)

Mass spectrum (ESI⁺): m/z=595 [M+H]⁺

The following compounds are obtained analogously to Example XXXI:

(1) 1-[2-(2-carboxy-phenyl)-2-oxo-ethyl]-3-methyl-7-(3-methyl-2-buten-1-yl)-8-[3-(tert.-butyloxycarbonylamino)-piperidin-1-yl]-xanthine $R_f$ value: 0.49 (silica gel, methylene chloride/methanol=9:1)

(2) 1-[2-(2-carboxymethoxy-phenyl)-2-oxo-ethyl]-3-methyl-7-(2-butyn-1-yl)-8-[3-(tert.-butyloxycarbonylamino)-piperidin-1-yl]-xanthine (Carried out with 4 M potassium hydroxide solution in tetrahydrofuran)

Mass spectrum (ESI⁺): m/z=609 [M+H]⁺

(3) 1-[2-(2-carboxymethylamino-phenyl)-2-oxo-ethyl]-3-methyl-7-((E)-2-buten-1-yl)-8-[(R)-3-(tert.-butyloxycarbonylamino)-piperidin-1-yl]-xanthine (Carried out with 4 M potassium hydroxide solution in tetrahydrofuran)

$R_f$ value: 0.65 (silica gel, cyclohexane/ethyl acetate=3:7)

Mass spectrum (ESI⁺): m/z=610 [M+H]⁺

(4) 1-carboxymethyl-3-methyl-7-(2-butyn-1-yl)-8-[3-(tert.-butyloxycarbonylamino)-piperidin-1-yl]-xanthine Mass spectrum (ESI⁺): m/z=475 [M+H]⁺

Example XXXII

1-{2-[3-(methylaminocarbonyl)-phenyl]-2-oxo-ethyl}-3-methyl-7-(3-methyl-2-buten-1-yl)-8-[3-(tert.-butyloxycarbonylamino)-piperidin-1-yl]-xanthine A mixture of 190 mg of 1-[2-(3-carboxy-phenyl)-2-oxo-ethyl]-3-methyl-7-(3-methyl-2-buten-1-yl)-8-[3-(tert.-butyloxycarbonylamino)-piperidin-1-yl]-xanthine, 43 µl of a 40% aqueous methylamine solution, 103 mg of O-(benzotriazol-1-yl)-N,N,N',N'-tetramethyluronium tetrafluoroborate, 43 mg of N-hydroxybenzotriazole and 45 µl of triethylamine in 3 ml of tetrahydrofuran is stirred for eight hours at ambient temperature. For working up the reaction mixture is diluted with ethyl acetate and washed with water, 10% citric acid solution, 10% potassium carbonate solution and saturated sodium chloride solution. The organic phase is evaporated down and chromatographed through a silica gel column with methylene chloride/methanol (98:2 to 80:20) as eluant.

Yield: 173 mg (89% of theory)

$R_f$ value: 0.30 (silica gel, methylene chloride/methanol=20:1)

Mass spectrum (ESI⁺): m/z=608 [M+H]⁺

The following compounds are obtained analogously to Example XXXII:

(1) 1-{2-[3-(dimethylaminocarbonyl)-phenyl]-2-oxo-ethyl}-3-methyl-7-(3-methyl-2-buten-1-yl)-8-[3-(tert.-butyloxycarbonylamino)-piperidin-1-yl]-xanthine $R_f$ value: 0.28 (silica gel, methylene chloride/methanol=20:1)

Mass spectrum (ESI⁺): m/z=622 [M+H]⁺

(2) 1-{2-[3-(morpholin-4-yl-carbonyl)-phenyl]-2-oxo-ethyl}-3-methyl-7-(3-methyl-2-buten-1-yl)-8-[3-(tert.-butyloxycarbonylamino)-piperidin-1-yl]-xanthine $R_f$ value: 0.30 (silica gel, methylene chloride/methanol=20:1)

Mass spectrum (ESI⁺): m/z=664 [M+H]⁺

(3) 1-{2-[2-(dimethylaminocarbonyl)-phenyl]-2-oxo-ethyl}-3-methyl-7-(3-methyl-2-buten-1-yl)-8-[3-(tert.-butyloxycarbonylamino)-piperidin-1-yl]-xanthine R$_f$ value: 0.30 (silica gel, methylene chloride/methanol=20:1)
Mass spectrum (ESI$^+$): m/z=622 [M+H]$^+$
(4) 1-{2-[2-(morpholin-4-yl-carbonyl)-phenyl]-2-oxo-ethyl}-3-methyl-7-(3-methyl-2-buten-1-yl)-8-[3-(tert.-butyloxycarbonylamino)-piperidin-1-yl]-xanthine
R$_f$ value: 0.30 (silica gel, methylene chloride/methanol=20:1)
Mass spectrum (ESI$^+$): m/z=664 [M+H]$^+$
(5) 1-(2-{2-[(isopropylaminocarbonyl)methoxy]-phenyl}-2-oxo-ethyl)-3-methyl-7-(2-butyn-1-yl)-8-[3-(tert.-butyloxycarbonyl amino)-piperidin-1-yl]-xanthine
(Carried out with Hünig base in N,N-dimethylformamide)
Mass spectrum (ESI$^+$): m/z=650 [M+H]$^+$
(6) 1-(2-{2-[(ethylaminocarbonyl)methoxy]-phenyl}-2-oxo-ethyl)-3-methyl-7-(2-butyn-1-yl)-8-[3-(tert.-butyloxycarbonylamino)-piperidin-1-yl]-xanthine
(Carried out with Hünig base in N,N-dimethylformamide)
Mass spectrum (ESI$^+$): m/z=636 [M+H]$^+$
(7) 1-(2-{2-[2-oxo-2-(pyrrolidin-1-yl)-ethoxy]-phenyl}-2-oxo-ethyl)-3-methyl-7-(2-butyn-1-yl)-8-[3-(tert.-butyloxycarbonylamino)-piperidin-1-yl]-xanthine
(Carried out with Hünig base in N,N-dimethylformamide)
Mass spectrum (ESI$^+$): m/z=662 [M+H]$^+$
(8) 1-(2-{2-[2-(morpholin-4-yl)-2-oxo-ethoxy]-phenyl}-2-oxo-ethyl)-3-methyl-7-(2-butyn-1-yl)-8-[3-(tert.-butyloxycarbonylamino)-piperidin-1-yl]-xanthine
(Carried out with Hünig base in N,N-dimethylformamide)
Mass spectrum (ESI$^+$): m/z=678 [M+H]$^+$
(9) 1-(2-{2-[(methylaminocarbonyl)methylamino]-phenyl}-2-oxo-ethyl)-3-methyl-7-((E)-2-buten-1-yl)-8-[(R)-3-(tert.-butyloxycarbonylamino)-piperidin-1-yl]-xanthine
R$_f$ value: 0.40 (silica gel, cyclohexane/ethyl acetate/methanol=5:4:1)
Mass spectrum (ESI$^+$): m/z=623 [M+H]$^+$
(10) 1-[(2-amino-phenylaminocarbonyl)methyl]-3-methyl-7-(2-butyn-1-yl)-8-[3-(tert.-butyloxycarbonylamino)-piperidin-1-yl]-xanthine
R$_f$ value: 0.40 (silica gel, cyclohexane/ethyl acetate/methanol=5:4:1)
Mass spectrum (ESI$^+$): m/z=565 [M+H]$^+$ Example XXXIII 1-chloromethyl-4-methyl-isoquinoline-hydrochloride Prepared by treating (4-methyl-isoquinolin-1-yl)-methanol with thionyl chloride in methylene chloride.
R$_f$ value: 0.76 (silica gel, methylene chloride/methanol/conc. aqueous ammonia=95:5:0.1)
Mass spectrum (ESI$^+$): m/z=192, 194 [M+H]$^+$
The following compounds are obtained analogously to Example XXXIII:
(1) 1-chloromethyl-3,4-dimethyl-isoquinoline-hydrochloride
R$_f$ value: 0.65 (silica gel, petroleum ether/ethyl acetate=2:1)
Mass spectrum (ESI$^+$): m/z=206, 208 [M+H]$^+$
(2) 5-chloromethyl-8-methoxy-quinoline-hydrochloride
Mass spectrum (ESI$^+$): m/z=208, 210 [M+H]$^+$
(3) 8-chloromethyl-5-methoxy-quinoline-hydrochloride
Mass spectrum (EI): m/z=207, 209 [M]$^+$
(4) 2-chloromethyl-3-methyl-imidazo[1,2-a]pyridine-hydrochloride
R$_f$ value: 0.55 (silica gel, methylene chloride/methanol/conc. aqueous ammonia=90:10:1)
Mass spectrum (ESI$^+$): m/z=181, 183 [M+H]$^+$
(5) 8-chloromethyl-5-methoxy-isoquinoline-hydrochloride
Mass spectrum (ESI$^+$): m/z=208, 210 [M+H]$^+$
(6) 1-chloromethyl-3,4-dimethyl-6,7-dihydro-5H-[2]pyridine-hydrochloride
R$_f$ value: 0.50 (aluminium oxide, petroleum ether/ethyl acetate=10:1)
Mass spectrum (ESI$^+$): m/z=196, 198 [M+H]$^+$
(7) 1-chloromethyl-3,4-dimethyl-5,6,7,8-tetrahydro-isoquinoline-hydrochloride
R$_f$ value: 0.50 (aluminium oxide, petroleum ether/ethyl acetate=10:1)
Mass spectrum (ESI$^+$): m/z=210, 212 [M+H]$^+$
(8) 6-chloromethyl-2,3,8-trimethyl-quinoxaline-hydrochloride
Mass spectrum (ESI$^+$): m/z=221, 223 [M+H]$^+$
(9) 6-chloromethyl-8-methyl-quinoxaline-hydrochloride
Mass spectrum (ESI$^+$): m/z=193,195 [M+H]$^+$
(10) 6-chloromethyl-1,2,3,4-tetrahydro-phenanthridine-hydrochloride
R$_f$ value: 0.50 (silica gel, petroleum ether/ethyl acetate=5:1)
Mass spectrum (ESI$^+$): m/z=232, 234 [M+H]$^+$ Example XXXIV 1-[(4-oxo-3,4-dihydro-quinazolin-2-yl)methyl]-3-methyl-7-(2-butyn-1-yl)-8-[3-(tert.-butyloxycarbonylamino)-piperidin-1-yl]-xanthine 0.5 ml of a 1 M sodium methoxide solution in methanol is added dropwise to a solution of 428 mg of 1-cyanomethyl-3-methyl-7-(2-butyn-1-yl)-8-[3-(tert.-butyloxycarbonylamino)-piperidin-1-yl]-xanthine in 3 ml of methanol at ambient temperature. After about 20 minutes the thick suspension formed is heated gently in a water bath and diluted with 2 ml of methanol. As soon as the reaction to form the iminoester is complete according to thin layer chromatography, the reaction mixture is neutralised with 0.5 ml 1 M glacial acetic acid solution in methanol and combined with a solution of 130 mg of anthranilic acid in 2 ml of methanol. Gentle heating produces a clear solution, which is stirred for 2.5 hours at ambient temperature. Then the reaction mixture is gently refluxed for about 3.5 hours. After standing overnight at ambient temperature the methanol is distilled off and the residue is stirred with cold water, suction filtered and dried. The crude product is suspended in 5 ml of methanol, gently heated and after cooling suction filtered, washed with methanol and dried in the desiccator.
Yield: 302 mg (56% of theory)
R$_f$ value: 0.55 (silica gel, ethyl acetate)
Mass spectrum (ESI$^+$): m/z=575 [M+H]$^+$
The following compounds are obtained analogously to Example XXXV:
(1) (4-difluoromethoxy-naphthalen-1-yl)-methanol
R$_f$ value: 0.33 (silica gel, cyclohexane/ethyl acetate=6:4)
Mass spectrum (ESI$^-$): m/z=223 [M–H]$^-$ Example XXXV (4-dimethylamino-naphthalen-1-yl)-methanol prepared by reduction of 4-dimethylamino-naphthalene-1-carbaldehyde with sodium borohydride in aqueous tetrahydrofuran.
R$_f$ value: 0.67 (silica gel, cyclohexane/ethyl acetate=1:1)

Example XXXVI 2-bromo-1-(2,3-dihydro-benzo[1,4]dioxin-5-yl)-ethanone prepared by bromination of 1-(2,3-dihydro-benzo[1,4]dioxin-5-yl)-ethanone in methylene chloride while cooling gently with an ice bath. The dibromo compound formed as a by-product is separated off by column chromatography.

Mass spectrum (ESI$^+$): m/z=257, 259 [M+H]$^+$

R$_f$ value: 0.92 (silica gel, methylene chloride)

The following compounds are obtained analogously to Example XXXVI:

(1) 7-(2-bromo-acetyl)-3-methyl-3H-benzooxazol-2-one
  (bromination is carried out in dioxane at 40° C.; the product is contaminated with approx. 20% dibromo compound)
  R$_f$ value: 0.44 (silica gel, petroleum ether/ethyl acetate=1:1)
  Mass spectrum (ESI$^+$): m/z=270, 272 [M+H]$^+$ (2) 1-benzo[1,3]dioxol-4-yl-2-bromo-ethanone
  Mass spectrum (ESI$^+$): m/z=243, 245 [M+H]$^+$
  R$_f$ value: 0.94 (silica gel, methylene chloride)

(3) 2-[2-(2-bromo-acetyl)-phenoxy]-N-ethyl-acetamide
  (bromination is carried out with copper (II) bromide in dioxane)
  Mass spectrum (ESI$^+$): m/z=300, 302 [M+H]$^+$ (4) 4-(2-bromo-acetyl)-3-methyl-3H-benzooxazol-2-one
  R$_f$ value: 0.67 (silica gel, methylene chloride/methanol=99:1)
  Mass spectrum (ESI$^+$): m/z=270, 272 [M+H]$^+$ (5) 2-[2-(2-bromo-acetyl)-phenoxy]-N-methyl-acetamide
  Mass spectrum (ESI$^+$): m/z=386, 388 [M+H]$^+$ (6) 7-(2-bromo-acetyl)-3-[(2-trimethylsilanyl-ethoxy)methyl]-3H-benzooxazol-2-one
  R$_f$ value: 0.84 (silica gel, methylene chloride/methanol=99:1)
  Mass spectrum (ESI$^+$): m/z=384, 386 [M+H]$^+$ (7) 4-(2-bromo-acetyl)-1,3-dimethyl-1,3-dihydro-benzoimidazol-2-one
  R$_f$ value: 0.38 (silica gel, ethyl acetate/petroleum ether=1:1)
  Mass spectrum (ESI$^+$): m/z=283, 285 [M+H]$^+$ (8) 4-(2-bromo-acetyl)-3-[(2-trimethylsilanyl-ethoxy)methyl]-3H-benzooxazol-2-one
  R$_f$ value: 0.82 (silica gel, methylene chloride/methanol=99:1)

(9) 4-(2-bromo-acetyl)-1-ethoxycarbonyl-3-methyl-1,3-dihydro-benzoimidazol-2-one
  R$_f$ value: 0.39 (silica gel, petroleum ether/ethyl acetate=2:1)
  Mass spectrum (ESI$^+$): m/z=341, 343 [M+H]$^+$

(10) 2-bromo-1-(2,2-difluoro-benzo[1,3]dioxol-4-yl)-ethanone
  Mass spectrum (ESI$^-$): m/z=277, 279 [M–H]$^-$

Example XXXVII (2,3-dihydro-benzo[1,4]dioxin-5-yl)-ethanone

Prepared by reacting 1-(2,3-dihydroxy-phenyl)-ethanone with 1,2-dibromoethane in the presence of potassium carbonate in N,N-dimethylformamide at 100° C.

R$_f$ value: 0.43 (silica gel, ethyl acetate/petroleum ether=1:4)

Mass spectrum (ESI$^+$): m/z=179 [M+H]$^+$

Example XXXVIII

1-[(3-methyl-4-oxo-3,4-dihydro-quinazolin-2-yl)methyl]-3-methyl-7-(2-butyn-1-yl)-8-[3-(tert.-butyloxycarbonylamino)-piperidin-1-yl]-xanthine Prepared by reacting 1-[(4-oxo-3,4-dihydro-quinazolin-2-yl)methyl]-3-methyl-7-(2-butyn-1-yl)-8-[3-(tert.-butyloxycarbonylamino)-piperidin-1-yl]-xanthine with methyl iodide in the presence of potassium carbonate in N,N-dimethylformamide at ambient temperature.

R$_f$ value: 0.50 (silica gel, ethyl acetate)

Mass spectrum (ESI$^+$): m/z=589 [M+H]$^+$

The following compounds are obtained analogously to Example XXXVIII:

(1) 7-acetyl-3-methyl-3H-benzooxazol-2-one
  (The methylation is carried out in the presence of sodium carbonate in methanol)
  R$_f$ value: 0.46 (silica gel, petroleum ether/ethyl acetate=1:1)
  Mass spectrum (ESI$^+$): m/z=192 [M+H]$^+$ (2) 4-acetyl-3-methyl-3H-benzooxazol-2-one
  (The methylation is carried out in the presence of sodium carbonate in methanol while refluxing)
  R$_f$ value: 0.67 (silica gel, methylene chloride/methanol=99:1)
  Mass spectrum (ESI$^+$): m/z=192 [M+H]$^+$ (3) 4-acetyl-1,3-dimethyl-1,3-dihydro-benzoimidazol-2-one
  (Carried out in the presence of potassium-tert.butoxide)
  R$_f$ value: 0.40 (silica gel, ethyl acetate/petroleum ether=2:1)
  Mass spectrum (ESI$^+$): m/z=205 [M+H]$^+$ (4) 4-acetyl-1-ethoxycarbonyl-3-methyl-1,3-dihydro-benzoimidazol-2-one
  R$_f$ value: 0.23 (silica gel, petroleum ether/ethyl acetate=2:1)
  Mass spectrum (ESI$^+$): m/z=263 [M+H]$^+$ (5) 1-[(1-methyl-1H-benzoimidazol-2-yl)methyl]-3-methyl-7-(2-butyn-1-yl)-8-[3-(tert.-butyloxycarbonylamino)-piperidin-1-yl]-xanthine
  Mass spectrum (ESI$^+$): m/z=561 [M+H]$^+$ (6) 1-{[1-(2-cyano-ethyl)-1H-benzoimidazol-2-yl]methyl}-3-methyl-7-(2-butyn-1-yl)-8-[3-(tert.-butyloxycarbonylamino)-piperidin-1-yl]-xanthine
  R$_f$ value: 0.50 (silica gel, cyclohexane/ethyl acetate/methanol=5:4:1)
  Mass spectrum (ESI$^+$): m/z=600 [M+H]$^+$ (7) 1-({1-[(methylaminocarbonyl)methyl]-1H-benzoimidazol-2-yl}methyl)-3-methyl-7-(2-butyn-1-yl)-8-[3-(tert.-butyloxycarbonylamino)-piperidin-1-yl]-xanthine
  R$_f$ value: 0.45 (silica gel, cyclohexane/ethyl acetate/methanol=5:4:1)
  Mass spectrum (ESI$^+$): m/z=618 [M+H]$^+$ (8) 1-[(1-benzyl-1H-benzoimidazol-2-yl)methyl]-3-methyl-7-(2-butyn-1-yl)-8-[3-(tert.-butyloxycarbonylamino)-piperidin-1-yl]-xanthine
  R$_f$ value: 0.50 (silica gel, cyclohexane/ethyl acetate/methanol=5:4:1)
  Mass spectrum (ESI$^+$): m/z=637 [M+H]$^+$

Example XXXIX

1-[2-(2-cyanomethylamino-phenyl)-2-oxo-ethyl]-3-methyl-7-(3-methyl-2-buten-1-yl)-8-[3-(tert.-butyloxycarbonylamino)-piperidin-1-yl]-xanthine Prepared by reacting 1-[2-(2-amino-phenyl)-2-oxo-ethyl]-3-methyl-7-(3-methyl-2-buten-1-yl)-8-[3-(tert.-butyloxycarbonylamino)-piperidin-1-yl]-xanthine with paraformaldehyde and potassium cyanide in the presence of zinc chloride in glacial acetic acid at 40° C.

$R_f$ value: 0.45 (silica gel, cyclohexane/ethyl acetate=3:7)
Mass spectrum (ESI$^+$): m/z=605 [M+H]$^+$ Example XL 1-[2-(2-amino-phenyl)-2-oxo-ethyl]-3-methyl-7-(2-butyn-1-yl)-8-[(S)-3-(tert.-butyloxycarbonylamino)-piperidin-1-yl]-xanthine prepared by reduction of 1-[2-(2-nitro-phenyl)-2-oxo-ethyl]-3-methyl-7-(2-butyn-1-yl)-8-[(S)-3-(tert.-butyloxycarbonylamino)-piperidin-1-yl]-xanthine with sodium dithionite in a mixture of methylglycol and water (2:1) at 100° C.

$R_f$ value: 0.34 (silica gel, methylene chloride/methanol=95:5)

The following compounds are obtained analogously to Example XL:
(1) 1-[2-(2-amino-phenyl)-2-oxo-ethyl]-3-methyl-7-(2-butyn-1-yl)-8-[(R)-3-(tert.-butyloxycarbonylamino)-piperidin-1-yl]-xanthine
$R_f$ value: 0.50 (silica gel, cyclohexane/ethyl acetate=4:6)

Example XLI 2-chloromethyl-4-methyl-quinazoline prepared by treatment of 2.95 g of 2-chloromethyl-4-methyl-quinazoline-3-oxide with 6 ml phosphorus trichloride in 150 ml chloroform while refluxing.
Yield: 1.75 g (57% of theory)
$R_f$ value: 0.81 (silica gel, methylene chloride/methanol=95:5)
Mass spectrum (ESI$^+$): m/z=193, 195 [M+H]$^+$ Example XLII 2-chloromethyl-4-dimethylamino-quinazoline A freshly prepared solution of 202 mg of dimethylamine in 3.2 ml of tetrahydrofuran is added dropwise to 500 mg of 4-chloro-2-chloromethyl-quinazoline in 5 ml of tetrahydrofuran while cooling with an ice bath. Then the reaction mixture is stirred for another 3.5 hours while cooling with an ice bath and then for a further 30 minutes at ambient temperature. The solvent is then gently distilled off using a rotary evaporator and the residue is taken up in methylene chloride. The solution is washed with saturated sodium hydrogen carbonate solution and with water, dried over magnesium sulphate and evaporated down. The solid residue is stirred with a little tert.-butylmethylether, suction filtered, washed with petroleum ether and dried in vacuo.
Yield: 323 mg (62% of theory)
$R_f$ value: 0.60 (silica gel, cyclohexane/ethyl acetate=1:1)
Mass spectrum (ESI$^+$): m/z=222, 224 [M+H]$^+$ The following compounds are obtained analogously to Example XLII:
(1) 2-chloromethyl-4-(morpholine-4-yl)-quinazoline
$R_f$ value: 0.50 (silica gel, cyclohexane/ethyl acetate=1:1)
Mass spectrum (ESI$^+$): m/z=264, 266 [M+H]$^+$
(2) 2-chloromethyl-4-(piperidin-1-yl)-quinazoline
$R_f$ value: 0.70 (silica gel, cyclohexane/ethyl acetate=1:1)
Mass spectrum (ESI$^+$): m/z=262, 264 [M+H]$^+$
(3) 4-[4-(tert.-butyloxycarbonyl)-piperazin-1-yl]-2-chloromethyl-quinazoline
$R_f$ value: 0.57 (silica gel, cyclohexane/ethyl acetate=1:1)
Mass spectrum (ESI$^+$): m/z=363, 365 [M+H]$^+$
(4) 2-chloromethyl-4-(pyrrolidin-1-yl)-quinazoline
$R_f$ value: 0.50 (silica gel, cyclohexane/ethyl acetate=1:1)
Mass spectrum (ESI$^+$): m/z=248, 250 [M+H]$^+$
(5) 2-chloromethyl-4-ethoxy-quinazoline
(The reaction is carried out with sodium ethoxide in ethanol at ambient temperature.)
$R_f$ value: 0.50 (silica gel, cyclohexane/ethyl acetate=3:1)
Mass spectrum (ESI$^+$): m/z=223, 225 [M+H]$^+$
(6) 2-chloromethyl-4-isopropyloxy-quinazoline
(The reaction is carried out with sodium isopropoxide in isopropanol at ambient temperature.)
$R_f$ value: 0.70 (silica gel, cyclohexane/ethyl acetate=3:1)
Mass spectrum (ESI$^+$): m/z=237, 239 [M+H]$^+$
(7) 2-chloromethyl-4-phenyloxy-quinazoline
(The reaction is carried out with sodium hydride and phenol in tetrahydrofuran at ambient temperature.)
$R_f$ value: 0.65 (silica gel, cyclohexane/ethyl acetate=3:1)
Mass spectrum (ESI$^+$): m/z=271, 273 [M+H]$^+$ Example XLIII 1-(2-{2-[(ethoxycarbonyl)methylamino]-phenyl}-2-oxo-ethyl)-3-methyl-7-((E)-2-buten-1-yl)-8-[3-(tert.-butyloxycarbonylamino)-piperidin-1-yl]-xanthine A solution of 110 μL of ethyl diazoacetate in 0.5 ml of toluene is added dropwise to 531 mg of 1-[2-(2-amino-phenyl)-2-oxo-ethyl]-3-methyl-7-((E)-2-buten-1-yl)-8-[3-(tert.-butyloxycarbonylamino)-piperidin-1-yl]-xanthine and 10 mg of methyltrioxorhenium in 4.5 ml of toluene at ambient temperature under an argon atmosphere. The reaction mixture is stirred for 15 hours at ambient temperature. Then approx. another 5 mg of methyltrioxorhenium and 20 μL ethyl diazoacetate are added and the reaction mixture is heated to 50° C. for two hours. After cooling to ambient temperature another 5 mg of methyltrioxorhenium and 20 μL ethyl diazoacetate are added. After another 16 hours at ambient temperature the reaction mixture is combined with 5 ml of conc. aqueous ammonia, shaken thoroughly and added to an Extrelut pack. After 15 min it is rinsed with 200 ml methylene chloride. The methylene chloride solution is evaporated down and chromatographed through a silica gel column with cyclohexane/ethyl acetate/isopropanol (8:2:0 to 8:1:1) as eluant.
Yield: 220 mg (36% of theory)
$R_f$ value: 0.40 (silica gel, cyclohexane/ethyl acetate=1:1)
Mass spectrum (ESI$^+$): m/z=638 [M+H]$^+$ Example XLIV 1-[(2-cyano-benzofuran-3-yl)methyl]-3-methyl-7-(2-butyn-1-yl)-8-[3-(tert-butyloxycarbonylamino)-piperidin-1-yl]-xanthine A mixture of 215 mg of 1-{2-[2-cyanomethoxy-phenyl]-2-oxo-ethyl}-3-methyl-7-(2-butyn-1-yl)-8-[3-(tert.-butyloxycarbonylamino)-piperidin-1-yl]-xanthine and 244 mg of caesium carbonate in 4 ml of N,N-dimethylformamide is stirred for two hours at 50° C., then a further three hours at 70° C. For working up the reaction mixture is combined with water and the precipitate formed is suction filtered and dried.

Yield: 130 mg (62% of theory)
Mass spectrum (ESI+): m/z=572 [M+H]+

Example XLV

1-[2-(3-methyl-2-oxo-2,3-dihydro-1H-benzoimidazol-4-yl)-2-oxo-ethyl]-3-methyl-7-(2-butyn-1-yl)-8-[3-(tert.-butyloxycarbonylamino)-piperidin-1-yl]-xanthine Prepared by treating 1-[2-(1-ethoxycarbonyl-3-methyl-2-oxo-2,3-dihydro-1H-benzoimidazol-4-yl)-2-oxo-ethyl]-3-methyl-7-(2-butyn-1-yl)-8-[3-(tert.-butyloxy-carbonylamino)-piperidin-1-yl]-xanthine with 1 N sodium hydroxide solution in methanol at ambient temperature.

$R_f$ value: 0.36 (silica gel, ethyl acetate)
Mass spectrum (ESI+): m/z=605 [M+H]+

Example XLVI 4-acetyl-1-ethoxycarbonyl-1,3-dihydro-benzoimidazol-2-one 5.29 g of diethyldicarbonate and 611 mg of dimethylaminopyridine are added to 1.50 g of 1-(2,3-diamino-phenyl)-ethanone in 75 ml methylene chloride. The reaction mixture is stirred for three hours at ambient temperature, then another 100 mg of dimethylaminopyridine and 1 ml of diethyldicarbonate are added and the mixture is stirred for a further 20 hours at ambient temperature. For working up the reaction mixture is diluted with methylene chloride, washed with 2 N citric acid solution as well as saturated sodium hydrogen carbonate solution and saturated sodium chloride solution, dried over magnesium sulphate and evaporated down. The residue is chromatographed through a silica gel column with petroleum ether/ethyl acetate (3:1 to 1:2) as eluant. The desired product is stirred with a little tert.-butylmethylether, suction filtered, nachwashed with a little ethyl acetate and tert.-butylmethylether and dried.

Yield: 900 mg (36% of theory)
$R_f$ value: 0.15 (silica gel, petroleum ether/ethyl acetate=2:1)
Mass spectrum (ESI+): m/z=249 [M+H]+

Example XLVII

1-[(4-amino-quinazolin-2-yl)methyl]-3-methyl-7-(2-butyn-1-yl)-8-[3-(tert.-butyloxycarbonylamino)-piperidin-1-yl]-xanthine 501 mg of 1-cyanomethyl-3-methyl-7-(2-butyn-1-yl)-8-[3-(tert.-butyloxycarbonylamino)-piperidin-1-yl]-xanthine are added to a mixture of 17 mg of potassium-tert.butoxide in 10 ml of methanol. After brief heating with stirring a clear solution is formed and after about 20 minutes the nitrile has largely reacted to form the iminoester according to thin layer chromatography. 206 mg of 2-amino-benzamidine-hydrochloride are then added and the reaction mixture is refluxed for four hours. After cooling to ambient temperature the precipitate formed is suction filtered, washed with methanol and dried.

Yield: 143 mg (23% of theory)
$R_f$ value: 0.15 (silica gel, ethyl acetate)
Mass spectrum (ESI+): m/z=574 [M+H]+

Example XLVIII 1-(2-phenyl-2-oxo-ethyl)-3-methyl-7-((Z)-2-buten-1-yl)-8-[3-(tert.-butyloxycarbonylamino)-piperidin-1-yl-xanthine 150 mg of 1-(2-phenyl-2-oxo-ethyl)-3-methyl-7-(2-butyn-1-yl)-8-[3-(tert.-butyloxycarbonylamino)-piperidin-1-yl]-xanthine are hydrogenated in a mixture of 5 ml of tetrahydrofuran and 5 ml of methanol in the presence of 30 mg of 5% m palladium on activated charcoal (contaminated with quinoline) at ambient temperature, until the calculated amount of hydrogen has been taken up. Then a spatula tip of activated charcoal is added and the mixture is suction filtered. The filtrate is evaporated down and the crude product is purified by chromatography over a silica gel column with cyclohexane/ethyl acetate (7:3 to 4:6).

Yield: 120 mg (85% of theory)
$R_f$ value: 0.40 (silica gel, cyclohexane/ethyl acetate=4:6)
Mass spectrum (ESI+): m/z=537 [M+H]+

Example XLIX 8-hydroxymethyl-5-methoxy-quinoline 148 mg of sodium hydride (approx. 60% in mineral oil) are added batchwise to a solution of 640 mg of 8-hydroxymethyl-quinolin-5-ol in N,N-dimethylformamide while cooling with an ice bath and the reaction mixture is slowly heated to ambient temperature. After the development of gas has ended, 230 µl methyl iodide are added dropwise while cooling with an ice bath, then the reaction mixture is stirred for approx. another two hours at ambient temperature. For working up it is poured onto ice water, saturated with sodium chloride and extracted with a mixture of diethyl ether and ethyl acetate. The combined extracts are washed with saturated sodium chloride solution, dried over magnesium sulphate and evaporated down. The flask residue is triturated with petroleum ether and the supernatant is decanted. The crude product is purified through a silica gel column with ethyl acetate as eluant.

Yield: 470 mg (68% of theory)
$R_f$ value: 0.70 (silica gel, ethyl acetate)
Mass spectrum (ESI+): m/z=190 [M+H]+

The following compounds are obtained analogously to Example XLIX:

(1) 8-hydroxymethyl-5-methoxy-isoquinoline
$R_f$ value: 0.40 (silica gel, methylene chloride/methanol=10:1)
Mass spectrum (ESI+): m/z=190 [M+H]+

Example L 8-hydroxymethyl-quinolin-5-ol 3.40 g of quinolin-5-ol is combined with 8 ml of conc. hydrochloric acid and 8 ml of 37% formalin solution while cooling with an ice bath. Then hydrogen chloride gas is piped through the reaction mixture for about two hours, while the temperature slowly rises. The reaction mixture is stirred first overnight while cooling with an ice bath, then at ambient temperature and then evaporated down in vacuo. The flask residue is taken up in water, covered with a layer of diethyl ether and adjusted to pH 10 while cooling with an ice bath and vigorously stirring with dilute ammonia solution. After another two hours' vigorous stirring at ambient temperature the organic phase is separated off and the aqueous phase is extracted with diethyl ether. The combined organic phases are washed with water and saturated sodium chloride solution, dried over magnesium sulphate and evaporated down. The flask residue is chromatographed through a silica gel column with methylene chloride/methanol (20:1) as eluant.

Yield: 660 mg (16% of theory)

Mass spectrum (ESI$^+$): m/z=176 [M+H]$^+$

The following compounds are obtained analogously to Example L:

(1) 8-hydroxymethyl-isoquinolin-5-ol $R_f$ value: 0.50 (silica gel, methylene chloride/methanol=5:1)

Mass spectrum (ESI$^+$): m/z=176 [M+H]$^+$

Example LI

1-[(2-cyclopropyl-quinazolin-4-yl)methyl]-3-methyl-7-[(1-cyclopenten-1-yl)methyl]-8-[3-(tert.-butyloxy-carbonylamino)-piperidin-1-yl]-xanthine A mixture of 250 mg of 1-(2-{2-[(cyclopropylcarbonyl)amino]-phenyl}-2-oxo-ethyl)-3-methyl-7-[(1-cyclopenten-1-yl)methyl]-8-[3-(tert.-butyloxycarbonylamino)-piperidin-1-yl]-xanthine and 7.5 ml of ethanolic ammonia solution (6 M) is heated to 150° C. for seven hours in a bomb. For working up the reaction mixture is evaporated down and chromatographed through a silica gel column with methylene chloride/methanol (100:0 to 70:30) as eluant. The contaminated product fraction is evaporated down and again purified through a reversed phase HPLC column with water/acetonitrile/trifluoroacetic acid (65:15:0.08 to 0:100:0.1) as eluant. The product fractions are evaporated down, made alkaline with dilute sodium hydroxide solution and extracted with methylene chloride. The combined extracts are dried over magnesium sulphate and evaporated down.

Yield: 40 mg (14% of theory)

$R_f$ value: 0.40 (silica gel, methylene chloride/ethyl acetate=1:1)

Mass spectrum (ESI$^+$): m/z=627 [M+H]$^+$

Example LII 4-(2-bromo-acetyl)-1,3-bis-[(2-trimethylsilanyl-ethoxy)methyl]-1,3-dihydro-benzoimidazol-2-one 520 mg of 2-pyrrolidinone-hydrotribromide and 89 mg of 2-pyrrolidinone are added to 420 mg of 4-acetyl-1,3-bis-[(2-trimethylsilanyl-ethoxy)methyl]-1,3-dihydro-benzoimidazol-2-one in 5 ml of tetrahydrofuran under an argon atmosphere. The reaction mixture is refluxed for two hours and then suction filtered while still warm. The filter cake is washed with tetrahydrofuran and the filtrate is evaporated down, leaving 660 mg of a yellowish-brown solid. This is stirred with a little methanol, suction filtered, washed with some methanol and dried. The crude product is reacted further without any more purification.

Yield: 430 mg (87% of theory)

$R_f$ value: 0.23 (silica gel, petroleum ether/ethyl acetate=9:1)

Mass spectrum (EI): m/z=514, 516 [M]$^+$

The following compounds are obtained analogously to Example LII:

(1) 7-(2-bromo-acetyl)-1-(tert.-butyloxycarbonyl)-1H-indole $R_f$ value: 0.33 (silica gel, petroleum ether/ethyl acetate=9:1)

Mass spectrum (ESI$^+$): m/z=338, 340 [M+H]$^+$ (2) 2-bromo-1-(3-isopropyloxy-phenyl)-ethanone (Carried out with phenyltrimethylammonium tribromide in methylene chloride)

$R_f$ value: 0.39 (silica gel, cyclohexane/ethyl acetate=9:1)

(3) 2-bromo-1-(3-difluoromethoxy-phenyl)-ethanone (Carried out with phenyltrimethylammonium tribromide in methylene chloride)

$R_f$ value: 0.24 (ready-made reversed phase TLC plate (E. Merck), acetonitrile/water/trifluoroacetic acid=50:50:1)

Example LIII methyl 3-methyl-imidazo[1,2-a]pyridine-2-carboxylate

A mixture of 1.91 g of 2-aminopyridine and 4.40 g of methyl 3-bromo-2-oxo-butyrate in 40 ml of ethanol is refluxed for 6 hours and then left to stand for 2 days at ambient temperature. The solvent is distilled off using the rotary evaporator and the crude product is purified by chromatography over a silica gel column with methylene chloride/methanolic ammonia solution (95:4:1 to 90:9:1) as eluant. 560 mg of the ethyl ester are isolated as the by-product.

Yield: 2.09 g (54% of theory)

$R_f$ value: 0.20 (silica gel, methylene chloride/ethyl acetate=1:1)

Mass spectrum (ESI$^+$): m/z=191 [M+H]$^+$

Example LIV 2-chloromethyl-4-isopropyl-quinazoline

Dry hydrogen chloride gas is piped through a solution of 2.86 g of 1-(2-amino-phenyl)-2-methyl-propan-1-one and 1.33 ml of chloroacetonitrile in 14 ml dioxane with stirring at ambient temperature for approx. five hours. Then the dioxane is largely distilled off in a water jet vacuum. The honey-like residue is combined with ice water and the resulting suspension is made alkaline with saturated potassium carbonate solution while cooling with an ice bath. The precipitate is suction filtered, washed with water and dried. The crude product is purified by chromatography over a silica gel column with petroleum ether/methylene chloride (8:2 to 0:1) as eluant.

Yield: 1.80 g (58% of theory)

$R_f$ value: 0.30 (silica gel, methylene chloride/petroleum ether=1:1)

Mass spectrum (ESI$^+$): m/z=221, 223 [M+H]$^+$

Example LV 1-chloromethyl-3-trifluoromethyl-3,4-dihydro-isoquinoline 530 mg of N-(1-benzyl-2,2,2-trifluoro-ethyl)-2-chloro-acetamide (prepared by reacting 1-benzyl-2,2,2-trifluoro-ethylamine with chloroacetyl chloride in the presence of triethylamine) and 0.74 ml of phosphorus oxychloride are added to 4.00 g of polyphosphoric acid. The viscous mixture is stirred for 1.5 hours at 130° C. For working up the reaction mixture is cooled and combined with ice water, stirred vigorously for ten minutes and suction filtered. The filter cake is dissolved in ethyl acetate and the solution is dried over magnesium sulphate and evaporated down, leaving a white solid.

Yield: 415 mg (84% of theory)

$R_f$ value: 0.55 (aluminium oxide, petroleum ether/ethyl acetate=10:1)

Mass spectrum (ESI$^+$): m/z=248, 250 [M+H]$^+$

The following compound is obtained analogously to Example LV:

(1) 1-methyl-3-trifluoromethyl-3,4-dihydro-isoquinoline (The starting material N-(1-benzyl-2,2,2-trifluoro-ethyl)-acetamide is obtained by reacting 1-benzyl-2,2,2-trifluoro-ethylamine with acetic anhydride.)

Example LVI 3-bromomethyl-1-(1-cyano-1-methyl-ethyl)-isoquinoline

A mixture of 375 mg of 1-(1-cyano-1-methyl-ethyl)-3-methyl-isoquinoline and 321 mg of N-bromosuccinimide in 5 ml carbon tetrachloride is combined with a spatula tip of 2,2-azoisobutyric acid dinitrile and refluxed for about six hours. The cooled reaction mixture is filtered and evaporated down. The flask residue is reacted further without any more purification.

$R_f$ value: 0.70 (silica gel, cyclohexane/ethyl acetate=3:1)

The following compounds are obtained analogously to Example LVI:

(1) 6-bromomethyl-1-[(2-trimethylsilanyl-ethoxy)methyl]-1H-quinolin-2-one (2) 1-bromomethyl-4-bromo-3-methoxy-isoquinoline (3) 2-bromomethyl-[1,5]naphthyridine Mass spectrum (ESI$^+$): m/z=223, 225 [M+H]$^+$ (4) 5-bromomethyl-[1,6]naphthyridine $R_f$ value: 0.48 (silica gel, ethyl acetate/methanol=98:2)

(5) 7-bromomethyl-5-phenyl-quinoxaline $R_f$ value: 0.85 (silica gel, methylene chloride/methanol=95:5)

Mass spectrum (ESI$^+$): m/z=299, 301 [M+H]$^+$ (6) 4-bromomethyl-[1,5]naphthyridine $R_f$ value: 0.56 (silica gel, methylene chloride/ethyl acetate=7:3)

Mass spectrum (ESI$^+$): m/z=223, 225 [M+H]$^+$ (7) 1-bromomethyl-3-trifluoromethyl-isoquinoline Mass spectrum (ESI$^+$): m/z=290, 292 [M+H]$^+$ (8) 1-bromomethyl-3-difluoromethyl-isoquinoline Mass spectrum (ESI$^+$): m/z=272, 274 [M+H]$^+$ (9) 1-bromomethyl-4-chloro-3-methoxy-isoquinoline

Example LVII 1-(1-cyano-1-methyl-ethyl)-3-methyl-isoquinoline 3.30 g of 2,2-azoisobutyric acid dinitrile are added to 1.60 g of 3-methyl-isoquinoline-N-oxide in 30 ml of toluene. The reaction mixture is stirred for six hours at 85° C. and then left to stand for two days at ambient temperature. For working up the reaction mixture is extracted with 20% hydrochloric acid. The combined aqueous phases are diluted with methylene chloride, made alkaline with saturated potassium carbonate solution while cooling with an ice bath and extracted with methylene chloride. The combined methylene chloride extracts are dried over magnesium sulphate and evaporated down. The residue is chromatographed through a silica gel column with cyclohexane as eluant.

Yield: 375 mg (18% of theory)

Mass spectrum (ESI$^+$): m/z=211 [M+H]$^+$ $R_f$ value: 0.75 (silica gel, cyclohexane/ethyl acetate=3:1)

Example LVIII 1-(2-cyanoimino-2-phenyl-ethyl)-3-methyl-7-(2-butyn-1-yl)-8-[3-(tert.-butyloxycarbonylamino)-piperidin-1-yl]-xanthine (E/Z-mixture)

0.48 ml of a 1M solution of titanium tetrachloride in methylene chloride are added dropwise to 244 mg of 1-(2-phenyl-2-oxo-ethyl)-3-methyl-7-(2-butyn-1-yl)-8-[3-(tert.-butyloxycarbonylamino)-piperidin-1-yl]-xanthine in 7 ml of methylene chloride. Then 88 µl of 1,3-bis(trimethylsilyl)carbodiimide are added and the mixture is stirred for four hours at ambient temperature. For working up the reaction mixture is diluted with methylene chloride and poured onto ice water. The organic phase is washed with 0.5 N citric acid, dried over magnesium sulphate and evaporated down. The crude product is purified by chromatography over a silica gel column with methylene chloride/methanol (98:2 to 95:5) as eluant.

Yield: 206 mg (97% of theory)

Mass spectrum (ESI$^-$): m/z=557 [M−H]$^-$ $R_f$ value: 0.16 (silica gel, cyclohexane/ethyl acetate=1:1)

Example LIX

1-[(1H-benzoimidazol-2-yl)methyl]-3-methyl-7-(2-butyn-1-yl)-8-[3-(tert.-butyloxycarbonylamino)-piperidin-1-yl]-xanthine 350 mg of 1-[(2-amino-phenylaminocarbonyl)methyl]-3-methyl-7-(2-butyn-1-yl)-8-[3-(tert.-butyloxycarbonylamino)-piperidin-1-yl]-xanthine are refluxed in 3 ml glacial acetic acid for two hours. Then the reaction mixture is evaporated down, the flask residue is combined with 5 ml of 1 M sodium hydroxide solution and washed with methylene chloride. Then the aqueous phase is acidified with 1 M hydrochloric acid and extracted with methylene chloride. The combined extracts are evaporated down and chromatographed through a silica gel column with cyclohexane/ethyl acetate/methanol (6:4:0 to 5:4:1) as eluant.

Yield: 250 mg of (74% of theory)

Mass spectrum (ESI$^+$): m/z=547 [M+H]$^+$

Example LX

Ethyl 3,4-dimethyl-6,7-dihydro-5H-[2]pyrindin-1-carboxylate

Prepared by treating 1.16 g of ethyl 3,4-dimethyl-4a-(pyrrolidin-1-yl)-5,6,7,7a-tetrahydro-4aH-[2]pyrindin-1-carboxylate with 1.08 g of 70% 3-chloro-perbenzoic acid in 50 ml methylene chloride at ambient temperature.

Yield: 850 mg (97% of theory)

$R_f$ value: 0.30 (aluminium oxide, petroleum ether/ethyl acetate=5:1)

Mass spectrum (ESI$^+$): m/z=220 [M+H]$^+$

The following compounds are obtained analogously to Example LX:

(1) ethyl 3,4-dimethyl-5,6,7,8-tetrahydro-isoquinoline-1-carboxylate
$R_f$ value: 0.35 (aluminium oxide, petroleum ether/ethyl acetate=5:1)
Mass spectrum (ESI$^+$): m/z=234 [M+H]$^+$

Example LXI

Ethyl 3,4-dimethyl-4a-(pyrrolidin-1-yl)-5,6,7,7a-tetrahydro-4aH-[2]pyrindin-1-carboxylate Prepared by reacting 2.50 g of ethyl 5,6-dimethyl-[1,2,4] triazin-3-carboxylate with 2.74 g of 1-(cyclopenten-1-yl)-pyrrolidine in 25 ml chloroform at ambient temperature.
Yield: 3.00 g (75% of theory)
$R_f$ value: 0.60 (aluminium oxide, petroleum ether/ethyl acetate=5:1)
Mass spectrum (ESI$^+$): m/z=291 [M+H]$^+$
The following compounds are obtained analogously to Example LXI:
(1) ethyl 3,4-dimethyl-4a-(pyrrolidin-1-yl)-4a,5,6,7,8,8a-hexahydro-isoquinoline-1-carboxylate
$R_f$ value: 0.60 (aluminium oxide, petroleum ether/ethyl acetate=5:1)
Mass spectrum (ESI$^+$): m/z=305 [M+H]$^+$

Example LXII

Methyl 2,3,8-trimethyl-quinoxalin-6-carboxylate

Prepared by reacting 1.60 g of methyl 3,4-diamino-5-methyl-benzoate with 0.86 ml diacetyl in a mixture of water and ethanol while refluxing.
Yield: 1.53 g (80% of theory)
$R_f$ value: 0.63 (silica gel, cyclohexane/ethyl acetate=1:1)
Mass spectrum (ESI$^+$): m/z=231 [M+H]$^+$
The following compounds are obtained analogously to Example LXII:
(1) methyl 8-methyl-quinoxalin-6-carboxylate
(reaction is carried out with glyoxal in water.)
$R_f$ value: 0.55 (silica gel, cyclohexane/ethyl acetate=1:1)
Mass spectrum (ESI$^+$): m/z=203 [M+H]$^+$
(2) 5-bromo-7-methyl-quinoxaline
(reaction is carried out with glyoxal in a water/ethanol mixture.)
$R_f$ value: 0.75 (silica gel, methylene chloride/methanol=95:5)
Mass spectrum (ESI$^+$): m/z=223, 225 [M+H]$^+$

Example LXIII

Methyl 3,4-diamino-5-methyl-benzoate

Prepared by reduction of methyl 3-nitro-4-amino-5-methyl-benzoate at a partial hydrogen pressure of 50 psi in the presence of Raney nickel in methanol at ambient temperature.
$R_f$ value: 0.40 (silica gel, tert.-butylmethylether)

Example LXIV

Methyl 3-nitro-4-amino-5-methyl-benzoate

Prepared by treating 3-nitro-4-acetylamino-5-methyl-benzoic acid with hydrogen chloride gas in methanol at ambient temperature and subsequently heating while refluxing.

Mass spectrum (ESI$^+$): m/z=211 [M+H]$^+$
$R_f$ value: 0.75 (silica gel, tert.-butylmethylether/acetic acid=99:1)

Example LXV 1-(2-phenyl-2-oxo-ethyl)-3-methyl-7-((E)-1-buten-1-yl)-8-bromo-xanthine 0.13 ml 35% hydrogen peroxide solution are added to 290 mg of 1-(2-phenyl-2-oxo-ethyl)-3-methyl-7-(1-phenylsulphanyl-butyl)-8-bromo-xanthine in 6 ml hexafluoroisopropanol. The reaction mixture is stirred for one hour at ambient temperature, diluted with methylene chloride and washed with sodium thiosulphate solution. The organic phase is dried over magnesium sulphate and evaporated down. The flask residue is taken up in 6 ml of toluene and refluxed for eight hours. Then the toluene is distilled off in vacuo and the crude product is purified through a silica gel column with methylene chloride/methanol (100:0 to 95:5) as eluant.
Yield: 104 mg (45% of theory)
$R_f$ value: 0.61 (silica gel, methylene chloride/methanol=95:5)
Mass spectrum (ESI$^+$): m/z=417, 419 [M+H]$^+$
The following compounds are obtained analogously to Example LXV:
(1) 3-methyl-7-(3-methyl-1-buten-1-yl)-8-bromo-xanthine
$R_f$ value: 0.24 (silica gel, methylene chloride/methanol=95:5)
Mass spectrum (ESI$^+$): m/z=313, 315 [M+H]$^+$

Example LXVI 1-methanesulphonyloxymethyl-4-difluoromethoxy-naphthalene

Prepared by reacting (4-difluoromethoxy-naphthalen-1-yl)-methanol with methanesulphonic acid chloride in methylene chloride in the presence of triethylamine.
The following compounds are obtained analogously to Example LXVI:
(1) (E)-1-methanesulphonyloxy-3-(2-nitro-phenyl)-2-propene
(2) (E)-1-methanesulphonyloxy-3-pentafluorophenyl-2-propene
(3) (E)-1-methanesulphonyloxy-3-(2-trifluoromethyl-phenyl)-2-propene
(4) (E)-1-methanesulphonyloxy-3-(3-trifluoromethyl-phenyl)-2-propene
(5) (E)-1-methanesulphonyloxy-3-(4-trifluoromethyl-phenyl)-2-propene

Example LXVII 7-methyl-5-phenyl-quinoxaline

A mixture of 400 mg of 5-bromo-7-methyl-quinoxaline, 244 mg of phenylboric acid and 100 mg of tetrakis(triphenylphosphine)palladium in 12 ml dioxane, 4 ml of methanol and 3.6 ml 1 M aqueous sodium carbonate solution is refluxed for three hours under an argon atmosphere. Then the reaction mixture is evaporated down and the residue is distributed between ethyl acetate and water. The ethyl acetate phase is separated off, dried over magnesium sulphate and evaporated down. The crude product is purified by chromatography over a silica gel column with cyclohexane/ethyl acetate (85:15 to 70:30) as eluant.

Yield: 390 mg (66% of theory)
$R_f$ value: 0.36 (silica gel, petroleum ether/ethyl acetate=5:1)
Mass spectrum (ESI$^+$): m/z=221 [M+H]$^+$ Example LXVIII 1-methyl-3-trifluoromethyl-isoquinoline Prepared by treating 905 mg of 1-chloromethyl-3-trifluoromethyl-3,4-dihydro-isoquinoline with 420 mg of potassium-tert.butoxide in 10 ml of tetrahydrofuran at ambient temperature.
Yield: 755 mg of (98% of theory)
Mass spectrum (ESI$^+$): m/z=212 [M+H]$^+$
The following compounds are obtained analogously to Example LXVIII:
(1) 1-methyl-3-difluoromethyl-isoquinoline
(Prepared from 1-methyl-3-trifluoromethyl-3,4-dihydro-isoquinoline)
Mass spectrum (ESI$^+$): m/z=194 [M+H]$^+$ Example LXIX 4-chloro-3-methoxy-1-methyl-isoquinoline Prepared by treating 3-methoxy-1-methyl-isoquinoline with sulphuryl chloride in methylene chloride.
$R_f$ value: 0.30 (silica gel, cyclohexane)
Mass spectrum (ESI$^+$): m/z=208, 210 [M+H]$^+$ Example LXX 3-cyclopropyl-8-bromo-xanthine Prepared by reacting 3-cyclopropyl-xanthine with bromine in the presence of potassium carbonate in acetonitrile at 60° C.
$R_f$ value: 0.65 (ready-made reversed phase TLC plate (E. Merck), acetonitrile/water/trifluoroacetic acid=50:50:1)
Mass spectrum (ESI$^+$): m/z=271, 273 [M+H]$^+$ Example LXXI Ethyl 1,2,3,4-tetrahydro-phenanthridin-6-yl-carboxylate Analogously to the method described by Gonsalves et al. (*Tetrahedron* 1992, 48, 6821) a solution of 3.90 g of ethyl 5,6,7,8-tetrahydro-benzo[1,2,4]triazin-3-carboxylate (Sagi et al., *Heterocycles* 1989, 29, 2253) in 20 ml dioxane is refluxed. Then 8.22 g of anthranilic acid and 7.02 g of isoamylnitrite, in each case dissolved in 20 ml dioxane, are simultaneously added dropwise within 25 minutes by means of two dropping funnels. The reaction mixture is refluxed for a further 30 minutes. For working up the cooled deep-brown reaction solution is diluted with 150 ml diethyl ether, washed with 100 ml of 2 N sodium hydroxide solution and with water, dried over magnesium sulphate and evaporated down. The brown, oily flask residue is chromatographed through a silica gel column with ethyl acetate/petroleum ether (20:80 to 50:50) as eluant. The product obtained is still somewhat contaminated, but is reacted further without any more purification.
Yield: 380 mg (8% of theory)
$R_f$ value: 0.55 (silica gel, petroleum ether/ethyl acetate=2:1)
Mass spectrum (ESI$^+$): m/z=256 [M+H]$^+$ Preparation of the Final Compounds Example 1

1,3-dimethyl-7-(2,6-dicyano-benzyl)-8-(3-amino-piperidin-1-yl)-xanthine 129 mg of 3-amino-piperidine-dihydrochloride are added to a mixture of 298 mg of 1,3-dimethyl-7-(2,6-dicyano-benzyl)-8-bromo-xanthine and 420 mg of potassium carbonate in 9 ml of N,N-dimethylformamide. The reaction mixture is stirred for three hours at 80° C. For working up the mixture is diluted with methylene chloride and washed with saturated sodium chloride solution. The organic phase is dried over magnesium sulphate and evaporated down. The crude product is purified by chromatography through a silica gel column with methylene chloride/methanol/conc. methanolic ammonia (95:5:1 to 80:20:1) as eluant.
Yield: 43 mg (14% of theory)
$R_f$ value: 0.67 (silica gel, methylene chloride/methanol/conc. aqueous ammonia=80:20:1)
Mass spectrum (ESI$^+$): m/z=419 [M+H]$^+$
The following compounds are obtained analogously to Example 1:
(1) 1-(2-cyano-ethyl)-3-methyl-7-(2-cyano-benzyl)-8-(3-amino-piperidin-1-yl)-xanthine
$R_f$ value: 0.35 (silica gel, methylene chloride/methanol=9:1)
Mass spectrum (ESI$^+$): m/z=433 [M+H]$^+$ Example 2

1-(2-{2-[(ethoxycarbonyl)methoxy]-phenyl}-2-oxo-ethyl)-3-methyl-7-(3-methyl-2-buten-1-yl)-8-(3-amino-piperidin-1-yl)-xanthine A solution of 209 mg of 1-(2-{2-[(ethoxycarbonyl)methoxy]-phenyl}-2-oxo-ethyl)-3-methyl-7-(3-methyl-2-buten-1-yl)-8-[3-(tert.-butyloxycarbonylamino)-piperidin-1-yl]-xanthine in 4 ml methylene chloride is combined with 1 ml of trifluoroacetic acid and stirred for half an hour at ambient temperature. For working up the reaction mixture is diluted with methylene chloride and washed with saturated potassium carbonate solution. The organic phase is dried, evaporated down and chromatographed through a silica gel column with methylene chloride/methanol (1:0 to 4:1) as eluant.
Yield: 153 mg of (87% of theory)
Mass spectrum (ESI$^+$): m/z=553 [M+H]$^+$
The following compounds are obtained analogously to Example 2:
(1) 1-(2-{2-[(aminocarbonyl)methoxy]-phenyl}-2-oxo-ethyl)-3-methyl-7-(3-methyl-2-buten-1-yl)-8-(3-amino-piperidin-1-yl)-xanthine
Mass spectrum (ESI$^+$): m/z=524 [M+H]$^+$
(2) 1-(2-{3-[(methanesulphinyl)methoxy]-phenyl}-2-oxo-ethyl)-3-methyl-7-(3-methyl-2-buten-1-yl)-8-(3-amino-piperidin-1-yl)-xanthine
$R_f$ value: 0.58 (ready-made reversed phase TLC plate (E. Merck), acetonitrile/water/trifluoroacetic acid=100:100:0.1)
Mass spectrum (ESI$^+$): m/z=543 [M+H]$^+$ (3) 1-(1-methyl-2-oxo-2-phenyl-ethyl)-3-methyl-7-(3-methyl-2-buten-1-yl)-8-(3-amino-piperidin-1-yl)-xanthine
Mass spectrum (ESI$^+$): m/z=465 [M+H]$^+$ (4) 1-(2-phenoxy-ethyl)-3-methyl-7-(2-cyano-benzyl)-8-(3-amino-piperidin-1-yl)-xanthine
R$_f$ value: 0.50 (silica gel, methylene chloride/methanol=9:1)
Mass spectrum (ESI$^+$): m/z=500 [M+H]$^+$ (5) 1-(2-phenyl-2-oxo-ethyl)-7-(3-methyl-2-buten-1-yl)-8-(3-amino-piperidin-1-yl)-xanthine
R$_f$ value: 0.58 (silica gel, methylene chloride/methanol/conc. aqueous ammonia=80:20:1)
Mass spectrum (ESI$^-$): m/z=435 [M−H]$^-$ (6) 1-(2-{3-[(ethoxycarbonyl)methoxy]-phenyl}-2-oxo-ethyl)-3-methyl-7-(3-methyl-2-buten-1-yl)-8-(3-amino-piperidin-1-yl)-xanthine
Mass spectrum (ESI$^+$): m/z=553 [M+H]$^+$ (7) 1-(2-{2-[(methylaminocarbonyl)methoxy]-phenyl}-2-oxo-ethyl)-3-methyl-7-(3-methyl-2-buten-1-yl)-8-(3-amino-piperidin-1-yl)-xanthine
Mass spectrum (ESI$^+$): m/z=538 [M+H]$^+$ (8) 1-(2-{2-[(dimethylaminocarbonyl)methoxy]-phenyl}-2-oxo-ethyl)-3-methyl-7-(3-methyl-2-buten-1-yl)-8-(3-amino-piperidin-1-yl)-xanthine
Mass spectrum (ESI$^+$): m/z=552 [M+H]$^+$ (9) 1-(2-methoxy-ethyl)-3-methyl-7-(2-cyano-benzyl)-8-(3-amino-piperidin-1-yl)-xanthine
R$_f$ value: 0.40 (silica gel, methylene chloride/methanol=9:1)
Mass spectrum (ESI$^+$): m/z=438 [M+H]$^+$

(10) 1-methyl-3-[(methoxycarbonyl)methyl]-7-(2-cyano-benzyl)-8-(3-amino-piperidin-1-yl)-xanthine
R$_f$ value: 0.40 (silica gel, methylene chloride/methanol=9:1)
Mass spectrum (ESI$^+$): m/z=452 [M+H]$^+$

(11) 1-methyl-3-cyanomethyl-7-(2-cyano-benzyl)-8-(3-amino-piperidin-1-yl)-xanthine
(Carried out with 5-6 M isopropanolic hydrochloric acid in methylene chloride)
R$_f$ value: 0.20 (silica gel, methylene chloride/methanol=9:1)
Mass spectrum (ESI$^+$): m/z=419 [M+H]$^+$

(12) 1-methyl-3-(2-propyn-1-yl)-7-(2-cyano-benzyl)-8-(3-amino-piperidin-1-yl)-xanthine
R$_f$ value: 0.40 (silica gel, methylene chloride/methanol=9:1)
Mass spectrum (ESI$^+$): m/z=418 [M+H]$^+$

(13) 1-{2-[3-(2-oxo-imidazolidin-1-yl)-phenyl]-2-oxo-ethyl}-3-methyl-7-(3-methyl-2-buten-1-yl)-8-(3-amino-piperidin-1-yl)-xanthine
R$_f$ value: 0.54 (ready-made reversed phase TLC plate (E. Merck), acetonitrile/water/trifluoroacetic acid=100:100:0.1)
Mass spectrum (ESI$^+$): m/z=535 [M+H]$^+$

(14) 1-methyl-3-(2-propen-1-yl)-7-(2-cyano-benzyl)-8-(3-amino-piperidin-1-yl)-xanthine
R$_f$ value: 0.40 (silica gel, methylene chloride/methanol=9:1)
Mass spectrum (ESI$^+$): m/z=420 [M+H]$^+$

(15) 1-(2-phenyl-2-oxo-ethyl)-3-methyl-7-(2-butyn-1-yl)-8-(3-amino-piperidin-1-yl)-xanthine
Mass spectrum (ESI$^+$): m/z=435 [M+H]$^+$

(16) 1-(2-{2-[(ethylcarbonyl)amino]-phenyl}-2-oxo-ethyl)-3-methyl-7-(3-methyl-2-buten-1-yl)-8-(3-amino-piperidin-1-yl)-xanthine
R$_f$ value: 0.50 (ready-made reversed phase TLC plate (E. Merck), acetonitrile/water/trifluoroacetic acid=100:100:0.1)
Mass spectrum (ESI$^+$): m/z=522 [M+H]$^+$

(17) 1-methyl-3-phenyl-7-(2-cyano-benzyl)-8-(3-amino-piperidin-1-yl)-xanthine
R$_f$ value: 0.40 (silica gel, methylene chloride/methanol=9:1)
Mass spectrum (ESI$^+$): m/z=456 [M+H]$^+$

(18) 1-[2-(2-amino-phenyl)-2-oxo-ethyl]-3-methyl-7-(3-methyl-2-buten-1-yl)-8-((S)-3-amino-piperidin-1-yl)-xanthine
R$_f$ value: 0.50 (ready-made reversed phase TLC plate (E. Merck), acetonitrile/water/trifluoroacetic acid=50:50:0.1)
Mass spectrum (ESI$^+$): m/z=466 [M+H]$^+$

(19) 1-(2-phenyl-2-oxo-ethyl)-3-cyanomethyl-7-(3-methyl-2-buten-1-yl)-8-(3-amino-piperidin-1-yl)-xanthine
R$_f$ value: 0.07 (silica gel, methylene chloride/methanol/conc. aqueous ammonia=90:10:1)
Mass spectrum (ESI$^+$): m/z=476 [M+H]$^+$

(20) 1-[(quinolin-2-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
R$_f$ value: 0.50 (silica gel, methylene chloride/methanol/conc. aqueous ammonia=90:10:1)
Mass spectrum (ESI$^+$): m/z=474 [M+H]$^+$

(21) 1-[(2-oxo-2H-chromen-4-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
Mass spectrum (ESI$^+$): m/z=491 [M+H]$^+$
R$_f$ value: 0.16 (silica gel, methylene chloride/methanol/conc. aqueous ammonia=95:5:0.1)

(22) 1-[(cinnolin-4-yl)methyl]-3-methyl-7-(3-methyl-2-buten-1-yl)-8-(3-amino-piperidin-1-yl)-xanthine (1:1 mixture with 1-[(1,4-dihydro-cinnolin-4-yl)methyl]-3-methyl-7-(3-methyl-2-buten-1-yl)-8-(3-amino-piperidin-1-yl)-xanthine)
(Carried out with 5-6 M isopropanolic hydrochloric acid in methylene chloride)
R$_f$ value: 0.49 (silica gel, methylene chloride/methanol/conc. aqueous ammonia=90:10:1)
Mass spectrum (ESI$^+$): m/z=475 [M+H]$^+$

(23) 1-[(1-methyl-2-oxo-1,2-dihydro-quinolin-4-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
Melting point: 178-181° C.
Mass spectrum (ESI$^+$): m/z=504 [M+H]$^+$

(24) 1-[(4-oxo-3,4-dihydro-phthalazin-1-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
R$_f$ value: 0.06 (silica gel, methylene chloride/methanol/conc. aqueous ammonia=95:5:0.1)
Mass spectrum (ESI$^+$): m/z=491 [M+H]$^+$

(25) 1-[(quinazolin-4-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
R$_f$ value: 0.48 (silica gel, methylene chloride/methanol/conc. aqueous ammonia=90:10:1)
Mass spectrum (ESI$^+$): m/z=475 [M+H]$^+$

(26) 1-[(5-methyl-3-phenyl-isoxazol-4-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.40 (silica gel, methylene chloride/methanol/conc. aqueous ammonia=90:10:0.1)

Mass spectrum (ESI$^+$): m/z=504 [M+H]$^+$

(27) 1-[(isoquinoline-3-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.51 (silica gel, methylene chloride/methanol/conc. aqueous ammonia=90:10:1)

Mass spectrum (ESI$^+$): m/z=474 [M+H]$^+$

(28) 1-[(3-phenyl-[1,2,4]oxadiazol-5-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.23 (silica gel, methylene chloride/methanol/conc. aqueous ammonia=95:5:1)

Mass spectrum (ESI$^+$): m/z=491 [M+H]$^+$

(29) 1-[(4-phenyl-pyridin-2-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.51 (silica gel, methylene chloride/methanol/conc. aqueous ammonia=90:10:1)

Mass spectrum (ESI$^+$): m/z=500 [M+H]$^+$

(30) 1-[(5-phenyl-pyridin-2-yl)methyl]-3-methyl-7-(3-methyl-2-buten-1-yl)-8-(3-amino-piperidin-1-yl)-xanthine (Carried out with 5-6 M isopropanolic hydrochloric acid in methylene chloride)

R$_f$ value: 0.58 (silica gel, methylene chloride/methanol/conc. aqueous ammonia=90:10:1)

Mass spectrum (ESI$^+$): m/z=500 [M+H]$^+$

(31) 1-[(3-methyl-4-oxo-3,4-dihydro-phthalazin-1-yl)methyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product precipitated as the hydrochloride)

R$_f$ value: 0.55 (silica gel, methylene chloride/methanol/conc. aqueous ammonia=90:10:0.1)

Mass spectrum (ESI$^+$): m/z=505 [M+H]$^+$

(32) 1-[2-(3-methylsulphanyl-phenyl)-2-oxo-ethyl]-3-methyl-7-(3-methyl-2-buten-1-yl)-8-(3-amino-piperidin-1-yl)-xanthine R$_f$ value: 0.34 (silica gel, methylene chloride/methanol/conc. aqueous ammonia=90:10:1)

Mass spectrum (ESI$^+$): m/z=497 [M+H]$^+$

(33) 1-[2-(3-methanesulphinyl-phenyl)-2-oxo-ethyl]-3-methyl-7-(3-methyl-2-buten-1-yl)-8-(3-amino-piperidin-1-yl)-xanthine R$_f$ value: 0.21 (silica gel, methylene chloride/methanol/conc. aqueous ammonia=90:10:1)

Mass spectrum (ESI$^+$): m/z=513 [M+H]$^+$

(34) 1-[2-(3-methanesulphonyl-phenyl)-2-oxo-ethyl]-3-methyl-7-(3-methyl-2-buten-1-yl)-8-(3-amino-piperidin-1-yl)-xanthine R$_f$ value: 0.66 (ready-made reversed phase TLC plate (E. Merck), acetonitrile/water/trifluoroacetic acid=50:50:1)

Mass spectrum (ESI$^+$): m/z=529 [M+H]$^+$

(35) 1-[2-(3-carboxy-phenyl)-2-oxo-ethyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product precipitated as the hydrochloride)

R$_f$ value: 0.54 (ready-made reversed phase TLC plate (E. Merck), acetonitrile/water/trifluoroacetic acid=50:50:1)

Mass spectrum (ESI$^+$): m/z=495 [M+H]$^+$

(36) 1-[2-(3-methoxycarbonyl-phenyl)-2-oxo-ethyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product precipitated as the hydrochloride)

R$_f$ value: 0.47 (ready-made reversed phase TLC plate (E. Merck), acetonitrile/water/trifluoroacetic acid=50:50:1)

Mass spectrum (ESI$^+$): m/z=509 [M+H]$^+$

(37) 1-{2-[3-(methylaminocarbonyl)-phenyl]-2-oxo-ethyl}-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

R$_f$ value: 0.53 (ready-made reversed phase TLC plate (E. Merck), acetonitrile/water/trifluoroacetic acid=50:50:1)

Mass spectrum (ESI$^+$): m/z=508 [M+H]$^+$

(38) 1-{2-[3-(dimethylaminocarbonyl)-phenyl]-2-oxo-ethyl}-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

R$_f$ value: 0.53 (ready-made reversed phase TLC plate (E. Merck), acetonitrile/water/trifluoroacetic acid=50:50:1)

Mass spectrum (ESI$^+$): m/z=522 [M+H]$^+$

(39) 1-{2-[3-(morpholin-4-yl-carbonyl)-phenyl]-2-oxo-ethyl}-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

R$_f$ value: 0.53 (ready-made reversed phase TLC plate (E. Merck), acetonitrile/water/trifluoroacetic acid=50:50:1)

Mass spectrum (ESI$^+$): m/z=564 [M+H]$^+$

(40) 1-[2-(2-carboxy-phenyl)-2-oxo-ethyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

R$_f$ value: 0.53 (ready-made reversed phase TLC plate (E. Merck), acetonitrile/water/trifluoroacetic acid=50:50:1)

Mass spectrum (ESI$^+$): m/z=495 [M+H]$^+$

(41) 1-[2-(2-ethoxycarbonyl-phenyl)-2-oxo-ethyl]-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

R$_f$ value: 0.41 (ready-made reversed phase TLC plate (E. Merck), acetonitrile/water/trifluoroacetic acid=50:50:1)

Mass spectrum (ESI$^+$): m/z=523 [M+H]$^+$

(42) 1-{2-[2-(dimethylaminocarbonyl)-phenyl]-2-oxo-ethyl}-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

R$_f$ value: 0.53 (ready-made reversed phase TLC plate (E. Merck), acetonitrile/water/trifluoroacetic acid=50:50:1)

Mass spectrum (ESI$^+$): m/z=522 [M+H]$^+$

(43) 1-{2-[2-(morpholin-4-yl-carbonyl)-phenyl]-2-oxo-ethyl}-3-methyl-7-(3-methyl-2-buten-1-yl)-8-(3-amino-piperidin-1-yl)-xanthine-hydrochloride (Carried out with 5-6 M isopropanolic hydrochloric acid in methylene chloride; product obtained as the hydrochloride)

(44) 1-[2-(2,6-dimethoxy-phenyl)-2-oxo-ethyl]-3-methyl-7-(3-methyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.44 (ready-made reversed phase TLC plate (E. Merck), acetonitrile/water/trifluoroacetic acid=50:50:1)
Mass spectrum (ESI$^+$): m/z=511 [M+H]$^+$

(45) 1-(2-phenyl-2-oxo-ethyl)-3-methyl-7-(2,3-dimethyl-2-buten-1-yl)-8-(3-amino-piperidin-1-yl)-xanthine-hydrochloride
(Carried out with 5-6 M isopropanolic hydrochloric acid in methylene chloride; product obtained as the hydrochloride)
$R_f$ value: 0.68 (ready-made reversed phase TLC plate (E. Merck), acetonitrile/water/trifluoroacetic acid=50:50:1)
Mass spectrum (ESI$^+$): m/z=465 [M+H]$^+$

(46) 1-((E)-3-phenyl-allyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.38 (silica gel, methylene chloride/methanol/conc. aqueous ammonia=95:5:0.1)
Mass spectrum (ESI$^+$): m/z=449 [M+H]$^+$

(47) 1-[benzo[b]thiophen-3-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.51 (silica gel, methylene chloride/methanol/conc. aqueous ammonia=90:10:1)
Mass spectrum (ESI$^+$): m/z=479 [M+H]$^+$

(48) 1-[(1H-indol-3-yl)methyl]-3-methyl-7-(3-methyl-2-buten-1-yl)-8-(3-amino-piperidin-1-yl)-xanthine
$R_f$ value: 0.48 (silica gel, methylene chloride/methanol/conc. aqueous ammonia=90:10:1)
Mass spectrum (ESI$^+$): m/z=462 [M+H]$^+$

(49) 1-[(biphenyl-4-yl)methyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.30 (silica gel, methylene chloride/methanol/conc. aqueous ammonia=95:5:0.1)
Mass spectrum (ESI$^+$): m/z=499 [M+H]$^+$

(50) 1-[(1-naphthyl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.56 (silica gel, methylene chloride/methanol/conc. aqueous ammonia=90:10:1)
Mass spectrum (ESI$^+$): m/z=457 [M+H]$^+$

(51) 1-[(1-methyl-2-oxo-1,2-dihydro-quinolin-4-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.40 (silica gel, methylene chloride/methanol/conc. aqueous ammonia=90:10:1)
Mass spectrum (ESI$^+$): m/z=488 [M+H]$^+$

(52) 1-[(quinolin-4-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.52 (silica gel, methylene chloride/methanol/conc. aqueous ammonia=90:10:1)
Mass spectrum (ESI$^+$): m/z=458 [M+H]$^+$

(53) 1-(2-cyclohexyl-2-oxo-ethyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.48 (silica gel, methylene chloride/methanol/conc. aqueous ammonia=90:10:1)
Mass spectrum (ESI$^+$): m/z=457 [M+H]$^+$

(54) 1-(3,3-dimethyl-2-oxo-butyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.49 (silica gel, methylene chloride/methanol/conc. aqueous ammonia=90:10:1)
Mass spectrum (ESI$^+$): m/z=431 [M+H]$^+$

(55) 1-[(quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.20 (silica gel, methylene chloride/methanol/conc. aqueous ammonia=95:5:0.1)
Mass spectrum (ESI$^+$): m/z=459 [M+H]$^+$

(56) 1-[(2-methyl-naphthalen-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.25 (silica gel, methylene chloride/methanol/conc. aqueous ammonia=95:5:0.1)
Mass spectrum (ESI$^+$): m/z=471 [M+H]$^+$

(57) 1-({5-[(methoxycarbonyl)methylamino]-isoquinolin-1-yl}methyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.43 (silica gel, methylene chloride/methanol/conc. aqueous ammonia=90:10:1)
Mass spectrum (ESI$^+$): m/z=561 [M+H]$^+$

(58) 1-(2-dimethylamino-2-oxo-ethyl)-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.38 (silica gel, methylene chloride/methanol/conc. aqueous ammonia=90:10:1)
Mass spectrum (ESI$^+$): m/z=418 [M+H]$^+$

(59) 1-[2-(piperidin-1-yl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.35 (silica gel, methylene chloride/methanol/conc. aqueous ammonia=90:10:1)
Mass spectrum (ESI$^+$): m/z=458 [M+H]$^+$

(60) 1-[(2-methyl-1-oxo-1,2-dihydro-isoquinoline-4-yl)methyl]-7-(2-butyn-1-yl)-8-(3-amino-piperidin-1-yl)-xanthine
(Carried out with 5-6 M isopropanolic hydrochloric acid in methylene chloride)
$R_f$ value: 0.17 (silica gel, methylene chloride/methanol/conc. aqueous ammonia=95:5:0.1)
Mass spectrum (ESI$^+$): m/z=488 [M+H]$^+$

(61) 1-[(2-methyl-1-oxo-1,2-dihydro-isoquinoline-4-yl)methyl]-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.13 (silica gel, methylene chloride/methanol/conc. aqueous ammonia=95:5:0.1)
Mass spectrum (ESI$^+$): m/z=504 [M+H]$^+$

(62) 1-[(2-methoxy-naphthalen-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.17 (silica gel, methylene chloride/methanol/conc. aqueous ammonia=95:5:0.1)
Mass spectrum (ESI$^+$): m/z=487 [M+H]$^+$

(63) 1-[(isoquinolin-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.42 (silica gel, methylene chloride/methanol/conc. aqueous ammonia=90:10:1)
Mass spectrum (ESI$^+$): m/z=458 [M+H]$^+$

(64) 1-[(4-methoxy-naphthalen-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.14 (silica gel, methylene chloride/methanol/conc. aqueous ammonia=95:5:0.1)
Mass spectrum (ESI$^+$): m/z=487 [M+H]$^+$

(65) 1-[(3-methyl-isoquinolin-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Melting point: 155-158° C.
Mass spectrum (ESI$^+$): m/z=472 [M+H]$^+$

(66) 1-[2-(2,3-dimethoxy-phenyl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.40 (silica gel, methylene chloride/methanol/conc. aqueous ammonia=90:10:1)
Mass spectrum (ESI$^+$): m/z=511 [M+H]$^+$

(67) 1-[(5-nitro-naphthalen-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.15 (silica gel, methylene chloride/methanol/conc. aqueous ammonia=95:5:0.1)
Mass spectrum (ESI$^+$): m/z=502 [M+H]$^+$

(68) 1-[2-(pyrrolidin-1-yl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.56 (silica gel, methylene chloride/methanol/conc. aqueous ammonia=90:10:1)
Mass spectrum (ESI$^+$): m/z=444 [M+H]$^+$

(69) 1-[(4-methyl-isoquinolin-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.46 (silica gel, methylene chloride/methanol/conc. aqueous ammonia=90:10:1)
Mass spectrum (ESI$^+$): m/z=472 [M+H]$^+$

(70) 1-[(2-naphthyl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.20 (silica gel, methylene chloride/methanol/conc. aqueous ammonia=95:5:0.1)
Mass spectrum (ESI$^+$): m/z=457 [M+H]$^+$

(71) 1-[(4-oxo-3,4-dihydro-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.38 (silica gel, methylene chloride/methanol/conc. aqueous ammonia=90:10:0.1)
Mass spectrum (ESI$^+$): m/z=475 [M+H]$^+$

(72) 1-[(quinolin-6-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.15 (silica gel, methylene chloride/methanol/conc. aqueous ammonia=95:5:0.1)
Mass spectrum (ESI$^+$): m/z=458 [M+H]$^+$

(73) 1-[(4-dimethylamino-naphthalen-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.18 (silica gel, methylene chloride/methanol/conc. aqueous ammonia=95:5:0.1)
Mass spectrum (ESI$^+$): m/z=500 [M+H]$^+$

(74) 1-[(isoquinolin-1-yl)methyl]-3-methyl-7-((E)-2-buten-1-yl)-8-(3-amino-piperidin-1-yl)-xanthine
(Carried out with 5-6 M isopropanolic hydrochloric acid in methylene chloride; the product still contains approx. 20% of Z isomer)
$R_f$ value: 0.66 (silica gel, methylene chloride/methanol/conc. aqueous ammonia=90:10:0.1)
Mass spectrum (ESI$^+$): m/z=460 [M+H]$^+$

(75) 1-[(3-methoxy-naphthalen-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.25 (silica gel, methylene chloride/methanol/conc. aqueous ammonia=95:5:0.1)
Mass spectrum (ESI$^+$): m/z=487 [M+H]$^+$

(76) 1-[2-(2,3-dihydro-benzo[1,4]dioxin-5-yl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
Mass spectrum (ESI$^+$): m/z=509 [M+H]$^+$

(77) 1-[(3-methyl-4-oxo-3,4-dihydro-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.20 (silica gel, methylene chloride/methanol/conc. aqueous ammonia=95:5:0.1)
Mass spectrum (ESI$^+$): m/z=489 [M+H]$^+$

(78) 1-[2-(3-methyl-2-oxo-2,3-dihydro-benzooxazol-7-yl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.47 (silica gel, methylene chloride/methanol/conc. aqueous ammonia=90:10:1)
Mass spectrum (ESI$^+$): m/z=522 [M+H]$^+$

(79) 1-[2-(benzo[1,3]dioxol-4-yl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
Mass spectrum (ESI$^+$): m/z=495 [M+H]$^+$

(80) 1-[(quinazolin-2-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)
Mass spectrum (ESI⁺): m/z=459 [M+H]⁺

(81) 1-[(quinazolin-2-yl)methyl]-3-methyl-7-(2-butyn-1-yl)-8-((S)-3-amino-piperidin-1-yl)-xanthine
(Carried out with 5-6 M isopropanolic hydrochloric acid in methylene chloride)
Mass spectrum (ESI⁺): m/z=459 [M+H]⁺

(82) 1-[(quinazolin-2-yl)methyl]-3-methyl-7-((E)-2-buten-1-yl)-8-((S)-3-amino-piperidin-1-yl)-xanthine
(Carried out with 5-6 M isopropanolic hydrochloric acid in methylene chloride; the product still contains approx. 20% of Z isomer)
$R_f$ value: 0.12 (silica gel, methylene chloride/methanol/conc. aqueous ammonia=95:5:0.1)
Mass spectrum (ESI⁺): m/z=461 [M+H]⁺

(83) 1-[(quinazolin-2-yl)methyl]-3-methyl-7-((E)-2-buten-1-yl)-8-((R)-3-amino-piperidin-1-yl)-xanthine
(Carried out with 5-6 M isopropanolic hydrochloric acid in methylene chloride; the product still contains approx. 15% of Z isomer)
$R_f$ value: 0.12 (silica gel, methylene chloride/methanol/conc. aqueous ammonia=95:5:0.1)
Mass spectrum (ESI⁺): m/z=461 [M+H]⁺

(84) 1-[(3-methyl-isoquinolin-1-yl)methyl]-3-methyl-7-((E)-2-buten-1-yl)-8-((R)-3-amino-piperidin-1-yl)-xanthine
(Carried out with 5-6 M isopropanolic hydrochloric acid in methylene chloride; the product still contains approx. 17% of Z isomer)
$R_f$ value: 0.54 (silica gel, methylene chloride/methanol/conc. aqueous ammonia=90:10:1)
Mass spectrum (ESI⁺): m/z=474 [M+H]⁺

(85) 1-[(3-methyl-isoquinolin-1-yl)methyl]-3-methyl-7-((E)-2-buten-1-yl)-8-((S)-3-amino-piperidin-1-yl)-xanthine
(Carried out with 5-6 M isopropanolic hydrochloric acid in methylene chloride; the product still contains approx. 17% of Z isomer)
$R_f$ value: 0.54 (silica gel, methylene chloride/methanol/conc. aqueous ammonia=90:10:1)
Mass spectrum (ESI⁺): m/z=474 [M+H]⁺

(86) 1-(2-{2-[(ethylaminocarbonyl)methoxy]-phenyl}-2-oxo-ethyl)-3-methyl-7-(2-butyn-1-yl)-8-((R)-3-amino-piperidin-1-yl)-xanthine
Mass spectrum (ESI⁺): m/z=536 [M+H]⁺

(87) 1-[2-(2-amino-phenyl)-2-oxo-ethyl]-3-methyl-7-[(1-cyclopenten-1-yl)methyl]-8-(3-amino-piperidin-1-yl)-xanthine
Mass spectrum (ESI⁺): m/z=478 [M+H]⁺

(88) 1-(2-phenyl-2-oxo-ethyl)-3-methyl-7-[(1-cyclopenten-1-yl)methyl]-8-(3-amino-piperidin-1-yl)-xanthine
Mass spectrum (ESI⁺): m/z=463 [M+H]⁺

(89) 1-(2-{2-[(methylaminocarbonyl)methoxy]-phenyl}-2-oxo-ethyl)-3-methyl-7-[(1-cyclopenten-1-yl)methyl]-8-(3-amino-piperidin-1-yl)-xanthine
Mass spectrum (ESI⁺): m/z=550 [M+H]⁺

(90) 1-methyl-3-isopropyl-7-(2-cyano-benzyl)-8-(3-amino-piperidin-1-yl)-xanthine
$R_f$ value: 0.40 (silica gel, methylene chloride/methanol=9:1)
Mass spectrum (ESI⁺): m/z=422 [M+H]⁺

(91) 1-(2-{2-[(methylaminocarbonyl)methoxy]-phenyl}-2-oxo-ethyl)-3-methyl-7-(2-butyn-1-yl)-8-(3-amino-piperidin-1-yl)-xanthine
Mass spectrum (ESI⁺): m/z=522 [M+H]⁺

(92) 1-(2-{2-[(aminocarbonyl)methoxy]-phenyl}-2-oxo-ethyl)-3-methyl-7-(2-butyn-1-yl)-8-(3-amino-piperidin-1-yl)-xanthine
Mass spectrum (ESI⁺): m/z=508 [M+H]⁺

(93) 1-[2-(2-cyanomethylamino-phenyl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.50 (ready-made reversed phase TLC plate (E. Merck), acetonitrile/water/trifluoroacetic acid=50:50:1)
Mass spectrum (ESI⁺): m/z=505 [M+H]⁺

(94) 1-(2-{2-[(isopropylaminocarbonyl)methoxy]-phenyl}-2-oxo-ethyl)-3-methyl-7-(2-butyn-1-yl)-8-(3-amino-piperidin-1-yl)-xanthine
$R_f$ value: 0.30 (silica gel, methylene chloride/methanol=9:1)
Mass spectrum (ESI⁺): m/z=550 [M+H]⁺

(95) 1-[(isoquinolin-1-yl)methyl]-3-[(methoxycarbonyl)methyl]-7-(3-methyl-2-buten-1-yl)-8-(3-amino-piperidin-1-yl)-xanthine
$R_f$ value: 0.21 (silica gel, methylene chloride/methanol/conc. aqueous ammonia=90:10:1)
Mass spectrum (ESI⁺): m/z=532 [M+H]⁺

(96) 1-[2-(2-acetylamino-phenyl)-2-oxo-ethyl]-3-methyl-7-((E)-2-buten-1-yl)-8-(3-amino-piperidin-1-yl)-xanthine
(product contains approx. 10% of Z isomer)
Mass spectrum (ESI⁺): m/z=494 [M+H]⁺

(97) 1-(2-phenyl-2-oxo-ethyl)-3-methyl-7-((E)-2-buten-1-yl)-8-(3-amino-piperidin-1-yl)-xanthine
(product contains approx. 25% of Z isomer)
$R_f$ value: 0.30 (silica gel, methylene chloride/methanol=9:1)
Mass spectrum (ESI⁺): m/z=437 [M+H]⁺

(98) 1-(2-{2-[(isopropyloxycarbonyl)methoxy]-phenyl}-2-oxo-ethyl)-3-methyl-7-(3-methyl-2-buten-1-yl)-8-(3-amino-piperidin-1-yl)-xanthine
Mass spectrum (ESI⁺): m/z=567 [M+H]⁺

(99) 1-(2-{2-[(methylaminocarbonyl)methoxy]-phenyl}-2-oxo-ethyl)-3-methyl-7-(2-butyn-1-yl)-8-((R)-3-amino-piperidin-1-yl)-xanthine
Mass spectrum (ESI⁺): m/z=522 [M+H]⁺

(100) 1-(2-{2-[(isopropylcarbonyl)amino]-phenyl}-2-oxo-ethyl)-3-methyl-7-((E)-2-buten-1-yl)-8-(3-amino-piperidin-1-yl)-xanthine
(product contains approx. 10% of Z isomer)
Mass spectrum (ESI⁺): m/z=522 [M+H]⁺

(101) 1-(2-{2-[(methylaminocarbonyl)methoxy]-phenyl}-2-oxo-ethyl)-3-methyl-7-((E)-2-buten-1-yl)-8-(3-amino-piperidin-1-yl)-xanthine
(product contains approx. 8% of Z isomer)
$R_f$ value: 0.51 (ready-made reversed phase TLC plate (E. Merck), acetonitrile/water/trifluoroacetic acid=50:50:0.1)
Mass spectrum (ESI⁺): m/z=524 [M+H]⁺

(102) 1-(2-{2-[(ethylaminocarbonyl)methoxy]-phenyl}-2-oxo-ethyl)-3-methyl-7-(2-butyn-1-yl)-8-((S)-3-amino-piperidin-1-yl)-xanthine
Mass spectrum (ESI⁺): m/z=536 [M+H]⁺

(103) 1-[2-(2-{[(ethoxycarbonylamino)carbonyl]amino}-phenyl)-2-oxo-ethyl]-3-methyl-7-(3-methyl-2-buten-1-yl)-8-(3-amino-piperidin-1-yl)-xanthine
Mass spectrum (ESI⁺): m/z=581 [M+H]⁺

(104) 1-[2-(2-amino-phenyl)-2-oxo-ethyl]-3-methyl-7-((E)-2-buten-1-yl)-8-(3-amino-piperidin-1-yl)-xanthine
$R_f$ value: 0.54 (ready-made reversed phase TLC plate (E. Merck), acetonitrile/water/trifluoroacetic acid=50:50:0.1)
Mass spectrum (ESI⁺): m/z=452 [M+H]⁺

(105) 1-[2-(2-acetylamino-phenyl)-2-oxo-ethyl]-3-methyl-7-(3-methyl-2-buten-1-yl)-8-((S)-3-amino-piperidin-1-yl)-xanthine
$R_f$ value: 0.48 (ready-made reversed phase TLC plate (E. Merck), acetonitrile/water/trifluoroacetic acid=50:50:0.1)
Mass spectrum (ESI$^+$): m/z=508 [M+H]$^+$ (106) 1-[2-(2-amino-phenyl)-2-oxo-ethyl]-3-methyl-7-(2-butyn-1-yl)-8-(3-amino-piperidin-1-yl)-xanthine
$R_f$ value: 0.31 (silica gel, methylene chloride/methanol/conc. aqueous ammonia=90:10:1)
Mass spectrum (ESI$^+$): m/z=450 [M+H]$^+$ (107) 1-(2-{2-[(methylaminocarbonyl)methoxy]-phenyl}-2-oxo-ethyl)-3-methyl-7-(2-butyn-1-yl)-8-((S)-3-amino-piperidin-1-yl)-xanthine
Mass spectrum (ESI$^+$): m/z=522 [M+H]$^+$ (108) 1-(2-phenyl-2-oxo-ethyl)-3-methyl-7-((E)-2-buten-1-yl)-8-((R)-3-amino-piperidin-1-yl)-xanthine
(product contains approx. 22% of Z isomer)
Mass spectrum (ESI$^+$): m/z=437 [M+H]$^+$ (109) 1-(2-{2-[(ethylaminocarbonyl)methoxy]-phenyl}-2-oxo-ethyl)-3-methyl-7-(2-butyn-1-yl)-8-(3-amino-piperidin-1-yl)-xanthine
$R_f$ value: 0.40 (silica gel, methylene chloride/methanol=9:1)
Mass spectrum (ESI$^+$): m/z=536 [M+H]$^+$ (110) 1-[2-(2-acetylamino-phenyl)-2-oxo-ethyl]-3-methyl-7-(2-butyn-1-yl)-8-(3-amino-piperidin-1-yl)-xanthine
$R_f$ value: 0.23 (silica gel, methylene chloride/methanol/conc. aqueous ammonia=90:10:1)
Mass spectrum (ESI$^+$): m/z=492 [M+H]$^+$ (111) 1-(2-{2-[2-oxo-2-(pyrrolidin-1-yl)-ethoxy]-phenyl}-2-oxo-ethyl)-3-methyl-7-(2-butyn-1-yl)-8-(3-amino-piperidin-1-yl)-xanthine
$R_f$ value: 0.20 (silica gel, methylene chloride/methanol=9:1)
Mass spectrum (ESI$^+$): m/z=562 [M+H]$^+$ (112) 1-(2-{2-[(methylaminocarbonyl)methoxy]-phenyl}-2-oxo-ethyl)-3-methyl-7-(3-methyl-2-buten-1-yl)-8-((S)-3-amino-piperidin-1-yl)-xanthine
Mass spectrum (ESI$^+$): m/z=538 [M+H]$^+$ (113) 1-(2-phenyl-2-oxo-ethyl)-3-methyl-7-(2-butyn-1-yl)-8-((R)-3-amino-piperidin-1-yl)-xanthine
Mass spectrum (ESI$^+$): m/z=435 [M+H]$^+$ (114) 1-(2-{2-[(ethylaminocarbonyl)methoxy]-phenyl}-2-oxo-ethyl)-3-methyl-7-((E)-2-buten-1-yl)-8-((R)-3-amino-piperidin-1-yl)-xanthine
(product contains approx. 30% of Z isomer)
Mass spectrum (ESI$^+$): m/z=538 [M+H]$^+$ (115) 1-methyl-7-(2-cyano-benzyl)-8-(3-amino-piperidin-1-yl)-xanthine
Mass spectrum (ESI$^+$): m/z=380 [M+H]$^+$ (116) 1-(2-{2-[(isopropylcarbonyl)amino]-phenyl}-2-oxo-ethyl)-3-methyl-7-(3-methyl-2-buten-1-yl)-8-(3-amino-piperidin-1-yl)-xanthine
$R_f$ value: 0.40 (ready-made reversed phase TLC plate (E. Merck), acetonitrile/water/trifluoroacetic acid=50:50:0.1)
Mass spectrum (ESI$^+$): m/z=536 [M+H]$^+$ (117) 1-(2-phenyl-2-oxo-ethyl)-3-methyl-7-((E)-2-buten-1-yl)-8-((S)-3-amino-piperidin-1-yl)-xanthine
(product contains approx. 23% of Z isomer)
$R_f$ value: 0.42 (ready-made reversed phase TLC plate (E. Merck), acetonitrile/water/trifluoroacetic acid=50:50:0.1)
Mass spectrum (ESI$^+$): m/z=437 [M+H]$^+$ (118) 1-(2-{2-[(isopropylcarbonyl)amino]-phenyl}-2-oxo-ethyl)-3-methyl-7-(2-butyn-1-yl)-8-(3-amino-piperidin-1-yl)-xanthine
$R_f$ value: 0.20 (silica gel, methylene chloride/methanol/conc. aqueous ammonia=90:10:1)
Mass spectrum (ESI$^+$): m/z=520 [M+H]$^+$ (119) 1-[2-(2-acetylamino-phenyl)-2-oxo-ethyl]-3-methyl-7-(2-butyn-1-yl)-8-((S)-3-amino-piperidin-1-yl)-xanthine
$R_f$ value: 0.15 (silica gel, methylene chloride/methanol/conc. aqueous ammonia=90:10:1)
Mass spectrum (ESI$^+$): m/z=492 [M+H]$^+$ (120) 1-(2-{2-[(isopropylcarbonyl)amino]-phenyl}-2-oxo-ethyl)-3-methyl-7-(2-butyn-1-yl)-8-((S)-3-amino-piperidin-1-yl)-xanthine
Mass spectrum (ESI$^+$): m/z=520 [M+H]$^+$ (121) 1-(2-phenyl-2-oxo-ethyl)-3-methyl-7-(2-methyl-allyl)-8-(3-amino-piperidin-1-yl)-xanthine
$R_f$ value: 0.21 (silica gel, methylene chloride/methanol/conc. aqueous ammonia=90:10:1)
Mass spectrum (ESI$^+$): m/z=437 [M+H]$^+$ (122) 1-(2-phenyl-2-oxo-ethyl)-3-methyl-7-(3-bromo-allyl)-8-(3-amino-piperidin-1-yl)-xanthine
$R_f$ value: 0.14 (silica gel, methylene chloride/methanol/conc. aqueous ammonia=90:10:1)
Mass spectrum (ESI$^+$): m/z=501, 503 [M+H]$^+$ (123) 1-(2-{2-[(methoxycarbonyl)amino]-phenyl}-2-oxo-ethyl)-3-methyl-7-(3-methyl-2-buten-1-yl)-8-(3-amino-piperidin-1-yl)-xanthine
$R_f$ value: 0.42 (ready-made reversed phase TLC plate (E. Merck), acetonitrile/water/trifluoroacetic acid=50:50:0.1)
Mass spectrum (ESI$^+$): m/z=524 [M+H]$^+$ (124) 1-(2-phenyl-2-oxo-ethyl)-3-methyl-7-[(furan-2-yl)methyl]-8-(3-amino-piperidin-1-yl)-xanthine
$R_f$ value: 0.23 (silica gel, methylene chloride/methanol/conc. aqueous ammonia=90:10:1)
Mass spectrum (ESI$^+$): m/z=463 [M+H]$^+$ (125) 1-(2-phenyl-2-oxo-ethyl)-3-methyl-7-(2-chloro-allyl)-8-(3-amino-piperidin-1-yl)-xanthine
$R_f$ value: 0.18 (silica gel, methylene chloride/methanol/conc. aqueous ammonia=90:10:1)

(126) 1-{2-[2-(1-methoxycarbonyl-ethoxy)-phenyl]-2-oxo-ethyl}-3-methyl-7-(2-butyn-1-yl)-8-(3-amino-piperidin-1-yl)-xanthine
Mass spectrum (ESI$^+$): m/z=537 [M+H]$^+$ (127) 1-{2-[2-(1-aminocarbonyl-ethoxy)-phenyl]-2-oxo-ethyl}-3-methyl-7-(2-butyn-1-yl)-8-(3-amino-piperidin-1-yl)-xanthine
Mass spectrum (ESI$^+$): m/z=522 [M+H]$^+$ (128) 1-(2-phenyl-2-oxo-ethyl)-3-methyl-7-(2-butyn-1-yl)-8-((S)-3-amino-piperidin-1-yl)-xanthine
Mass spectrum (ESI$^+$): m/z=435 [M+H]$^+$ (129) 1-[(3-methyl-isoquinolin-1-yl)methyl]-3-methyl-7-(2-butyn-1-yl)-8-((S)-3-amino-piperidin-1-yl)-xanthine
(Carried out with 5-6 M isopropanolic hydrochloric acid in methylene chloride)
Melting point: 155-156.5° C.
Mass spectrum (ESI$^+$): m/z=472 [M+H]$^+$ (130) 1-[(3-methyl-isoquinolin-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.52 (silica gel, methylene chloride/methanol/conc. aqueous ammonia=90:10:1)
Mass spectrum (ESI$^+$): m/z=472 [M+H]$^+$ (131) 1-[(4-methyl-isoquinolin-1-yl)methyl]-3-methyl-7-(2-butyn-1-yl)-8-((S)-3-amino-piperidin-1-yl)-xanthine
(Carried out with 5-6 M isopropanolic hydrochloric acid in methylene chloride)

R$_f$ value: 0.46 (silica gel, methylene chloride/methanol/conc. aqueous ammonia=90:10:1)
Mass spectrum (ESI$^+$): m/z=472 [M+H]$^+$
(132) 1-[(4-methyl-isoquinolin-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.46 (silica gel, methylene chloride/methanol/conc. aqueous ammonia=90:10:1)
Mass spectrum (ESI$^+$): m/z=472 [M+H]$^+$
(133) 1-[(4-methyl-isoquinolin-1-yl)methyl]-3-methyl-7-((E)-2-buten-1-yl)-8-((S)-3-amino-piperidin-1-yl)-xanthine
(Carried out with 5-6 M isopropanolic hydrochloric acid in methylene chloride)
R$_f$ value: 0.48 (silica gel, methylene chloride/methanol/conc. aqueous ammonia=90:10:1)
Mass spectrum (ESI$^+$): m/z=474 [M+H]$^+$
(134) 1-[(4-methyl-isoquinolin-1-yl)methyl]-3-methyl-7-((E)-2-buten-1-yl)-8-((R)-3-amino-piperidin-1-yl)-xanthine
(Carried out with 5-6 M isopropanolic hydrochloric acid in methylene chloride)
Melting point: 167.5-172° C.
Mass spectrum (ESI$^+$): m/z=474 [M+H]$^+$
(135) 1-[2-(2,3-dihydro-benzo[1,4]dioxin-5-yl)-2-oxo-ethyl]-3-methyl-7-(2-butyn-1-yl)-8-(3-(R)-amino-piperidin-1-yl)-xanthine
(Carried out with 5-6 M isopropanolic hydrochloric acid in methylene chloride)
R$_f$ value: 0.34 (silica gel, methylene chloride/methanol/conc. aqueous ammonia=90:10:1)
Mass spectrum (ESI$^+$): m/z=493 [M+H]$^+$
(136) 1-[2-(2,3-dihydro-benzo[1,4]dioxin-5-yl)-2-oxo-ethyl]-3-methyl-7-(2-butyn-1-yl)-8-(3-(S)-amino-piperidin-1-yl)-xanthine
(Carried out with 5-6 M isopropanolic hydrochloric acid in methylene chloride)
Mass spectrum (ESI$^+$): m/z=493 [M+H]$^+$
(137) 1-[(4-methoxy-naphthalen-1-yl)methyl]-3-methyl-7-(2-butyn-1-yl)-8-((S)-3-amino-piperidin-1-yl)-xanthine
(Carried out with 5-6 M isopropanolic hydrochloric acid in methylene chloride)
R$_f$ value: 0.52 (silica gel, methylene chloride/methanol/conc. aqueous ammonia=90:10:1)
Mass spectrum (ESI$^+$): m/z=487 [M+H]$^+$
(138) 1-[(4-methoxy-naphthalen-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.52 (silica gel, methylene chloride/methanol/conc. aqueous ammonia=90:10:1)
Mass spectrum (ESI$^+$): m/z=487 [M+H]$^+$
(139) 1-[2-(benzo[1,3]dioxol-4-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.41 (silica gel, methylene chloride/methanol/conc. aqueous ammonia=90:10:1)
Mass spectrum (ESI$^+$): m/z=479 [M+H]$^+$
(140) 1-[2-(benzo[1,3]dioxol-4-yl)-2-oxo-ethyl]-3-methyl-7-(2-butyn-1-yl)-8-((S)-3-amino-piperidin-1-yl)-xanthine
(Carried out with 5-6 M isopropanolic hydrochloric acid in methylene chloride)
Mass spectrum (ESI$^+$): m/z=479 [M+H]$^+$
(141) 1-[(4-methyl-quinazolin-2-yl)methyl]-3-methyl-7-(2-butyn-1-yl)-8-(3-(S)-amino-piperidin-1-yl)-xanthine
(Carried out with 5-6 M isopropanolic hydrochloric acid in methylene chloride)
R$_f$ value: 0.51 (silica gel, methylene chloride/methanol/conc. aqueous ammonia=90:10:1)
Mass spectrum (ESI$^+$): m/z=473 [M+H]$^+$
(142) 1-[(4-methyl-quinazolin-2-yl)methyl]-3-methyl-7-(2-butyn-1-yl)-8-(3-(R)-amino-piperidin-1-yl)-xanthine
(Carried out with 5-6 M isopropanolic hydrochloric acid in methylene chloride)
Melting point: 198-202° C.
Mass spectrum (ESI$^+$): m/z=473 [M+H]$^+$
(143) 1-[2-(3-methyl-2-oxo-2,3-dihydro-benzooxazol-4-yl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
R$_f$ value: 0.53 (silica gel, methylene chloride/methanol/conc. aqueous ammonia=90:10:1)
Mass spectrum (ESI$^+$): m/z=522 [M+H]$^+$
(144) 1-(2-{2-[(ethylaminocarbonyl)methoxy]-phenyl}-2-oxo-ethyl)-3-methyl-7-((E)-2-buten-1-yl)-8-((S)-3-amino-piperidin-1-yl)-xanthine
Mass spectrum (ESI$^+$): m/z=538 [M+H]$^+$
(145) 1-(2-{2-[(isopropylcarbonyl)amino]-phenyl}-2-oxo-ethyl)-3-methyl-7-((E)-2-buten-1-yl)-8-((S)-3-amino-piperidin-1-yl)-xanthine
R$_f$ value: 0.49 (ready-made reversed phase TLC plate (E. Merck), acetonitrile/water/trifluoroacetic acid=50:50:0.1)
Mass spectrum (ESI$^+$): m/z=522 [M+H]$^+$
(146) 1-(2-{2-[(ethylcarbonyl)amino]-phenyl}-2-oxo-ethyl)-3-methyl-7-((E)-2-buten-1-yl)-8-((R)-3-amino-piperidin-1-yl)-xanthine
Mass spectrum (ESI$^+$): m/z=508 [M+H]$^+$
(147) 1-[2-(2-acetylamino-phenyl)-2-oxo-ethyl]-3-methyl-7-((E)-2-buten-1-yl)-8-((R)-3-amino-piperidin-1-yl)-xanthine
Mass spectrum (ESI$^+$): m/z=494 [M+H]$^+$
(148) 1-(2-{2-[(methylaminocarbonyl)methoxy]-phenyl}-2-oxo-ethyl)-3-methyl-7-((E)-2-buten-1-yl)-8-((R)-3-amino-piperidin-1-yl)-xanthine
Mass spectrum (ESI$^+$): m/z=524 [M+H]$^+$
(149) 1-[2-(2-acetylamino-phenyl)-2-oxo-ethyl]-3-methyl-7-((E)-2-buten-1-yl)-8-((S)-3-amino-piperidin-1-yl)-xanthine
R$_f$ value: 0.49 (ready-made reversed phase TLC plate (E. Merck), acetonitrile/water/trifluoroacetic acid=50:50:0.1)
Mass spectrum (ESI$^+$): m/z=494 [M+H]$^+$
(150) 1-(2-{2-[(methylaminocarbonyl)methoxy]-phenyl}-2-oxo-ethyl)-3-methyl-7-((E)-2-buten-1-yl)-8-((S)-3-amino-piperidin-1-yl)-xanthine
Mass spectrum (ESI$^+$): m/z=524 [M+H]$^+$
(151) 1-(2-{2-[(isopropylcarbonyl)amino]-phenyl}-2-oxo-ethyl)-3-methyl-7-(2-butyn-1-yl)-8-((R)-3-amino-piperidin-1-yl)-xanthine
Mass spectrum (ESI$^+$): m/z=520 [M+H]$^+$
(152) 1-(2-{2-[(isopropylcarbonyl)amino]-phenyl}-2-oxo-ethyl)-3-methyl-7-((E)-2-buten-1-yl)-8-((R)-3-amino-piperidin-1-yl)-xanthine
Mass spectrum (ESI$^+$): m/z=522 [M+H]$^+$
(153) 1-(2-{2-[2-(morpholin-4-yl)-2-oxo-ethoxy]-phenyl}-2-oxo-ethyl)-3-methyl-7-(2-butyn-1-yl)-8-(3-amino-piperidin-1-yl)-xanthine
Mass spectrum (ESI$^+$): m/z=578 [M+H]$^+$ (154) 1-(2-{2-[(ethylcarbonyl)amino]-phenyl}-2-oxo-ethyl)-3-methyl-7-((E)-2-buten-1-yl)-8-((S)-3-amino-piperidin-1-yl)-xanthine
$R_f$ value: 0.50 (ready-made reversed phase TLC plate (E. Merck), acetonitrile/water/trifluoroacetic acid=50:50:0.1)
Mass spectrum (ESI$^+$): m/z=508 [M+H]$^+$ (155) 1-(2-{2-[(ethylcarbonyl)amino]-phenyl}-2-oxo-ethyl)-3-methyl-7-(2-butyn-1-yl)-8-((R)-3-amino-piperidin-1-yl)-xanthine
Mass spectrum (ESI$^+$): m/z=506 [M+H]$^+$ (156) 1-(2-{2-[(ethylcarbonyl)amino]-phenyl}-2-oxo-ethyl)-3-methyl-7-(2-butyn-1-yl)-8-((S)-3-amino-piperidin-1-yl)-xanthine
$R_f$ value: 0.20 (silica gel, methylene chloride/methanol/conc. aqueous ammonia=90:10:1)
Mass spectrum (ESI$^+$): m/z=506 [M+H]$^+$ (157) 1-[2-(2-acetylamino-phenyl)-2-oxo-ethyl]-3-methyl-7-(2-butyn-1-yl)-8-((R)-3-amino-piperidin-1-yl)-xanthine
Mass spectrum (ESI$^+$): m/z=492 [M+H]$^+$ (158) 1-[2-(2-nitro-3-methoxy-phenyl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.49 (silica gel, methylene chloride/methanol/conc. aqueous ammonia=90:10:1)
Mass spectrum (ESI$^+$): m/z=526 [M+H]$^+$ (159) 1-(2-{2-[(phenylcarbonyl)amino]-phenyl}-2-oxo-ethyl)-3-methyl-7-((E)-2-buten-1-yl)-8-(3-amino-piperidin-1-yl)-xanthine
$R_f$ value: 0.49 (ready-made reversed phase TLC plate (E. Merck), acetonitrile/water/trifluoroacetic acid=50:50:0.1)
Mass spectrum (ESI$^+$): m/z=556 [M+H]$^+$ (160) 1-[(2-acetyl-benzofuran-3-yl)methyl]-3-methyl-7-(2-butyn-1-yl)-8-(3-amino-piperidin-1-yl)-xanthine
(Obtained as main product when 1-{2-[2-(2-oxo-propoxy)-phenyl]-2-oxo-ethyl}-3-methyl-7-(2-butyn-1-yl)-8-[3-(tert.-butyloxycarbonylamino)-piperidin-1-yl]-xanthine is treated with trifluoroacetic acid in methylene chloride)
Mass spectrum (ESI$^+$): m/z=489 [M+H]$^+$ (161) 1-{2-[2-(1-ethoxycarbonyl-1-methyl-ethoxy)-phenyl]-2-oxo-ethyl}-3-methyl-7-(2-butyn-1-yl)-8-(3-amino-piperidin-1-yl)-xanthine
Mass spectrum (ESI$^+$): m/z=565 [M+H]$^+$ (162) 1-[2-(2-amino-3-methoxy-phenyl)-2-oxo-ethyl]-3-methyl-7-(3-methyl-2-buten-1-yl)-8-(3-amino-piperidin-1-yl)-xanthine
(Carried out with 5-6 M isopropanolic hydrochloric acid in methylene chloride)
$R_f$ value: 0.38 (silica gel, methylene chloride/methanol/conc. aqueous ammonia=90:10:1)
Mass spectrum (ESI$^+$): m/z=496 [M+H]$^+$ (163) 1-[(4-dimethylamino-quinazolin-2-yl)methyl]-3-methyl-7-(2-butyn-1-yl)-8-(3-amino-piperidin-1-yl)-xanthine
$R_f$ value: 0.30 (silica gel, methylene chloride/methanol/conc. aqueous ammonia=90:10:0.1)
Mass spectrum (ESI$^+$): m/z=502 [M+H]$^+$ (164) 1-[2-(2-oxo-2,3-dihydro-benzooxazol-7-yl)-2-oxo-ethyl]-3-methyl-7-(3-methyl-2-buten-1-yl)-8-(3-amino-piperidin-1-yl)-xanthine
$R_f$ value: 0.42 (silica gel, methylene chloride/methanol/conc. aqueous ammonia=90:10:1)
Mass spectrum (ESI$^+$): m/z=508 [M+H]$^+$ (165) 1-(2-{2-[(ethoxycarbonyl)methylamino]-phenyl}-2-oxo-ethyl)-3-methyl-7-((E)-2-buten-1-yl)-8-((R)-3-amino-piperidin-1-yl)-xanthine
$R_f$ value: 0.51 (ready-made reversed phase TLC plate (E. Merck), acetonitrile/water/trifluoroacetic acid=50:50:0.1)
Mass spectrum (ESI$^+$): m/z=538 [M+H]$^+$ (166) 1-(2-phenyl-2-oxo-ethyl)-3-methyl-7-((Z)-2-methyl-2-buten-1-yl)-8-(3-amino-piperidin-1-yl)-xanthine
$R_f$ value: 0.29 (silica gel, methylene chloride/methanol/conc. aqueous ammonia=90:10:1)
Mass spectrum (ESI$^+$): m/z=451 [M+H]$^+$ (167) 1-(2-phenyl-2-oxo-ethyl)-3-methyl-7-((E)-2-methyl-2-buten-1-yl)-8-(3-amino-piperidin-1-yl)-xanthine
$R_f$ value: 0.59 (silica gel, methylene chloride/methanol/conc. aqueous ammonia=80:20:1)
Mass spectrum (ESI$^+$): m/z=451 [M+H]$^+$ (168) 1-[(imidazo[1,2-a]pyridin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.47 (silica gel, methylene chloride/methanol/conc. aqueous ammonia=90:10:1)
Mass spectrum (ESI$^+$): m/z=447 [M+H]$^+$ (169) 1-[(quinoxalin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.50 (silica gel, methylene chloride/methanol/conc. aqueous ammonia=90:10:1)
Mass spectrum (ESI$^+$): m/z=459 [M+H]$^+$ (170) 1-[2-(1,3-dimethyl-2-oxo-2,3-dihydro-1H-benzoimidazol-4-yl)-2-oxo-ethyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.55 (silica gel, methylene chloride/methanol/conc. aqueous ammonia=90:10:1)
Mass spectrum (ESI$^+$): m/z=519 [M+H]$^+$ (171) 1-[(quinoxalin-6-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Mass spectrum (ESI$^+$): m/z=459 [M+H]$^+$ (172) 1-[(2-cyano-benzofuran-3-yl)methyl]-3-methyl-7-(2-butyn-1-yl)-8-(3-amino-piperidin-1-yl)-xanthine
Mass spectrum (ESI$^+$): m/z=472 [M+H]$^+$ (173) 1-[2-(2-oxo-2,3-dihydro-benzooxazol-4-yl)-2-oxo-ethyl]-3-methyl-7-(2-butyn-1-yl)-8-(3-amino-piperidin-1-yl)-xanthine
Mass spectrum (ESI$^+$): m/z=492 [M+H]$^+$
$R_f$ value: 0.47 (silica gel, methylene chloride/methanol/conc. aqueous ammonia=90:10:1)

(174) 1-[(3-methyl-quinoxalin-2-yl)methyl]-3-methyl-7-(2-butyn-1-yl)-8-(3-amino-piperidin-1-yl)-xanthine
Melting point: 188.5-191° C.
Mass spectrum (ESI$^+$): m/z=473 [M+H]$^+$ (175) 1-[(3-phenyl-isoquinolin-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.45 (ready-made reversed phase TLC plate (E. Merck), acetonitrile/water/trifluoroacetic acid=50:50:1)
Mass spectrum (ESI$^+$): m/z=534 [M+H]$^+$ (176) 1-(2-{2-[(methanesulphinyl)methoxy]-phenyl}-2-oxo-ethyl)-3-methyl-7-(2-butyn-1-yl)-8-(3-amino-piperidin-1-yl)-xanthine×trifluoroacetic acid
Mass spectrum (ESI$^+$): m/z=527 [M+H]$^+$ (177) 1-[(benzofuran-3-yl)methyl]-3-methyl-7-(2-butyn-1-yl)-8-(3-amino-piperidin-1-yl)-xanthine (Produced when 1-{[2-(tert.-butylcarbonyl)-benzofuran-3-yl]methyl}-3-methyl-7-(2-butyn-1-yl)-8-[3-(tert.-butyloxycarbonylamino)-piperidin-1-yl]-xanthine is treated with trifluoroacetic acid in methylene chloride)

Mass spectrum (ESI$^+$): m/z=447 [M+H]$^+$ (178) 1-[(3,4-dimethyl-isoquinolin-1-yl)methyl]-3-methyl-7-(2-butyn-1-yl)-8-(3-amino-piperidin-1-yl)-xanthine-hydrochloride (Carried out with 5-6 M isopropanolic hydrochloric acid in methylene chloride)

R$_f$ value: 0.75 (aluminium oxide, methylene chloride/methanol=10:1)

Mass spectrum (ESI$^+$): m/z=486 [M+H]$^+$ (179) 1-[(benzofuran-2-yl)methyl]-3-methyl-7-(2-butyn-1-yl)-8-((R)-3-amino-piperidin-1-yl)-xanthine Mass spectrum (ESI$^+$): m/z=447 [M+H]$^+$ (180) 1-{[4-(morpholin-4-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.45 (silica gel, methylene chloride/methanol/conc. aqueous ammonia=90:10:0.1)

Mass spectrum (ESI$^+$): m/z=544 [M+H]$^+$ (181) 1-{[4-(piperidin-1-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.55 (silica gel, methylene chloride/methanol/conc. aqueous ammonia=90:10:0.1)

Mass spectrum (ESI$^+$): m/z=542 [M+H]$^+$ (182) 1-{[4-(piperazin-1-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.23 (silica gel, methylene chloride/methanol/conc. aqueous ammonia=90:10:0.1)

Mass spectrum (ESI$^+$): m/z=543 [M+H]$^+$ (183) 1-{[4-(pyrrolidin-1-yl)-quinazolin-2-yl]methyl}-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.50 (silica gel, methylene chloride/methanol/conc. aqueous ammonia=90:10:0.1)

Mass spectrum (ESI$^+$): m/z=528 [M+H]$^+$ (184) 1-[2-(3-methyl-2-oxo-2,3-dihydro-1H-benzoimidazol-4-yl)-2-oxo-ethyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.43 (silica gel, methylene chloride/methanol/conc. aqueous ammonia=90:10:1)

Mass spectrum (ESI$^+$): m/z=505 [M+H]$^+$ (185) 1-[(4-cyano-naphthalen-1-yl)methyl]-3-methyl-7-(2-butyn-1-yl)-8-((R)-3-amino-piperidin-1-yl)-xanthine R$_f$ value: 0.27 (silica gel, methylene chloride/methanol/conc. aqueous ammonia=90:10:1)

Mass spectrum (ESI$^+$): m/z=482 [M+H]$^+$ (186) 1-[(imidazo[1,2-a]pyridine-3-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.37 (silica gel, methylene chloride/methanol/conc. aqueous ammonia=90:10:1)

Mass spectrum (ESI$^+$): m/z=447 [M+H]$^+$ (187) 1-[(8-methyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.46 (silica gel, methylene chloride/methanol/conc. aqueous ammonia=90:10:1)

Mass spectrum (ESI$^+$): m/z=461 [M+H]$^+$ (188) 1-[(4-amino-quinazolin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.40 (silica gel, methylene chloride/methanol/conc. aqueous ammonia=90:10:0.1)

Mass spectrum (ESI$^+$): m/z=474 [M+H]$^+$ (189) 1-(2-phenyl-2-oxo-ethyl)-3-methyl-7-((Z)-2-buten-1-yl)-8-(3-amino-piperidin-1-yl)-xanthine Mass spectrum (ESI$^+$): m/z=437 [M+H]$^+$ (190) 1-[(8-methoxy-quinolin-5-yl)methyl]-3-methyl-7-(2-butyn-1-yl)-8-(3-amino-piperidin-1-yl)-xanthine×2 trifluoroacetic acid R$_f$ value: 0.45 (silica gel, methylene chloride/methanol=5:1)

Mass spectrum (ESI$^+$): m/z=488 [M+H]$^+$ (191) 1-[(5-methoxy-quinolin-8-yl)methyl]-3-methyl-7-(2-butyn-1-yl)-8-(3-amino-piperidin-1-yl)-xanthine×trifluoroacetic acid R$_f$ value: 0.20 (silica gel, ethyl acetate/methanol=1:1)

Mass spectrum (ESI$^+$): m/z=488 [M+H]$^+$ (192) 1-[(4-phenyl-quinazolin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.60 (silica gel, methylene chloride/methanol/conc. aqueous ammonia=90:10:1)

Mass spectrum (ESI$^+$): m/z=535 [M+H]$^+$ (193) 1-[(7-methyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

R$_f$ value: 0.48 (silica gel, methylene chloride/methanol/conc. aqueous ammonia=90:10:1)

Mass spectrum (ESI$^+$): m/z=461 [M+H]$^+$ (194) 1-[(2-cyclopropyl-quinazolin-4-yl)methyl]-3-methyl-7-[(1-cyclopenten-1-yl)methyl]-8-(3-amino-piperidin-1-yl)-xanthine (Carried out with 5-6 M isopropanolic hydrochloric acid in methylene chloride)

R$_f$ value: 0.55 (ready-made reversed phase TLC plate (E. Merck), acetonitrile/water/trifluoroacetic acid=50:50:1)

Mass spectrum (ESI$^+$): m/z=527 [M+H]$^+$ (195) 1-(2-oxo-4-phenyl-butyl)-3-methyl-7-(2-butyn-1-yl)-8-((R)-3-amino-piperidin-1-yl)-xanthine×trifluoroacetic acid Mass spectrum (ESI$^+$): m/z=463 [M+H]$^+$ (196) 1-(2-{2-[(methylaminocarbonyl)methylamino]-phenyl}-2-oxo-ethyl)-3-methyl-7-((E)-2-buten-1-yl)-8-((R)-3-amino-piperidin-1-yl)-xanthine R$_f$ value: 0.52 (ready-made reversed phase TLC plate (E. Merck), acetonitrile/water/trifluoroacetic acid=50:50:0.1)

Mass spectrum (ESI$^+$): m/z=523 [M+H]$^+$ (197) 1-[2-(2-oxo-2,3-dihydro-1H-benzoimidazol-4-yl)-2-oxo-ethyl]-3-methyl-7-(2-butyn-1-yl)-8-(3-amino-piperidin-1-yl)-xanthine $R_f$ value: 0.40 (silica gel, methylene chloride/methanol/conc. aqueous ammonia=90:10:1)

Mass spectrum (ESI$^+$): m/z=491 [M+H]$^+$ (198) 1-[(3-difluoromethyl-isoquinolin-1-yl)methyl]-3-methyl-7-(2-butyn-1-yl)-8-(3-amino-piperidin-1-yl)-xanthine×trifluoroacetic acid $R_f$ value: 0.75 (silica gel, methylene chloride/methanol=10:1)

Mass spectrum (ESI$^+$): m/z=508 [M+H]$^+$ (199) 1-[2-(2,2-difluoro-benzo[1,3]dioxol-4-yl)-2-oxo-ethyl]-3-methyl-7-(2-butyn-1-yl)-8-((R)-3-amino-piperidin-1-yl)-xanthine (Carried out with 5-6 M isopropanolic hydrochloric acid in methylene chloride)

$R_f$ value: 0.80 (silica gel, methylene chloride/methanol/conc. aqueous ammonia=96:4:0.5)

Mass spectrum (ESI$^+$): m/z=515 [M+H]$^+$ (200) 1-[(3-methyl-imidazo[1,2-a]pyridin-2-yl)methyl]-3-methyl-7-(2-butyn-1-yl)-8-(3-amino-piperidin-1-yl)-xanthine $R_f$-Wet: 0.45 (silica gel, methylene chloride/methanol/conc. aqueous ammonia=90:10:1)

Mass spectrum (ESI$^+$): m/z=461 [M+H]$^+$ (201) 1-[2-(2,2-difluoro-benzo[1,3]dioxol-4-yl)-2-oxo-ethyl]-3-methyl-7-(2-butyn-1-yl)-8-((S)-3-amino-piperidin-1-yl)-xanthine (Carried out with 5-6 M isopropanolic hydrochloric acid in methylene chloride)

Mass spectrum (ESI$^+$): m/z=515 [M+H]$^+$ (202) 1-[(5-methyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.53 (silica gel, methylene chloride/methanol/conc. aqueous ammonia=90:10:1)

Mass spectrum (ESI$^+$): m/z=461 [M+H]$^+$ (203) 1-[(6-methyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

Melting point: 176.5-178° C.

Mass spectrum (ESI$^+$): m/z=461 [M+H]$^+$ (204) 1-[(3-benzyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

Melting point: 201-204° C.

Mass spectrum (ESI$^+$): m/z=537 [M+H]$^+$ (205) 1-[(4-isopropyl-quinazolin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:0.1)

Mass spectrum (ESI$^+$): m/z=501 [M+H]$^+$ (206) 1-[(2,3-dihydro-benzo[1,4]dioxin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.65 (silica gel, methylene chloride/methanol/conc. aqueous ammonia=90:10:1)

Mass spectrum (ESI$^+$): m/z=465 [M+H]$^+$ (207) 1-[(1-methyl-1H-indol-2-yl)methyl]-3-methyl-7-(2-butyn-1-yl)-8-(3-amino-piperidin-1-yl)-xanthine-hydrochloride (Carried out with 5-6 M isopropanolic hydrochloric acid in methylene chloride)

$R_f$ value: 0.60 (silica gel, methylene chloride/methanol/conc. aqueous ammonia=90:10:1)

Mass spectrum (ESI$^+$): m/z=460 [M+H]$^+$ (208) 1-[(quinolin-3-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:0.1)

Mass spectrum (ESI$^+$): m/z=458 [M+H]$^+$ (209) 1-[(3-phenyl-imidazo[1,2-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:1)

Mass spectrum (ESI$^+$): m/z=523 [M+H]$^+$ (210) 1-[(1H-indol-2-yl)methyl]-3-methyl-7-(2-butyn-1-yl)-8-(3-amino-piperidin-1-yl)-xanthine-hydrochloride $R_f$ value: 0.55 (silica gel, methylene chloride/methanol/conc. aqueous ammonia=90:10:1)

Mass spectrum (ESI$^+$): m/z=446 [M+H]$^+$ (211) 1-[2-(naphthalen-1-yl)-2-oxo-ethyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.60 (silica gel, methylene chloride/methanol/conc. aqueous ammonia=90:10:1)

Mass spectrum (ESI$^+$): m/z=485 [M+H]$^+$ (212) 1-[(5-methoxy-isoquinolin-811)methyl]-3-methyl-7-(2-butyn-1-yl)-8-(3-amino-piperidin-1-yl)-xanthine×trifluoroacetic acid $R_f$ value: 0.50 (silica gel, methylene chloride/methanol=5:1)

Mass spectrum (ESI$^+$): m/z=488 [M+H]$^+$ (213) 1-{[1-(1-cyano-1-methyl-ethyl)-isoquinolin-3-yl]methyl}-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.25 (ready-made reversed phase TLC plate (E. Merck), acetonitrile/water/trifluoroacetic acid=50:50:1)

Mass spectrum (ESI$^+$): m/z=525 [M+H]$^+$ (214) 1-(2-cyanoimino-2-phenyl-ethyl)-3-methyl-7-(2-butyn-1-yl)-8-(3-amino-piperidin-1-yl)-xanthine×trifluoroacetic acid (E/Z-mixture)

Mass spectrum (ESI$^+$): m/z=459 [M+H]$^+$ (215) 1-[(1H-benzoimidazol-2-yl)methyl]-3-methyl-7-(2-butyn-1-yl)-8-(3-amino-piperidin-1-yl)-xanthine×trifluoroacetic acid Mass spectrum (ESI$^+$): m/z=447 [M+H]$^+$ (216) 1-[(1-methyl-1H-benzoimidazol-2-yl)methyl]-3-methyl-7-(2-butyn-1-yl)-8-(3-amino-piperidin-1-yl)-xanthine Mass spectrum (ESI$^+$): m/z=461 [M+H]$^+$ (217) 1-[(4-phenyl-quinazolin-2-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

Mass spectrum (ESI⁺): m/z=535 [M+H]⁺

(218)  1-[(2,3-dimethyl-quinoxalin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:0.1)

Mass spectrum (ESI⁺): m/z=487 [M+H]⁺

(219)  1-[(2-methyl-1H-benzoimidazol-5-yl)methyl]-3-methyl-7-(2-butyn-1-yl)-8-(3-amino-piperidin-1-yl)-xanthine $R_f$ value: 0.35 (silica gel, methylene chloride/methanol/conc. aqueous ammonia=90:10:0.1)

Mass spectrum (ESI⁺): m/z=461 [M+H]⁺

(220)  1-[(4-phenyl-quinazolin-2-yl)methyl]-3-methyl-7-(2-butyn-1-yl)-8-((S)-3-amino-piperidin-1-yl)-xanthine (Carried out with 5-6 M isopropanolic hydrochloric acid in methylene chloride)

Mass spectrum (ESI⁺): m/z=535 [M+H]⁺

(221)  1-[2-(quinolin-8-yl-]-2-oxo-ethyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.48 (silica gel, methylene chloride/methanol/conc. aqueous ammonia=90:10:1)

Mass spectrum (ESI⁺): m/z=486 [M+H]⁺

(222)  1-[(3,4-dimethyl-6,7-dihydro-5H-[2]pyridin-1-yl)methyl]-3-methyl-7-(2-butyn-1-yl)-8-(3-amino-piperidin-1-yl)-xanthine×trifluoroacetic acid $R_f$ value: 0.25 (aluminium oxide, methylene chloride/methanol=20:1)

Mass spectrum (ESI⁺): m/z=476 [M+H]⁺

(223)  1-[(3,4-dimethyl-5,6,7,8-tetrahydro-isoquinolin-1-yl)methyl]-3-methyl-7-(2-butyn-1-yl)-8-(3-amino-piperidin-1-yl)-xanthine×trifluoroacetic acid $R_f$ value: 0.50 (aluminium oxide, methylene chloride/methanol=20:1)

Mass spectrum (ESI⁺): m/z=490 [M+H]⁺

(224)  1-[2-(1H-indol-4-yl)-2-oxo-ethyl]-3-methyl-7-(2-butyn-1-yl)-8-(3-amino-piperidin-1-yl)-xanthine $R_f$ value: 0.52 (silica gel, methylene chloride/methanol/conc. aqueous ammonia=90:10:1)

Mass spectrum (ESI⁺): m/z=474 [M+H]⁺

(225)  1-[(1H-benzoimidazol-5-yl)methyl]-3-methyl-7-(2-butyn-1-yl)-8-(3-amino-piperidin-1-yl)-xanthine $R_f$ value: 0.50 (silica gel, methylene chloride/methanol/conc. aqueous ammonia=90:10:1)

Mass spectrum (ESI⁺): m/z=447 [M+H]⁺

(226)  1-[(pyrazolo[1,5-a]pyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.47 (silica gel, methylene chloride/methanol/conc. aqueous ammonia=90:10:1)

Mass spectrum (ESI⁺): m/z=447 [M+H]⁺

(227)  1-[(1-methyl-2-oxo-1,2-dihydro-quinolin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.40 (silica gel, methylene chloride/methanol/conc. aqueous ammonia=90:10:1)

Mass spectrum (ESI⁺): m/z=488 [M+H]⁺

(228)  1-[(2-oxo-1,2-dihydro-quinolin-6-yl)methyl]-3-methyl-7-(2-butyn-1-yl)-8-(3-amino-piperidin-1-yl)-xanthine $R_f$ value: 0.23 (silica gel, methylene chloride/methanol/conc. aqueous ammonia=90:10:1)

Mass spectrum (ESI⁺): m/z=474 [M+H]⁺

(229)  1-[(2,3,8-trimethyl-quinoxalin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.37 (silica gel, methylene chloride/methanol/conc. aqueous ammonia=90:10:1)

Mass spectrum (ESI⁺): m/z=501 [M+H]⁺

(230)  1-[(8-methyl-quinoxalin-6-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.35 (silica gel, methylene chloride/methanol/conc. aqueous ammonia=90:10:1)

Mass spectrum (ESI⁺): m/z=473 [M+H]⁺

(231)  1-[(4-methyl-phthalazin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.55 (ready-made reversed phase TLC plate (E. Merck), acetonitrile/water/trifluoroacetic acid=50:50:1)

Mass spectrum (ESI⁺): m/z=473 [M+H]⁺

(232)  1-[(4-bromo-3-methoxy-isoquinolin-1-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.40 (ready-made reversed phase TLC plate (E. Merck), acetonitrile/water/trifluoroacetic acid=50:50:1)

Mass spectrum (ESI⁺): m/z=566, 568 [M+H]⁺

(233)  1-(2-phenyl-2-oxo-ethyl)-3-methyl-7-((E)-1-buten-1-yl)-8-(3-amino-piperidin-1-yl)-xanthine $R_f$ value: 0.31 (silica gel, methylene chloride/methanol/conc. aqueous ammonia=90:10:1)

Mass spectrum (ESI⁺): m/z=437 [M+H]⁺

(234)  1-[(4-difluoromethoxy-naphthalen-1-yl)methyl]-3-methyl-7-(2-butyn-1-yl)-8-((R)-3-amino-piperidin-1-yl)-xanthine $R_f$ value: 0.08 (silica gel, methylene chloride/methanol/conc. aqueous ammonia=95:5:1)

Mass spectrum (ESI⁺): m/z=523 [M+H]⁺

(235)  1-[2-(1H-indol-7-yl)-2-oxo-ethyl]-3-methyl-7-(2-butyn-1-yl)-8-(3-amino-piperidin-1-yl)-xanthine×trifluoroacetic acid $R_f$ value: 0.46 (silica gel, methylene chloride/methanol/conc. aqueous ammonia=90:10:1)

Mass spectrum (ESI⁺): m/z=474 [M+H]⁺

(236)  1-[(E)-3-(2-nitro-phenyl)-2-propen-1-yl]-3-methyl-7-(2-butyn-1-yl)-8-(3-amino-piperidin-1-yl)-xanthine Mass spectrum (ESI⁺): m/z=478 [M+H]⁺

(237)  1-((E)-3-pentafluorophenyl-2-propen-1-yl)-3-methyl-7-(2-butyn-1-yl)-8-(3-amino-piperidin-1-yl)-xanthine Mass spectrum (ESI⁺): m/z=523 [M+H]⁺

(238)  1-[(4-nitro-naphthalen-1-yl)methyl]-3-methyl-7-(2-butyn-1-yl)-8-((R)-3-amino-piperidin-1-yl)-xanthine $R_f$ value: 0.38 (silica gel, methylene chloride/methanol/conc. aqueous ammonia=90:10:1)

Mass spectrum (ESI⁺): m/z=502 [M+H]⁺

(239)  1-{[1-(2-cyano-ethyl)-1H-benzoimidazol-2-yl]methyl}-3-methyl-7-(2-butyn-1-yl)-8-(3-amino-piperidin-1-yl)-xanthine-hydrochloride (Carried out with 5-6 M isopropanolic hydrochloric acid in methylene chloride)

$R_f$ value: 0.55 (ready-made reversed phase TLC plate (E. Merck), acetonitrile/water/trifluoroacetic acid=50:50:0.1)

Mass spectrum (ESI$^+$): m/z=500 [M+H]$^+$ (240) 1-({1-[(methylaminocarbonyl)methyl]-1H-benzoimidazol-2-yl}methyl)-3-methyl-7-(2-butyn-1-yl)-8-(3-amino-piperidin-1-yl)-xanthine×trifluoroacetic acid Mass spectrum (ESI$^+$): m/z=518 [M+H]$^+$ (241) 1-[(1-benzyl-1H-benzoimidazol-2-yl)methyl]-3-methyl-7-(2-butyn-1-yl)-8-(3-amino-piperidin-1-yl)-xanthine $R_f$ value: 0.47 (ready-made reversed phase TLC plate (E. Merck), acetonitrile/water/trifluoroacetic acid=50:50:0.1)

Mass spectrum (ESI$^+$): m/z=537 [M+H]$^+$ (242) 1-[(benzooxazol-2-y)methyl]-3-methyl-7-(2-butyn-1-yl)-8-(3-amino-piperidin-1-yl)-xanthine×trifluoroacetic acid $R_f$ value: 0.50 (ready-made reversed phase TLC plate (E. Merck), acetonitrile/water/trifluoroacetic acid=50:50:0.1)

Mass spectrum (ESI$^+$): m/z=448 [M+H]$^+$ (243) 1-[(5-nitro-benzooxazol-2-y)methyl]-3-methyl-7-(2-butyn-1-yl)-8-(3-amino-piperidin-1-yl)-xanthine $R_f$ value: 0.49 (ready-made reversed phase TLC plate (E. Merck), acetonitrile/water/trifluoroacetic acid=50:50:0.1)

Mass spectrum (ESI$^+$): m/z=493 [M+H]$^+$ (244) 1-[(3-methyl-isoquinolin-1-yl)methyl]-3-methyl-7-(3-methyl-1-buten-1-yl)-8-((R)-3-amino-piperidin-1-yl)-xanthine $R_f$ value: 0.21 (silica gel, methylene chloride/methanol/conc. aqueous ammonia=90:10:1)

Mass spectrum (ESI$^+$): m/z=488 [M+H]$^+$ (245) 1-[(quinolin-7-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.55 (silica gel, methylene chloride/methanol/conc. aqueous ammonia=90:10:1)

Mass spectrum (ESI$^+$): m/z=458 [M+H]$^+$ (246) 1-[([1,5]naphthyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.51 (silica gel, methylene chloride/methanol/conc. aqueous ammonia=90:10:1)

Mass spectrum (ESI$^+$): m/z=459 [M+H]$^+$ (247) 1-[(8-methyl-quinoxalin-6-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

$R_f$ value: 0.49 (silica gel, methylene chloride/methanol/conc. aqueous ammonia=90:10:1)

Mass spectrum (ESI$^+$): m/z=473 [M+H]$^+$ (248) 1-[(2,3,8-trimethyl-quinoxalin-6-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

$R_f$ value: 0.46 (silica gel, methylene chloride/methanol/conc. aqueous ammonia=90:10:1)

Mass spectrum (ESI$^+$): m/z=501 [M+H]$^+$ (249) 1-[([1,6]naphthyridin-5l1)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:1)

Mass spectrum (ESI$^+$): m/z=459 [M+H]$^+$ (250) 1-[([1,8]naphthyridin-2-yl)methyl]-3-methyl-7-(2-butyn-1-yl)-8-(3-amino-piperidin-1-yl)-xanthine (Carried out with 5-6 M isopropanolic hydrochloric acid in methylene chloride)

$R_f$ value: 0.45 (silica gel, methylene chloride/methanol/conc. aqueous ammonia=90:10:1)

Mass spectrum (ESI$^+$): m/z=459 [M+H]$^+$ (251) 1-[(4-fluoro-naphthalen-1-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:1)

Mass spectrum (ESI$^+$): m/z=475 [M+H]$^+$ (252) 1-[([1,5]naphthyridin-2-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

Mass spectrum (ESI$^+$): m/z=459 [M+H]$^+$ (253) 1-[2-(3-methyl-2-oxo-2,3-dihydro-benzooxazol-4-yl)-2-oxo-ethyl]-3-methyl-7-(2-butyn-1-yl)-8-((R)-3-amino-piperidin-1-yl)-xanthine (Carried out with 5-6 M isopropanolic hydrochloric acid in methylene chloride)

Melting point: 187-189° C.

Mass spectrum (ESI$^+$): m/z=506 [M+H]$^+$ (254) 1-[(8-phenyl-quinoxalin-6-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

$R_f$ value: 0.50 (silica gel, methylene chloride/methanol/conc. aqueous ammonia=90:10:1)

Mass spectrum (ESI$^+$): m/z=535 [M+H]$^+$ (255) 1-[([1,5]naphthyridine-4-yl)methyl]-3-methyl-7-(2-butyn-1-yl)-8-((R)-3-amino-piperidin-1-yl)-xanthine (Carried out with 5-6 M isopropanolic hydrochloric acid in methylene chloride)

$R_f$ value: 0.52 (silica gel, methylene chloride/methanol/conc. aqueous ammonia=90:10:1)

Mass spectrum (ESI$^+$): m/z=459 [M+H]$^+$ (256) 1-((E)-3-pentafluorophenyl-allyl)-3-methyl-7-(2-butyn-1-yl)-8-((R)-3-amino-piperidin-1-yl)-xanthine Mass spectrum (ESI$^+$): m/z=523 [M+H]$^+$ (257) 1-[(E)-3-(2-trifluoromethyl-phenyl)-allyl]-3-methyl-7-(2-butyn-1-yl)-8-((R)-3-amino-piperidin-1-yl)-xanthine Mass spectrum (ESI$^+$): m/z=501 [M+H]$^+$ (258) 1-[(E)-3-(3-trifluoromethyl-phenyl)-allyl]-3-methyl-7-(2-butyn-1-yl)-8-((R)-3-amino-piperidin-1-yl)-xanthine Mass spectrum (ESI$^+$): m/z=501 [M+H]$^+$ (259) 1-[(E)-3-(4-trifluoromethyl-phenyl)-allyl]-3-methyl-7-(2-butyn-1-yl)-8-((R)-3-amino-piperidin-1-yl)-xanthine Mass spectrum (ESI$^+$): m/z=501 [M+H]$^+$ (260) 1-[(3-trifluoromethyl-isoquinolin-1-yl)methyl]-3-methyl-7-(2-butyn-1-yl)-8-((R)-3-amino-piperidin-1-yl)-xanthine×trifluoroacetic acid Mass spectrum (ESI$^+$): m/z=526 [M+H]$^+$ (261) 1-[(3-methyl-isoquinolin-1-yl)methyl]-3-isopropyl-7-(2-butyn-1-yl)-8-((R)-3-amino-piperidin-1-yl)-xanthine (262) 1-[(3-methyl-isoquinolin-1-yl)methyl]-3-(4-fluorophenyl)-7-(2-butyn-1-yl)-8-((R)-3-amino-piperidin-1-yl)-xanthine (263) 1-[(3-methyl-isoquinolin-1-yl)methyl]-3-methyl-7-(2-cyano-benzyl)-8-(3-amino-piperidin-1-yl)-xanthine
(Carried out with 5-6 M isopropanolic hydrochloric acid in methylene chloride)
$R_f$ value: 0.51 (ready-made reversed phase TLC plate (E. Merck), acetonitrile/water/trifluoroacetic acid=50:50:1)
Mass spectrum (ESI$^+$): m/z=535 [M+H]$^+$ (264) 1-[(3-difluoromethyl-isoquinolin-1-yl)methyl]-3-methyl-7-(2-butyn-1-yl)-8-((R)-3-amino-piperidin-1-yl)-xanthine
Mass spectrum (ESI$^+$): m/z=508 [M+H]$^+$ (265) 1-[(4-chloro-3-methoxy-isoquinolin-1-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Mass spectrum (ESI$^+$): m/z=522, 524 [M+H]$^+$
$R_f$ value: 0.40 (ready-made reversed phase TLC plate (E. Merck), acetonitrile/water/trifluoroacetic acid=50:50:1)

(266) 1-[(4-ethoxy-quinazolin-2-yl)methyl]-3-methyl-7-(2-butyn-1-yl)-8-(3-amino-piperidin-1-yl)-xanthine
(Carried out with 1 M ethereal hydrochloric acid)
$R_f$ value: 0.60 (ready-made reversed phase TLC plate (E. Merck), acetonitrile/water/trifluoroacetic acid=50:50:1)
Mass spectrum (ESI$^+$): m/z=503 [M+H]$^+$ (267) 1-[(4-isopropyloxy-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.55 (ready-made reversed phase TLC plate (E. Merck), acetonitrile/water/trifluoroacetic acid=50:50:1)
Mass spectrum (ESI$^+$): m/z=517 [M+H]$^+$ (268) 1-[(2-methyl-benzothiazol-6-yl)methyl]-3-methyl-7-(2-butyn-1-yl)-8-(3-amino-piperidin-1-yl)-xanthine
(Carried out with 5-6 M isopropanolic hydrochloric acid in methylene chloride)
Melting point: 167° C.
Mass spectrum (ESI$^+$): m/z=478 [M+H]$^+$ (269) 1-[(3-phenyl-isoquinolin-1-yl)methyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.45 (ready-made reversed phase TLC plate (E. Merck), acetonitrile/water/trifluoroacetic acid=50:50:1)
Mass spectrum (ESI$^+$): m/z=534 [M+H]$^+$ (270) 1-[(4-phenyloxy-quinazolin-2-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.60 (ready-made reversed phase TLC plate (E. Merck), acetonitrile/water/trifluoroacetic acid=50:50:1)
Mass spectrum (ESI$^+$): m/z=551 [M+H]$^+$ (271) 1-[(4-phenyl-quinazolin-2-yl)methyl]-3-cyclopropyl-7-(2-butyn-1-yl)-8-(3-amino-piperidin-1-yl)-xanthine
(Carried out with 5-6 M isopropanolic hydrochloric acid in methylene chloride)
$R_f$ value: 0.45 (ready-made reversed phase TLC plate (E. Merck), acetonitrile/water/trifluoroacetic acid=50:50:1)
Mass spectrum (ESI$^+$): m/z=561 [M+H]$^+$ (272) 1-[(3-methyl-isoquinolin-1-yl)methyl]-3-cyclopropyl-7-(2-butyn-1-yl)-8-(3-amino-piperidin-1-yl)-xanthine
(Carried out with 5-6 M isopropanolic hydrochloric acid in methylene chloride)
$R_f$ value: 0.55 (ready-made reversed phase TLC plate (E. Merck), acetonitrile/water/trifluoroacetic acid=50:50:1)
Mass spectrum (ESI$^+$): m/z=498 [M+H]$^+$ (273) 1-[(2-phenyl-quinazolin-4-yl)methyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.50 (ready-made reversed phase TLC plate (E. Merck), acetonitrile/water/trifluoroacetic acid=50:50:1)
Mass spectrum (ESI$^+$): m/z=535 [M+H]$^+$ (274) 1-[2-(2-methoxy-phenyl)-2-oxo-ethyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.29 (silica gel, methylene chloride/methanol/conc. aqueous ammonia=90:10:1)
Mass spectrum (ESI$^+$): m/z=465 [M+H]$^+$ (275) 1-[2-(3-methoxy-phenyl)-2-oxo-ethyl]-3-methyl-7-(2-butyn-1-yl)-8-(3-amino-piperidin-1-yl)-xanthine
(Carried out with 5-6 M isopropanolic hydrochloric acid in methylene chloride)
$R_f$ value: 0.27 (silica gel, methylene chloride/methanol/conc. aqueous ammonia=90:10:1)
Mass spectrum (ESI$^+$): m/z=465 [M+H]$^+$ (276) 1-[2-(3-trifluoromethoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.29 (silica gel, methylene chloride/methanol/conc. aqueous ammonia=90:10:1)
Mass spectrum (ESI$^+$): m/z=519 [M+H]$^+$ (277) 1-[2-(biphenyl-2-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.35 (ready-made reversed phase TLC plate (E. Merck), acetonitrile/water/trifluoroacetic acid=50:50:1)
Mass spectrum (ESI$^+$): m/z=511 [M+H]$^+$ (278) 1-[2-(biphenyl-3-yl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.35 (ready-made reversed phase TLC plate (E. Merck), acetonitrile/water/trifluoroacetic acid=50:50:1)
Mass spectrum (ESI$^+$): m/z=511 [M+H]$^+$ (279) 1-[2-(3-isopropyloxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.20 (silica gel, methylene chloride/methanol/conc. aqueous ammonia=90:10:1)
Mass spectrum (ESI$^+$): m/z=493 [M+H]$^+$ (280) 1-[(3-methyl-isoquinolin-1-yl)methyl]-3-cyclopropyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.50 (ready-made reversed phase TLC plate (E. Merck), acetonitrile/water/trifluoroacetic acid=50:50:1)
Mass spectrum (ESI$^+$): m/z=498 [M+H]$^+$ (281) 1-[(4-phenyl-quinazolin-2-yl)methyl]-3-cyclopropyl-7-(2-butyn-1-yl)-8-((R)-3-amino-piperidin-1-yl)-xanthine
(Carried out with 5-6 M isopropanolic hydrochloric acid in methylene chloride)
$R_f$ value: 0.45 (ready-made reversed phase TLC plate (E. Merck), acetonitrile/water/trifluoroacetic acid=50:50:1)
Mass spectrum (ESI$^+$): m/z=561 [M+H]$^+$ (282) 1-[(4-cyano-naphthalen-1-yl)methyl]-3-cyclopropyl-7-(2-butyn-1-yl)-8-((R)-3-amino-piperidin-1-yl)-xanthine
(Carried out with 5-6 M isopropanolic hydrochloric acid in methylene chloride)
Melting point: 191° C.
Mass spectrum (ESI$^+$): m/z=508 [M+H]$^+$ (283) 1-[2-(2-phenyloxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.40 (ready-made reversed phase TLC plate (E. Merck), acetonitrile/water/trifluoroacetic acid=50:50:1)
Mass spectrum (ESI$^+$): m/z=527 [M+H]$^+$ (284) 1-[2-(3-ethoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.29 (silica gel, methylene chloride/methanol/conc. aqueous ammonia=90:10:1)
Mass spectrum (ESI$^+$): m/z=479 [M+H]$^+$ (285) 1-[2-(3-methoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.28 (silica gel, methylene chloride/methanol/conc. aqueous ammonia=90:10:1)
Mass spectrum (ESI$^+$): m/z=465 [M+H]$^+$ (286) 1-[2-(2-methoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.34 (silica gel, methylene chloride/methanol/conc. aqueous ammonia=90:10:1)
Mass spectrum (ESI$^+$): m/z=465 [M+H]$^+$ (287) 1-[(3-methyl-isoquinolin-1-yl)methyl]-3-methyl-7-(2-chloro-benzyl)-8-((R)-3-amino-piperidin-1-yl)-xanthine
Mass spectrum (ESI$^+$): m/z=544, 546 [M+H]$^+$ (288) 1-[(3-methyl-isoquinolin-1-yl)methyl]-3-methyl-7-(2-bromo-benzyl)-8-((R)-3-amino-piperidin-1-yl)-xanthine
Mass spectrum (ESI$^+$): m/z=588, 590 [M+H]$^+$ (289) 1-[(1,2,3,4-tetrahydro-phenanthridin-6-yl)methyl]-3-methyl-7-(2-butyn-1-yl)-8-(3-amino-piperidin-1-yl)-xanthinextrifluoroacetic acid
R$_f$ value: 0.75 (aluminium oxide, methylene chloride/methanol=10:1)
Mass spectrum (ESI$^+$): m/z=512 [M+H]$^+$ (290) 1-[2-(3-difluoromethoxy-phenyl)-2-oxo-ethyl]-3-methyl-7-(2-butyn-1-yl)-8-((R)-3-amino-piperidin-1-yl)-xanthine
(Carried out with 5-6 M isopropanolic hydrochloric acid in methylene chloride)
R$_f$ value: 0.28 (silica gel, methylene chloride/methanol/conc. aqueous ammonia=90:10:1)
Mass spectrum (ESI$^+$): m/z=501 [M+H]$^+$ (291) 1-[(3-methyl-isoquinolin-1-yl)methyl]-3-methyl-7-(2-ethynyl-benzyl)-8-((R)-3-amino-piperidin-1-yl)-xanthine (292) 1-[(3-methyl-isoquinolin-1-yl)methyl]-3-phenyl-7-(2-butyn-1-yl)-8-((R)-3-amino-piperidin-1-yl)-xanthine (293) 1-[(phenanthren-9-yl)methyl]-3-methyl-7-(2-butyn-1-yl)-8-((R)-3-amino-piperidin-1-yl)-xanthine (294) 1-[(4-methyl-quinazolin-2-yl)methyl]-3-methyl-7-(2-chloro-benzyl)-8-((R)-3-amino-piperidin-1-yl)-xanthine
R$_f$ value: 0.35 (silica gel, methylene chloride/methanol/triethylamine=90:10:1)
Mass spectrum (ESI$^+$): m/z=545, 547 [M+H]$^+$ (295) 1-[(4-phenyl-quinazolin-2-yl)methyl]-3-methyl-7-(2-chloro-benzyl)-8-((R)-3-amino-piperidin-1-yl)-xanthine
R$_f$ value: 0.40 (silica gel, methylene chloride/methanol/triethylamine=90:10:1)
Mass spectrum (ESI$^+$): m/z=607, 609 [M+H]$^+$ Example 3

1-[2-(3-carboxymethoxy-phenyl)-2-oxo-ethyl]-3-methyl-7-(3-methyl-2-buten-1-yl)-8-(3-amino-piperidin-1-yl)-xanthine Prepared by saponifying 70 mg of 1-(2-{3-[(methoxycarbonyl)methoxy]-phenyl}-2-oxo-ethyl)-3-methyl-7-(3-methyl-2-buten-1-yl)-8-(3-amino-piperidin-1-yl)-xanthine with 0.10 ml of 4 M potassium hydroxide solution in a mixture of 1 ml of tetrahydrofuran and 0.5 ml of methanol at ambient temperature.

Yield: 57 mg (84% of theory)
R$_f$ value: 0.55 (ready-made reversed phase TLC plate (E. Merck), acetonitrile/water/trifluoroacetic acid=50:50:0.1)
Mass spectrum (ESI$^+$): m/z=525 [M+H]$^+$ The following compounds are obtained analogously to Example 3:

(1) 1-[2-(2-carboxymethoxy-phenyl)-2-oxo-ethyl]-3-methyl-7-(3-methyl-2-buten-1-yl)-8-(3-amino-piperidin-1-yl)-xanthine
(Carried out with sodium hydroxide solution)
Mass spectrum (ESI$^-$): m/z=523 [M−H]$^-$ Example 4

Coated Tablets Containing 75 mg of Active Substance

1 Tablet Core Contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

Example 5

Tablets Containing 100 mg of Active Substance

Composition:
1 tablet contains:

| | |
|---|---:|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:
The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.
Weight of tablet: 220 mg
Diameter: 10 mm, biplanar, facetted on both sides and notched on one side.

Example 6

Tablets Containing 150 mg of Active Substance

Composition:
1 Tablet Contains:

| | |
|---|---:|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:
The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.
Weight of tablet: 300 mg
die: 10 mm, flat

Example 7

Hard Gelatine Capsules Containing 150 mg of Active Substance

1 Capsule Contains:

| | |
|---|---:|
| active substance | 150.0 mg |
| corn starch (dried) | approx. 80.0 mg |
| lactose (powdered) | approx. 87.0 mg |
| magnesium stearate | 3.0 mg |
| | approx. 420.0 mg |

Preparation:
The active substance is mixed with the excipients, passed through a screen with a mesh size of 0.75 mm and homogeneously mixed using a suitable apparatus. The finished mixture is packed into size 1 hard gelatine capsules.
Capsule filling: approx. 320 mg
Capsule shell: size 1 hard gelatine capsule.

Example 8

Suppositories Containing 150 mg of Active Substance

1 Suppository Contains:

| | |
|---|---:|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled moulds.

Example 9

Suspension Containing 50 mg of Active Substance 100 ml of Suspension Contain:

| | |
|---|---:|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water ad | 100 ml |

Preparation:
The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.
5 ml of suspension contain 50 mg of active substance.

Example 10

Ampoules Containing 10 mg Active Substance

Composition:

| | |
|---|---:|
| active substance | 10.0 mg |
| 0.01N hydrochloric acid q.s. | |
| double-distilled water ad | 2.0 ml |

Preparation:

The active substance is dissolved in the necessary amount of 0.01 N HCl, made isotonic with common salt, filtered sterile and transferred into 2 ml ampoules.

Example 11

Ampoules Containing 50 mg of Active Substance

Composition:

| active substance | 50.0 mg |
|---|---|
| 0.01N hydrochloric acid q.s. | |
| double-distilled waterad | 10.0 ml |

Preparation:

The active substance is dissolved in the necessary amount of 0.01 N HCl, made isotonic with common salt, filtered sterile and transferred into 10 ml ampoules.

What is claimed is:

1. 1-[([1,5]naphthyridin-2-yl)methyl]-3-methyl-7-(2-butyn-1-yl)-8-((R)-3-amino-piperidin-1-yl)-xanthine, or a pharmaceutically acceptable salt thereof.

2. The pharmaceutically acceptable salt of the compound of claim 1.

3. The free-base form of the compound of claim 1.

4. A pharmaceutical composition comprising the compound of claim 1, or a pharmaceutically acceptable salt thereof, and a pharmaceutically acceptable carrier.

* * * * *